United States Patent
Ebata et al.

(10) Patent No.: US 6,908,722 B2
(45) Date of Patent: Jun. 21, 2005

(54) ACID GENERATOR, SULFONIC ACID, SULFONIC ACID DERIVATIVES AND RADIATION-SENSITIVE RESIN COMPOSITION

(75) Inventors: Satoshi Ebata, Tokyo (JP); Eiji Yoneda, Tokyo (JP); Tomoki Nagai, Tokyo (JP); Tatsuya Toneri, Tokyo (JP); Yong Wang, Tokyo (JP); Haruo Iwasawa, Tokyo (JP); Yukio Nishimura, Tokyo (JP)

(73) Assignee: JSR Corporation, Tokyo (JP)

( * ) Notice: Subject to any disclaimer, the term of this patent is extended or adjusted under 35 U.S.C. 154(b) by 329 days.

(21) Appl. No.: 10/183,441

(22) Filed: Jun. 28, 2002

(65) Prior Publication Data

US 2003/0113658 A1 Jun. 19, 2003

(30) Foreign Application Priority Data

| Jun. 29, 2001 | (JP) | 2001-200154 |
| Dec. 5, 2001 | (JP) | 2001-371311 |
| Mar. 22, 2002 | (JP) | 2002-081235 |

(51) Int. Cl.$^7$ .............................................. G03F 7/00
(52) U.S. Cl. .................. 430/270.1; 430/913; 430/914; 549/5; 549/6; 549/13; 549/29; 568/19; 568/27; 568/28
(58) Field of Search .............................. 430/270.1, 913, 430/914; 549/5, 6, 13, 29; 568/19, 27, 28

(56) References Cited

U.S. PATENT DOCUMENTS

| 2,852,554 | A | | 9/1958 | England et al. |
| 4,371,710 | A | * | 2/1983 | Umemoto ..................... 568/35 |
| 4,650,913 | A | * | 3/1987 | Feiring ........................ 570/144 |
| 6,358,665 | B1 | * | 3/2002 | Pawlowski et al. ....... 430/270.1 |
| 2002/0051933 | A1 | * | 5/2002 | Kodama et al. .......... 430/270.1 |
| 2002/0102491 | A1 | * | 8/2002 | Kodama et al. .......... 430/270.1 |
| 2003/0194640 | A1 | * | 10/2003 | Sato ........................ 430/270.1 |

FOREIGN PATENT DOCUMENTS

| DE | 295421 A | * | 10/1983 | ............ G03C/1/73 |
| EP | 794457 A2 | * | 9/1997 | ........... G03F/7/004 |
| EP | 0 849 634 | | 6/1998 | |
| EP | 1 099 691 | | 5/2001 | |
| EP | 1 199 603 | | 4/2002 | |
| JP | 3-231592 | | 10/1991 | |
| JP | 8-179508 | | 7/1996 | |
| JP | 2002139838 A | * | 5/2002 | ........... G03F/7/039 |
| WO | WO 02/42845 | | 5/2002 | |

OTHER PUBLICATIONS

Uwe Hartwig et al., "Bis(trifluormethyl)sulfen, $(CF_3)_2C{=}SO_2$: seine Darstellung und Isolierung als Amin–Addukt" *Chem Ber.* 123 (1990) pp.: 595–598.

(Continued)

*Primary Examiner*—Amanda Walke
(74) *Attorney, Agent, or Firm*—Steven B. Kelber; DLA Piper Rudnick Gray Cary US LLP

(57) ABSTRACT

A novel photoacid generator containing a structure of the following formula (I),

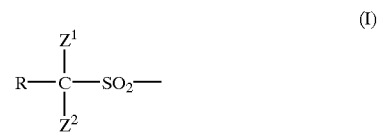

wherein R is a monovalent organic group with a fluorine content of 50 wt % or less, a nitro group, a cyano group, or a hydrogen atom, and $Z^1$ and $Z^2$ are individually a fluorine atom or a linear or branched perfluoroalkyl group having 1–10 carbon atoms, is provided. When used in a chemically amplified radiation-sensitive resin composition, the photoacid generator exhibits high transparency, comparatively high combustibility, and no bioaccumulation, and produces an acid exhibiting high acidity, high boiling point, moderately short diffusion length in the resist coating, and low dependency to mask pattern density.

21 Claims, 15 Drawing Sheets

OTHER PUBLICATIONS

Andrew E. Feiring et al., "Aromatic monomers with pendant fluoroalkylsulfonate and sulfonimide groups", *Journal of Fluorine Chemistry* 105 (2000) pp.: 129–135.

R.N. Haszeldine, "Synthesis of Polyfluoroalkanes containing Functional Groups from Chlorotrifluoroethylene, and the Short–chain Polymerisation of Olefins", *Haszeldine: Fluoro–olefins*, Part IV, (1955) pp.: 4291–4301.

Qing–Yun Chen et al., "An Improved Method for Synthesizing Difluoromethanesulfonic Acid", *Journal of Fluorine Chemistry* 47 (1990) pp.: 509–514.

E. Gille et al., "Über die Reaktion von Chlortrifluorethen mit Schwefeltrioxid", *Journal of Fluorine Chemistry* 69 (1994) pp.: 145–149.

Chang–Ming Hu et al., "Redox–Initiated Per(poly)fluoroalkylation of Olefins by Per(poly)fluoroalkyl Chlorides", *J. Org. Chem.* 56 (1991) pp.: 6348–6351.

Donald J. Burton et al., "Synthesis of (Sulfodifluoromethyl)phosphonic Acid", *J. Am. Chem. Soc.* 111 (1989) pp.: 1773–1776.

Christopher C. Kotoris et al., "Preparation of Benzylic α,α–Difluoronitriles, –tetrazoles, and –sulfonates via Electrophilic Fluorination", *J. Org. Chem.* 63 (1998) pp.: 8052–8057.

Andrew E. Feiring et al., "Synthesis of partially fluorinated monomers and polymers for ion–exchange resins", *Journal of Fluorine Chemistry* 93 (1999) pp.: 93–101.

Christopher C. Kotoris et al., "Novel Phosphate Mimetics for the Design of Nonopeptidyl Inhibitors of Protein Tyrosine Phosphatases", *Bioorganic & Medicinal Chemistry Letters* 8 (1998) pp.: 3275–3280.

N.D. Volkov et al., "Halogeno and pseudohalogeno difluoromethanesulfonylfluorides", *Journal of Fluorine Chemistry* 84 (1997) pp.: 135–139.

Karl E. Rapp et al., "Reactions of Polyfluoro Olefins Sulfides and Sulfones", Contribution from the Research Laboratories, K–25 Plant, Carbide and Carbon Chemicals Corporation 5 (1950) pp.: 3642–3646.

D.C. England et al., "Reactions of Fluoroölefins with Sulfur Trioxide", Contribution No. 580 from the Central Research Department, Experimental Station, E.I. duPong de nemours and Co. 8 (1960) pp.: 6181–6188.

D. Sianesi et al., "A Novel Photo–Reaction of Sulfur Dioxide with Fluoroolefins", *Tetrahedron Letters* 16 (1970) pp.: 1313–1314.

R.D. Trepka et al., "Acidities and Partition Coefficients of Fluoromethanesulfonamides", *J. Org. Chem.* 8 (1974) pp.: 1094–1098.

Crivello, "Cationic Polymerization—Iodonium and Sulfonium Salt Photoinitiators", Advances in Polymer Science, C. Spring–Verlag, Berlin Heidelberg, 62, 1–48 (1984).

Hu, et al., "Synthesis of Perhaloalkanesulfonyl Halides and Their Sulfonimide Derivatives", Inorganic Chemistry, 32, 23, 5007–5010 (1993).

Oppolzer, "Intermolecular Diels—Alder Reactions: Introduction", Chapter 4.1.1, Comprehensive Organic Synthesis, B.M. Trost, et al. (ed.) Pergamon Press, New York, 5, 316 (1991).

* cited by examiner

ACID GENERATOR, SULFONIC ACID, SULFONIC ACID DERIVATIVES AND RADIATION-SENSITIVE RESIN COMPOSITION

BACKGROUND OF THE INVENTION

1. Field of the Invention

The present invention relates to an acid generator, sulfonic acid, sulfonic acid derivative, and radiation-sensitive resin composition. More particularly, the present invention relates to a photoacid generator suitable for use in a radiation-sensitive resin composition which is used as a chemically amplified resist for microfabrication utilizing various types of radiation, for example, deep ultraviolet rays such as a KrF excimer laser, ArF excimer laser, $F_2$ excimer laser, or EUV (extreme ultraviolet), X-rays such as synchrotron radiation, or charged particle rays such as electron beams, to a sulfonic acid generated from said acid generator, a sulfonic acid derivative useful as a raw material or intermediate for synthesizing said acid generator, and a positive-tone or negative-tone radiation-sensitive resin composition containing said acid generator.

2. Description of the Background Art

In the field of microfabrication represented by fabrication of integrated circuit devices, a lithographic technology enabling microfabrication with a line width of 0.20 μm or less has been demanded in order to achieve higher integration.

A conventional lithographic process utilizes near ultraviolet rays such as i-line radiation. It is known in the art that microfabrication with a line width of a sub-quarter micron order using near ultraviolet rays is very difficult.

Therefore, use of radiation with a shorter wavelength has been studied for enabling microfabrication with a line width of 0.20 μm or less. As radiation with a shorter wavelength, deep ultraviolet rays represented by a line spectrum of a mercury lamp and an excimer laser, X-rays, electron beams, and the like can be given. Of these, a KrF excimer laser (wavelength: 248 nm), an ArF excimer laser (wavelength: 193 nm), an $F_2$ excimer laser (wavelength: 157 nm), EUV (wavelength 13 nm), and electron beams have attracted attention.

As a radiation-sensitive resin composition applicable to shorter wavelength radiation, a number of compositions utilizing a chemical amplification effect between a component having an acid-cleavable functional group and a photoacid generator which generates an acid upon irradiation (hereinafter called "exposure") has been proposed. Such a composition is hereinafter called a chemically-amplified radiation-sensitive composition.

As the chemically-amplified radiation-sensitive composition, Japanese Patent Publication No. 27660/1990 discloses a composition comprising a polymer containing a t-butyl ester group of carboxylic acid or a t-butylcarbonate group of phenol and a photoacid generator. This composition utilizes the effect of the polymer to release a t-butyl ester group or t-butyl carbonate group by the action of an acid generated upon exposure to form an acidic group such as a carboxylic group or a phenolic hydroxyl group, which renders an exposed area on a resist coating readily soluble in an alkaline developer.

As characteristics demanded of a photoacid generator for a chemically-amplified radiation-sensitive composition, superior transparency to radiation, high quantum yield, and capability of producing an acid which has strong acidity, high boiling point, and a suitable diffusion distance in a resist coating (hereinafter referred as diffusion length) can be given.

To ensure high acidity, high boiling point, and appropriate diffusion length, the structure of an anionic moiety in the ionic photoacid generator and the structure of a sulfonyl moiety in the nonionic photoacid generator comprising a sulfonyl structure or a sulfonic acid ester structure are important. When the photoacid generator has a trifluoromethanesulfonyl structure, for example, even though a sufficiently strong acid to ensure adequate resolution performance of a photoresist is generated, there is a drawback of a high mask dependency due to the low boiling point and long diffusion length of the generated acid. When the photoacid generator has a sulfonyl structure with a large organic group such as a 10-camphorsulfonyl structure, even though the mask dependency is low due to the high boiling point and short diffusion length of the generated acid, the resolution performance as a photoresist is insufficient due to the poor acidity.

On the other hand, photoacid generators having a perfluoroalkylsulfonyl structure such as perfluoro-n-octane sulfonic acid (PFOS) have been given attention in recent years due to the adequate acidity, boiling point of the acid, and diffusion length.

However, viewing these photoacid generators having a PFOS-type perfluoroalkylsulfonyl structure from an environmental aspect, they have low combustibility and their bioaccumulation is suspected. A report issued by the U.S. Environmental Protection Agency, entitled "Perfluorooctyl Sulfonates; Proposed Significant New Use Rule" proposes regulating the use of these compounds. Therefore, in the field of microfabrication, the development of a component functioning excellently as a photoacid generator without these drawbacks has been desired.

The object of the present invention is to provide a novel photoacid generator which, when used as a photoacid generator sensitive to radiations or heat, exhibits high transparency to deep ultraviolet rays such as a KrF excimer laser, ArF excimer laser, $F_2$ excimer laser, or EUV, and electron beams, exhibits comparatively high combustibility and no bioaccumulation, and produces an acid exhibiting high acidity, high boiling point, moderately short diffusion length in the resist coating, and low dependency to mask pattern density; a sulfonic acid generated from the photoacid generator; a sulfonic acid derivative useful as a raw material or intermediate for synthesizing the photoacid generator; and a positive-tone or negative-tone radiation-sensitive resin composition containing the photoacid generator.

SUMMARY OF THE INVENTION

First, the present invention provides an acid generator (hereinafter referred to as "acid generator (I)") which is a compound containing a structure represented by the following formula (I) (hereinafter referred to as "structure (I)"),

wherein R represents a monovalent organic group with a fluorine content of 50 wt % or less, a nitro group, a cyano group, or a hydrogen atom, and $Z^1$ and $Z^2$ are individually a fluorine atom or a linear or branched perfluoroalkyl group having 1–10 carbon atoms.

Second, the present invention provides a sulfonic acid represented by the following formula (I-a) (hereinafter referred to as "sulfonic acid (I-a)"),

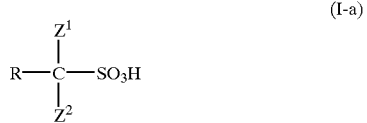
(I-a)

wherein R represents a monovalent organic group with a fluorine content of 50 wt % or less, a nitro group, a cyano group, or a hydrogen atom, and $Z^1$ and $Z^2$ are individually a fluorine atom or a linear or branched perfluoroalkyl group having 1–10 carbon atoms.

Third, the present invention provides a sulfonate represented by the following formula (1C) (hereinafter referred to as "sulfonate (1C)"),

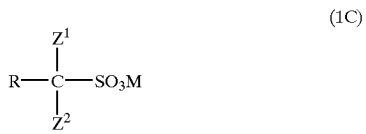
(1C)

wherein R represents a monovalent organic group with a fluorine content of 50 wt % or less, a nitro group, a cyano group, or a hydrogen atom, $Z^1$ and $Z^2$ are individually a fluorine atom or a linear or branched perfluoroalkyl group having 1–10 carbon atoms, and M is an Na, K, or Li.

Fourth, the present invention provides a sulfonyl halide compound represented by the following formula (4A) (hereinafter referred to as "sulfonyl halide compound (4A)"),

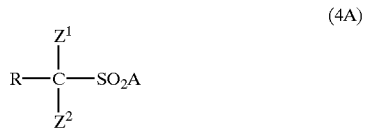
(4A)

wherein R represents a monovalent organic group with a fluorine content of 50 wt % or less, a nitro group, a cyano group, or a hydrogen atom, $Z^1$ and $Z^2$ are individually a fluorine atom or a linear or branched perfluoroalkyl group having 1–10 carbon atoms, and A is a halogen atom.

Fifth, the present invention provides a positive-tone radiation-sensitive resin composition comprising: (a) the acid generator (I) and (b) an alkali soluble or alkali low soluble resin comprising an acid-cleavable group that becomes soluble in alkali when the acid-cleavable group dissociates.

Sixth, the present invention provides a positive-tone radiation-sensitive resin composition comprising: (a) the acid generator (I), (b) an alkali soluble resin, and (c) an alkali solubility control agent.

Seventh, the present invention provides a negative-tone radiation-sensitive resin composition comprising: (a) the acid generator (I), (b) an alkali soluble resin, and (c) a compound that cross-links an alkali soluble resin in the presence of an acid.

Other objects, features and advantages of the invention will hereinafter become more readily apparent from the following description.

DETAILED DESCRIPTION OF THE INVENTION AND PREFERRED EMBODIMENTS

Figure 1:
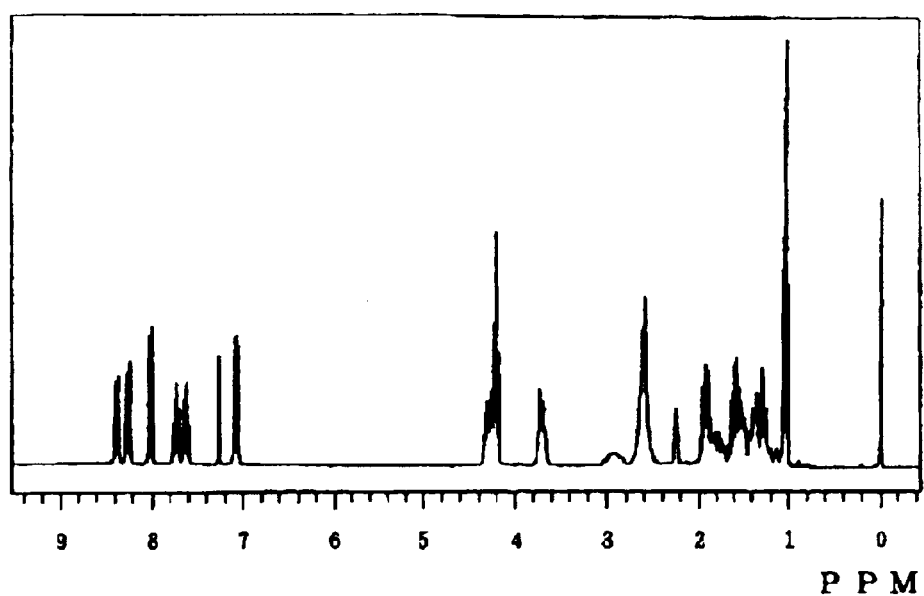
FIG. 1 shows the $^1$H-NMR analysis results of the acid generator (A-1).

The present invention will now be described in more detail by way of embodiments.

Acid Generator (I)

The acid generator (I) is a component that generates a sulfonic acid (I-a) when subjected to exposure or heating.

Due to the presence of a strong fluorine-containing electron withdrawing group in the α-position of the sulfonyl group in the structure (I), the acid generator (I) can produce an acid with high acidity such as sulfonic acid and the like. In addition, the acid produced is difficult to sublimate during a photolithography process due to a high boiling point and has a moderately short acid diffusion length in the resist coating. Furthermore, because the amount of fluorine in the produced acid is less than the amount of fluorine in perfluoroalkyl sulfonic acid, combustibility is comparatively high and accumulation in the human body is low.

As examples of the monovalent organic group with a fluorine content of 50 wt % or less for R in the formula (I), —$R^{11}$, —CO—$R^{11}$, —COO—$R^{11}$, —CON($R^{11}$)($R^{12}$), —S—$R^{11}$, —SO—$R^{11}$, —$SO_2$—$R^{11}$ (wherein $R^{11}$ and $R^{12}$ individually represent a substituted or unsubstituted linear, branched, or cyclic monovalent hydrocarbon group with 1–30 carbon atoms, a substituted or unsubstituted alyl group with 6–30 carbon atoms, or a substituted or unsubstituted monovalent heterocyclic organic group with 4–30 carbon atoms), and the like can be given.

As examples of the unsubstituted linear, branched, or cyclic monovalent hydrocarbon group having 1–30 carbon atoms for $R^{11}$ and $R^{12}$, a methyl group, ethyl group, n-propyl group, i-propyl group, n-butyl group, t-butyl group, n-pentyl group, i-pentyl group, n-hexyl group, i-hexyl group, n-octyl group, i-octyl group, 2-ethylhexyl group, n-dodecyl group, cyclopropyl group, cyclopentyl group, cyclohexyl group, groups with a norbornene structure, groups with a norbornane structure, groups with a tricyclodecane structure, groups with a tetracyclododecane structure, and the like can be given.

As examples of the substituents for the above hydrocarbon group, an aryl group, alkenyl group, an organic group-containing a hetero atom such as halogen, oxygen, nitrogen, sulfur, phosphorus, silicon and the like can be given.

As examples of the linear, branched, or cyclic monovalent hydrocarbon group having 1–30 carbon atoms substituted by the above substituent, a benzyl group, methoxymethyl group, methylthiomethyl group, ethoxymethyl group, phenoxymethyl group, methoxycarbonylmethyl group, ethoxycarbonylmethyl group, acetylmethyl group, fluoromethyl group, trifluoromethyl group, chloromethyl group, trichloromethyl group, 2-fluoropropyl group, trifluoroacetylmethyl group, trichloroacetylmethyl group, pentafluorobenzoylmethyl group, aminomethyl group, cyclohexylaminomethyl group, diphenylphosphino methyl group, trimethylsilylmethyl group, 2-phenylethyl group, 3-phenylpropyl group, and 2-aminoethyl group can be given.

As examples of the unsubstituted aryl group having 6–30 carbon atoms for $R^{11}$ and $R^{12}$, a phenyl group, 1-naphthyl group, 2-naphthyl group, 1-anthryl group, 1-phenanthryl group, and the like can be given.

As examples of the monovalent heterocyclic organic group having 4–30 carbon atoms for $R^{11}$ and $R^{12}$, a furyl group, thienyl group, pyranyl group, pyrrolyl group, thianthrenyl group, pyrazolyl group, iso-thiazolyl group, iso-oxazolyl group, pyrazinyl group, pyrimidinyl group, pyridazinyl group, and the like can be given.

As examples of the substituents for the above aryl group and monovalent heterocyclic organic group, an alkyl group, an organic group-containing a hetero atom such as halogen, oxygen, nitrogen, sulfur, phosphorus, silicon and the like can be given.

As examples of the substituted aryl group having 6–30 carbon atoms, a o-tolyl group, m-tolyl group, p-tolyl group, p-methoxyphenyl group, mesityl group, o-cumenyl group, 2,3-xylyl group, p-fluorophenyl group, p-trifluoromethylphenyl group, p-bromophenyl group, p-chlorophenyl group, p-iodophenyl group, and the like can be given.

As examples of the substituted monovalent heterocyclic organic group having 4–30 carbon atoms, a 2-bromofuryl group, 3-methoxythienyl group, and the like can be given.

As the group R in the formula (I), hydrocarbon groups such as a methyl group, ethyl group, n-butyl group, cyclohexyl group, phenyl group, 1-naphthyl group, and groups having a norbornene, norbornane, tricyclodecane structures, or tetracyclododecane structures, and the groups —S—$R^{11}$, —SO—$R^{11}$, and —SO$_2$—$R^{11}$, wherein $R^{11}$ is a hydrocarbon group such as a methyl group, ethyl group, n-butyl group, cyclohexyl group, or phenyl group, can be given, with groups having a norbornene, norbornane, or tetracyclododecane structure being particularly preferable.

As examples of the perfluoroalkyl group having 1–10 carbon atoms for $Z^1$ and $Z^2$ in the formula (I), a trifluoromethyl group, pentafluoroethyl group, heptafluoro-n-propyl group, nonafluoro-n-butyl group, and the like can be given.

As preferable structures for (I), the following formulas (I-1), (I-2), and (I-3) can be given, with (I-1) and (I-3) being particularly preferable.

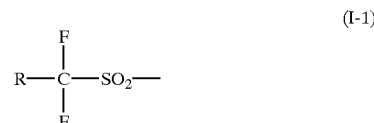

(I-1)

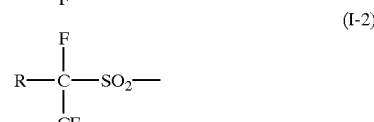

(I-2)

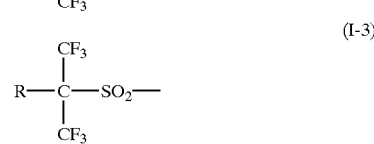

(I-3)

wherein R is the same as defined in formula (I).

As other preferable structures for (I), the following formulas (I-A) and (I-B) can be given.

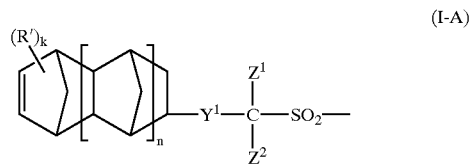

(I-A)

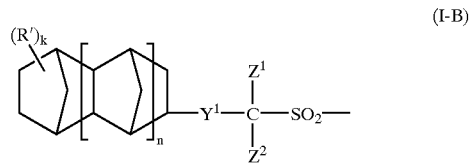

(I-B)

wherein $Z^1$ and $Z^2$ are the same as defined in formula (I), $Y^1$ represents a single-bond or divalent group, R' represents a monovalent substituent, k is an integer of 0 or more, and n is an integer from 0–5.

As examples of the divalent group for $Y^1$, —O—, —S—, carbonyl group, sulfinyl group, sulfonyl group, methylene group, 1,1-ethylene group, 1,2-ethylene group, propylene group, 1-methylpropylene group, 1-ethylpropylene group, trimethylene group, difluoromethylene group, tetrafluoro-1,2-ethylene group, 1,2-phenylene group, 1,3-phenylene group, 1,4-phenylene group, and the like can be given.

Among these divalent groups, a carbonyl group, methylene group, difluoromethylene group, and tetrafluoro-1,2-ethylene group are preferable.

As examples of the monovalent or divalent substituent for R', an oxo group (=O), hydroxyl group, carboxyl group, formyl group, a linear or branched alkyl group having 1–10 carbon atoms, a linear or branched vinylidene group having 1–10 carbon atoms, a monovalent cyclic organic group having 1–12 carbon atoms, an aryl group having 6–20 carbon atoms, a linear or branched alkoxyl group having 1–10 carbon atoms, an aryloxy group having 6–20 carbon atoms, a linear or branched alkylcarbonyl group having 2–10 carbon atoms, an arylcarbonyl group having 7–20 carbon atoms, a linear or branched alkoxycarbonyl group having 1–10 carbon atoms, an aryloxycarbonyl group having 7–20 carbon atoms, and the like can be given.

Given as examples of the linear or the branched alkyl group having 1–10 carbon atoms are a methyl group, ethyl group, n-propyl group, i-propyl group, n-butyl group, t-butyl group, n-pentyl group, n-hexyl group, n-heptyl group, n-octyl group, n-nonyl group, n-decyl group, and the like.

Given as examples of the linear or branched vinylidene group having 1–10 carbon atoms are a carbenyl group, 1,1-ethylidenyl group, propylidenyl group, 1-methylpropylidenyl group, 1-ethylpropylidenyl group, and the like.

Given as examples of the monovalent cyclic organic group having 1–12 carbon atoms are a cyclopentyl group, cyclohexyl group, adamantyl group, norbornyl group, campholoyl group, and the like.

Given as examples of the aryl group having 6–20 carbon atoms are a phenyl group, o-tolyl group, m-tolyl group, p-tolyl group, p-hydroxyphenyl group, 1-naphthyl group, 1-anthracenyl group, benzyl group, and the like.

Given as examples of the linear or branched alkoxyl group having 1–10 carbon atoms are a methoxy group, ethoxy group, n-propoxy group, i-propoxy group, n-butoxy group, t-butoxy group, and the like.

Given as examples of the aryloxy group having 6–20 carbon atoms are a phenoxy group, p-hydroxyphenoxy group, o-tolyloxy group, m-tolyloxy group, p-tolyloxy group, and the like.

Given as examples of the linear or branched alkylcarbonyl group having 2–10 carbon atoms are a methylcarbonyl group, ethylcarbonyl group, n-propylcarbonyl group, i-propylcarbonyl group, n-butylcarbonyl group, t-butylcarbonyl group, and the like.

Given as examples of the arylcarbonyl group having 7–20 carbon atoms are a phenylcarbonyl group, benzylcarbonyl group, and the like.

Given as examples of the linear or branched alkoxycarbonyl group having 2–10 carbon atoms are a methoxycarbonyl group, ethoxycarbonyl group, n-propoxycarbonyl group, i-propoxycarbonyl group, n-butoxycarbonyl group, t-butoxycarbonyl group, and the like.

Given as examples of the aryloxycarbonyl group having 7–20 carbon atoms are a phenoxycarbonyl group, benzyloxycarbonyl group, and the like. These substituents may have any substituents, for example, one or more of the above-mentioned substituents.

In the formulas (I-A) and (I-B), R' may bond with any of the carbon atoms that form the norbornene ring or norbornane ring. R' groups, if two or more are present, may be either the same or different.

In the formulas (I-A) and (I-B), $Y^1$ is preferably a single bond, methylene group, or carbonyl group, k is preferably 0, and n is preferably 0 or 1.

As examples of preferable structures for (I-A) and (I-B), the following formulas (A-1) to (A-12), (B-1) to (B-12) can be given.

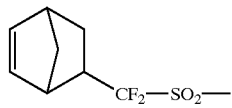

(A-1)

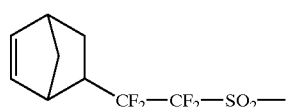

(A-2)

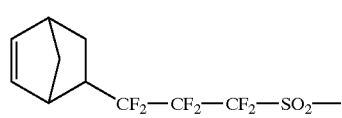

(A-3)

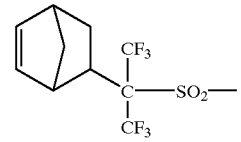

(A-4)

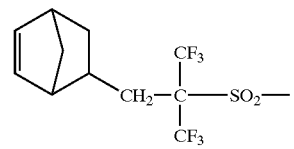

(A-5)

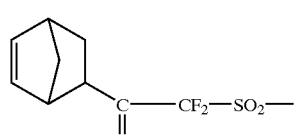

(A-6)

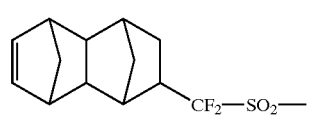

(A-7)

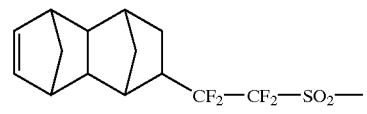

(A-8)

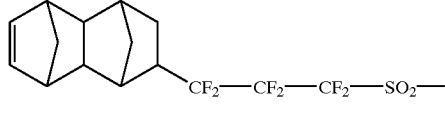

(A-9)

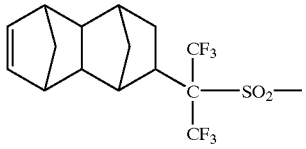

(A-10)

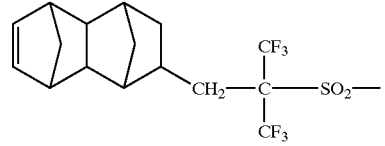

(A-11)

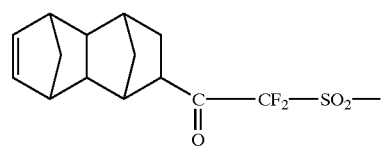

(A-12)

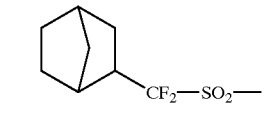

(B-1)

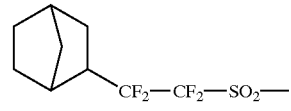

(B-2)

(B-3) 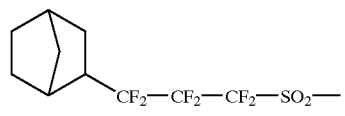

(B-4) 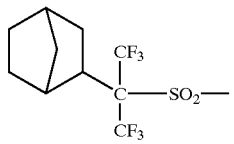

(B-5) 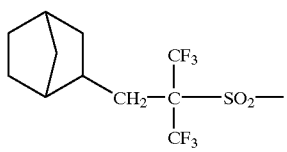

(B-6) 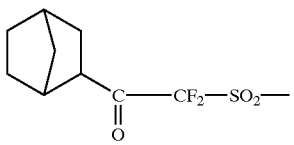

(B-7) 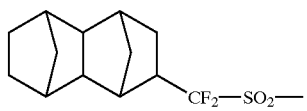

(B-8) 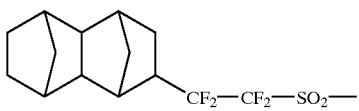

(B-9) 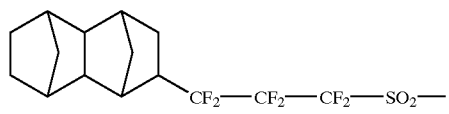

(B-10) 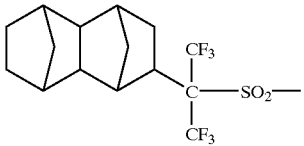

(B-11) 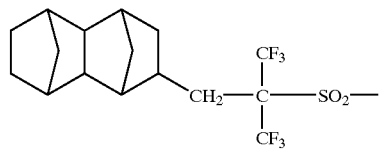

(B-12) 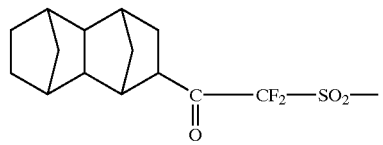

As an ionic compound for the acid generator (I), an onium sulfonate compound of the following formula (1) (hereinafter referred to as "onium sulfonate compound (1)") can be given. The onium sulfonate compound (1) is a compound wherein the sulfonyl group of the structure (I) binds with an oxygen anion to form a sulfonic acid anion.

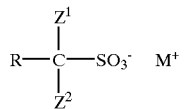 (1)

In the formula (1), R, $Z^1$, and $Z^2$ are the same as defined for the formula (I) and $M^+$ is a monovalent onium cation.

As examples of the monovalent onium cation for $M^+$, O, S, Se, N, P, As, Sb, Cl, Br, I, and the like can be given. Of these onium cations, S and I are preferable.

In the formula (1), as examples of a monovalent onium cation represented by $M^+$, the following formula (i) and (ii) can be given:

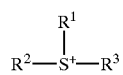 (i)

wherein $R^1$, $R^2$, and $R^3$ individually represents a substituted or unsubstituted, linear or branched alkyl group having 1–20 carbon atoms, a substituted or unsubstituted aryl group having 6–20 carbon atoms, or two or more of $R^1$, $R^2$, and $R^3$ form a ring together with the sulfur atom in the formula, and

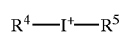 (ii)

wherein $R^4$ and $R^5$ individually represent a substituted or unsubstituted, linear or branched alkyl group having 1–20 carbon atoms, or a substituted or unsubstituted aryl group having 6–20 carbon atoms, or $R^4$ and $R^5$ form a ring together with the iodine atom in the formula.

The monovalent onium cation moiety of $M^+$ can be produced by a known method, for example, the method described in "J. V. Crivello, Advances in Polymer Science 62, 49, 1984".

As examples of preferable monovalent onium cations, the sulfonium cations shown by the following formulas (i-1) to (i-64) and the iodonium cations shown by the following formulas (ii-1) to (ii-39) can be given.

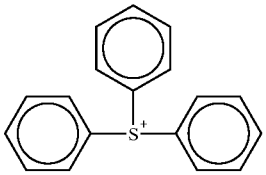 (i-1)

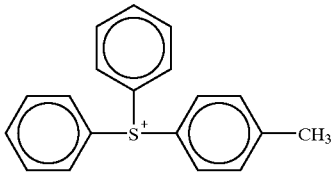 (i-2)

(i-3) 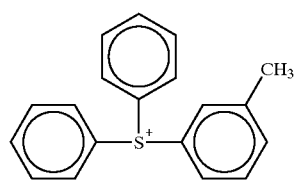
(i-4) 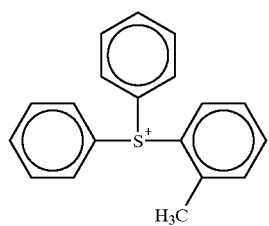
(i-5) 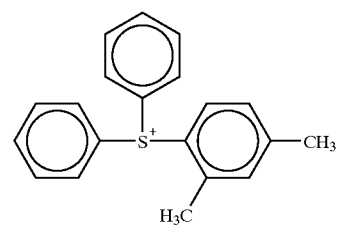
(i-6) 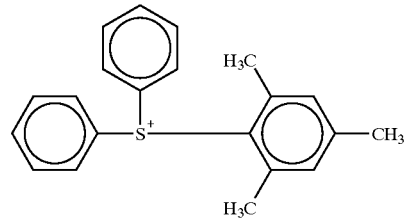
(i-7) 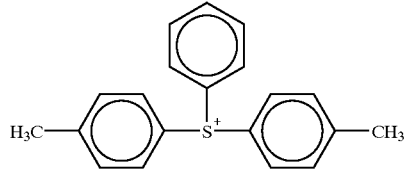
(i-8) 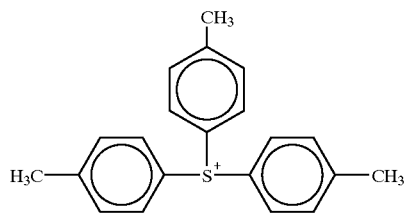
(i-9) 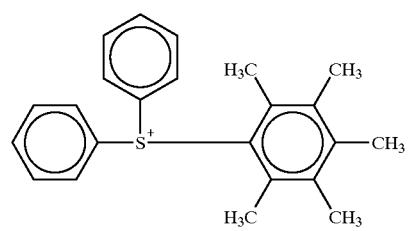
(i-10) 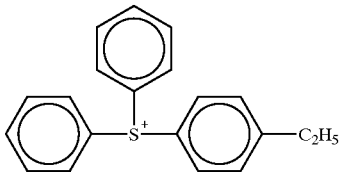
(i-11) 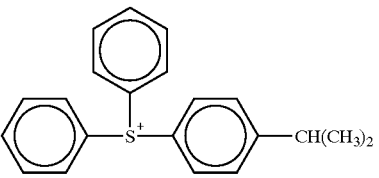
(i-12) 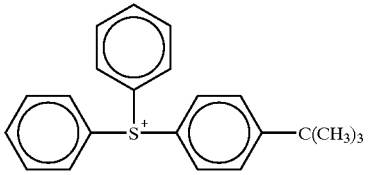
(i-13) 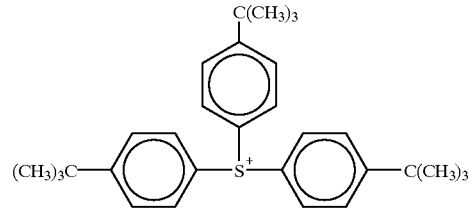
(i-14) 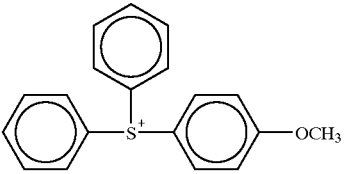
(i-15) 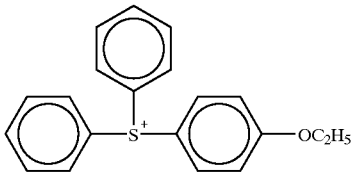
(i-16) 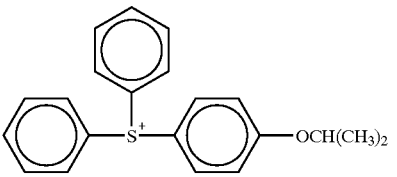
(i-17) 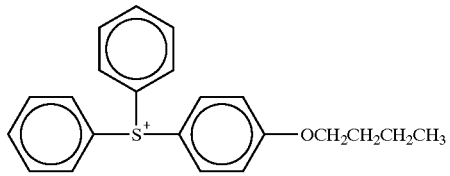

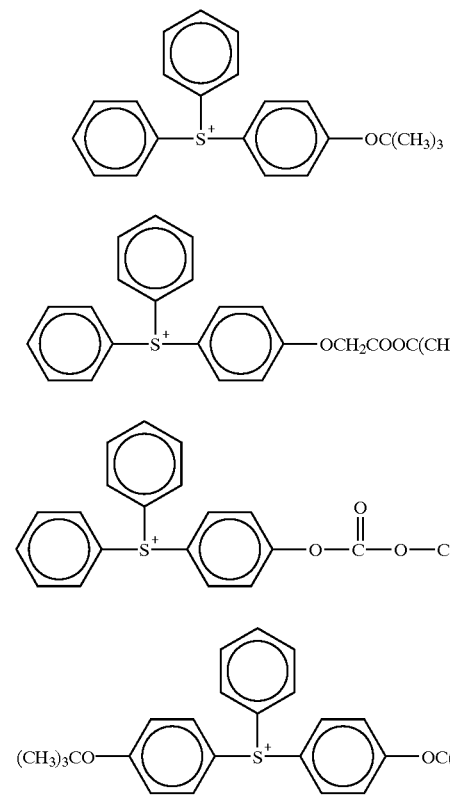
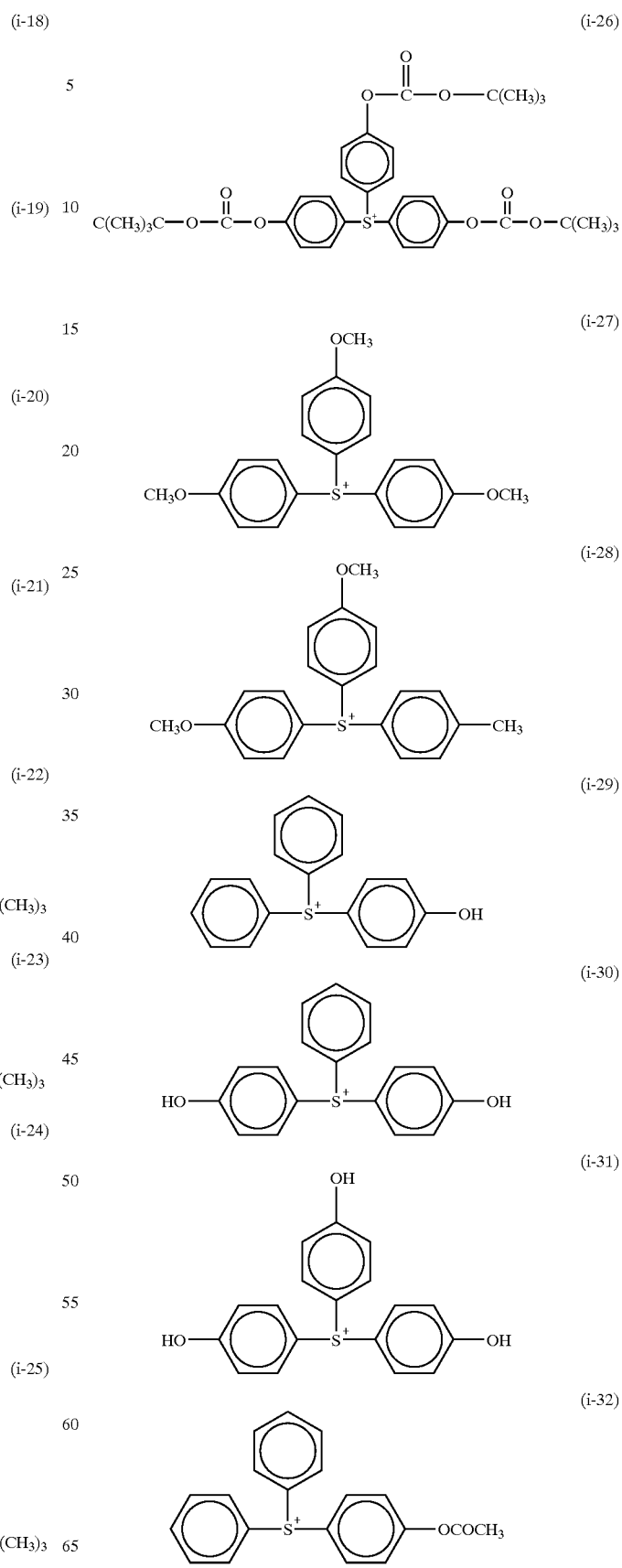

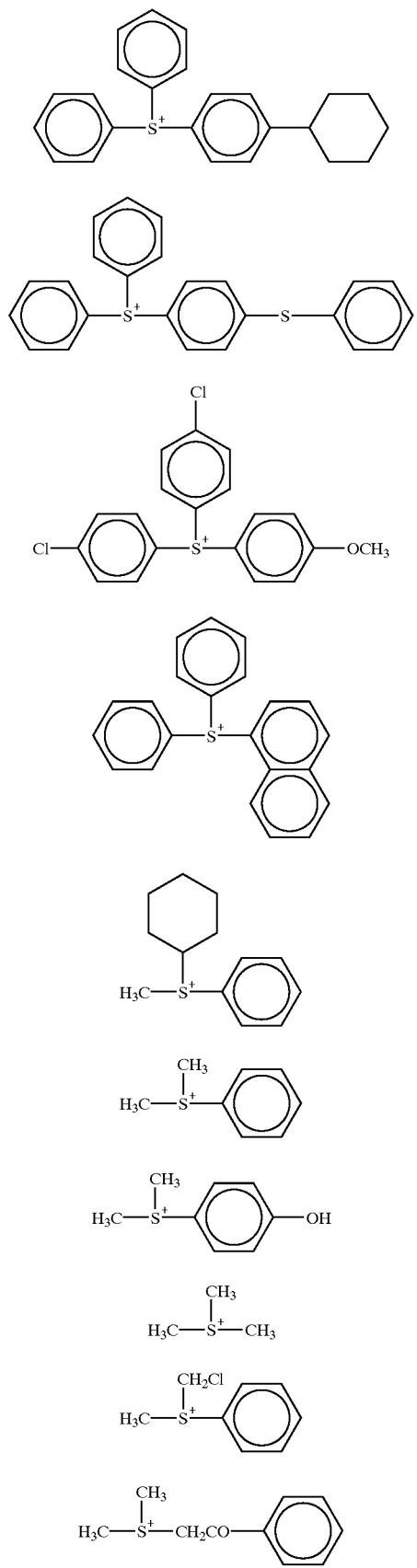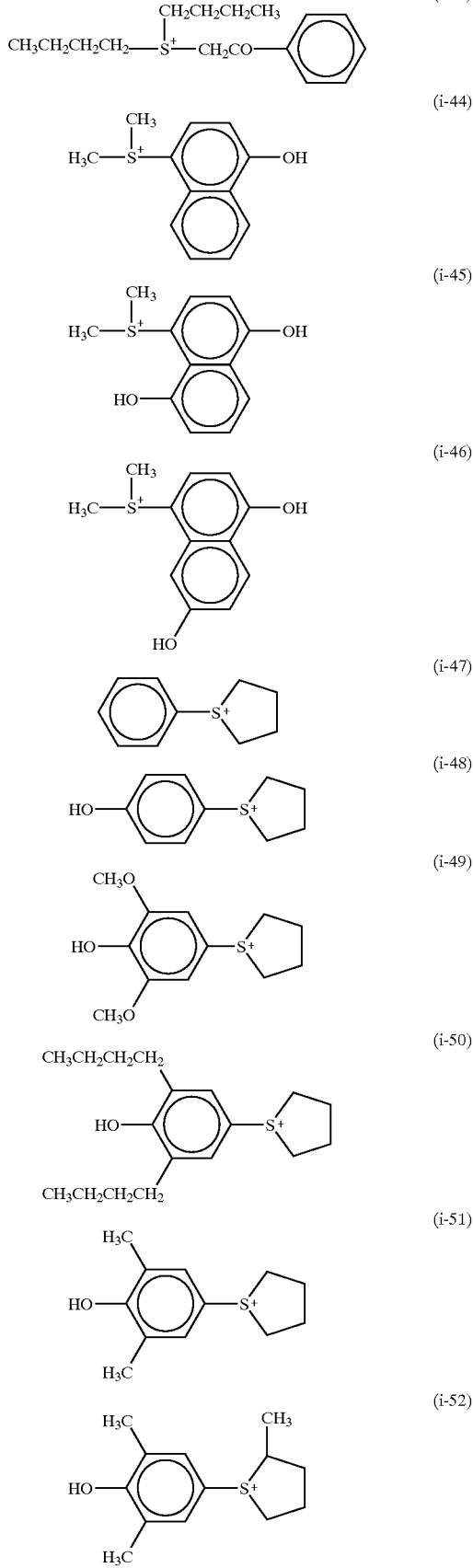

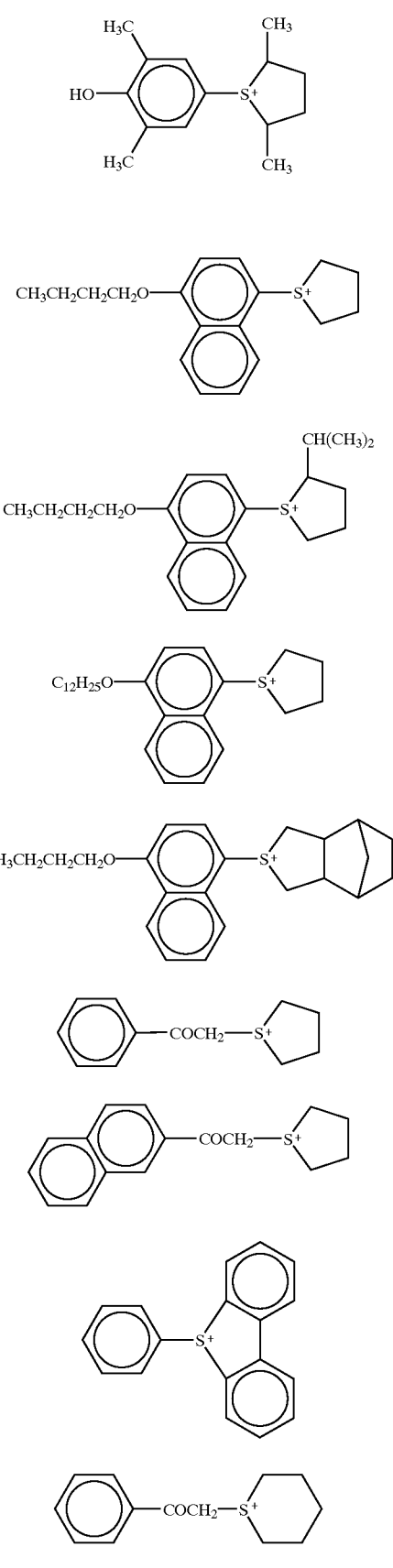
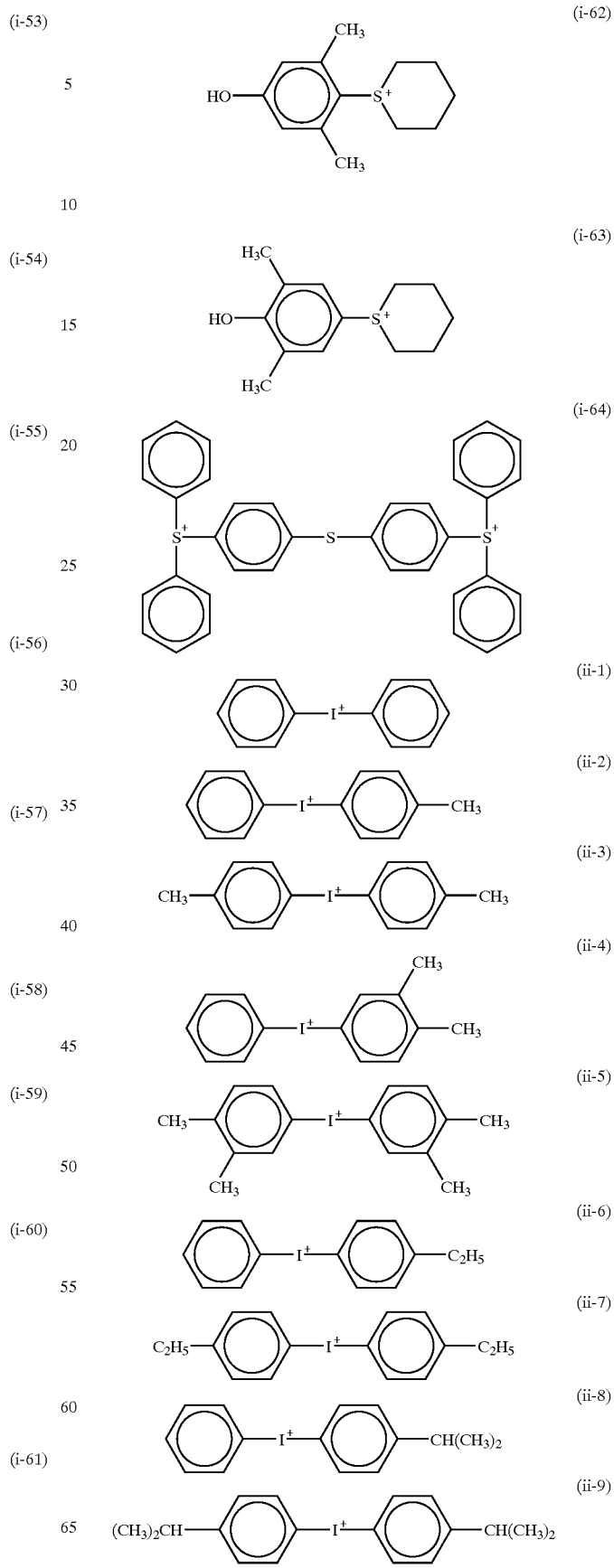

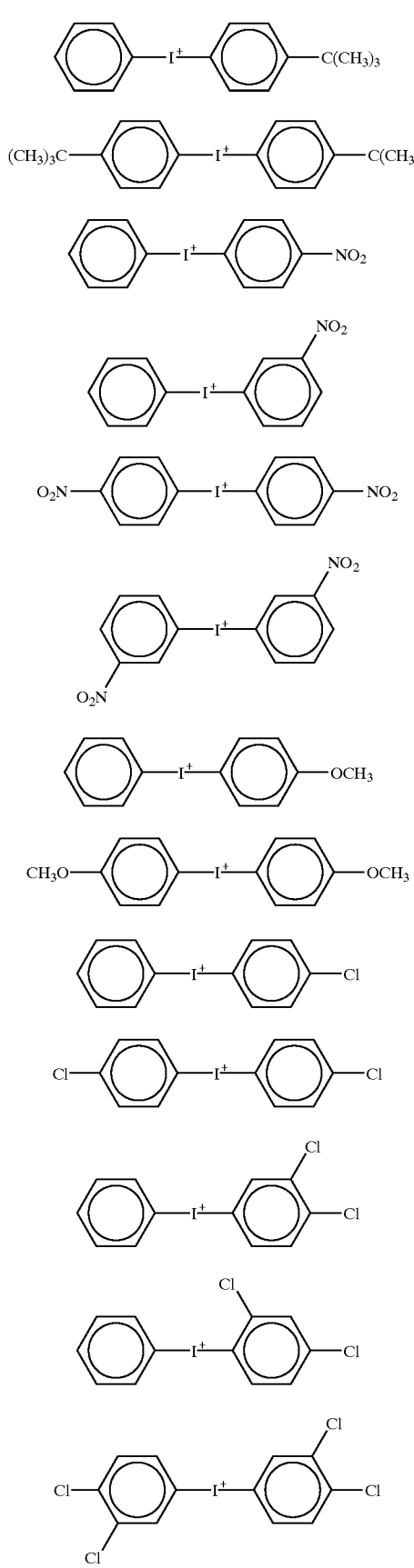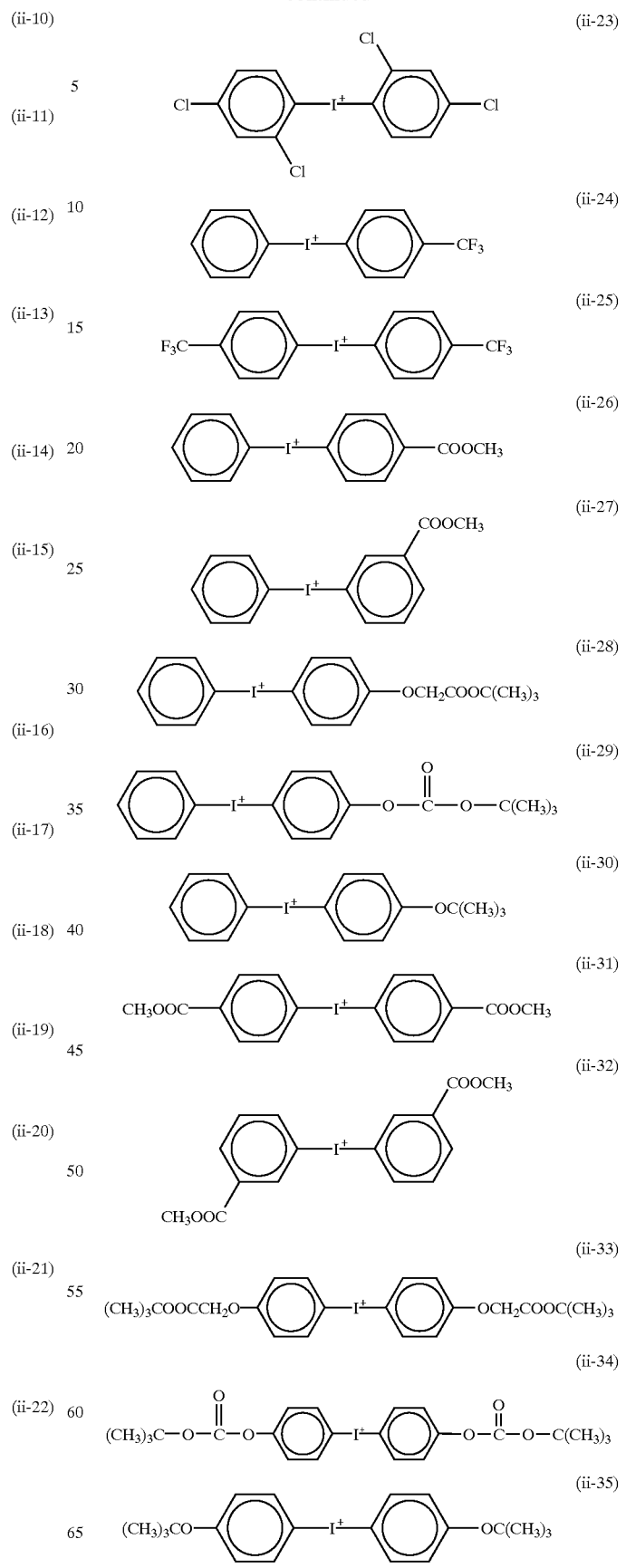

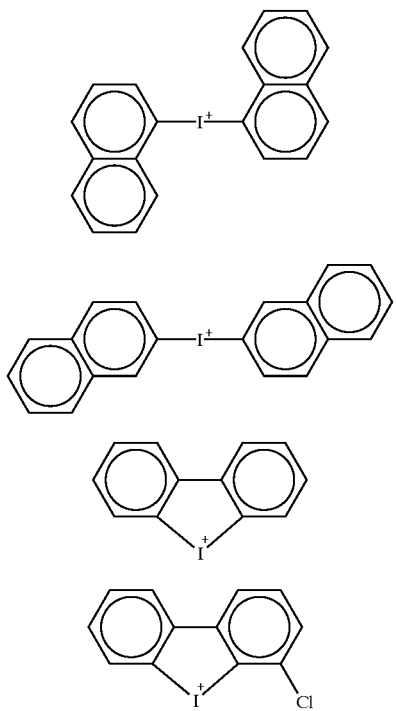

(ii-36)

(ii-37)

(ii-38)

(ii-39)

Of these monovalent onium cations, the sulfonium cations shown by the formulas (i-1), (i-2), (i-6), (i-8), (i-13), (i-19), (i-25), (i-27), (i-29), (i-51), and (i-54), and the iodonium cations shown by the formulas (ii-1) and (ii-11) are preferable.

As the preferable onium sulfonate compound (1), compounds of the following formulas (1-A) or (1-B) can be given.

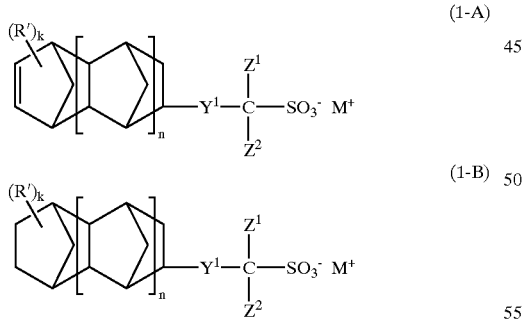

(1-A)

(1-B)

wherein $Z^1$ and $Z^2$ are as defined in formula (I), $Y^1$, R', k, and n are as defined in formulas (I-A) and (I-B), and $M^+$ is as defined in formula (1).

As a nonionic compound for the acid generator (I), an N-sulfonyloximide compound of the following formula (2) (hereinafter referred to as "N-sulfonyloximide compound (2)") can be given.

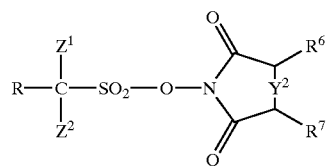

(2)

wherein R, $Z^1$, and $Z^2$ are as defined for formula (I), $R^6$ and $R^7$ individually represent a hydrogen atom or a substituted or unsubstituted monovalent organic group, or $R^6$ and $R^7$ may form a ring together with the carbon atoms to which either the group $R^6$ or $R^7$ combine, and $Y^2$ is a single bond, double bond, or a divalent organic group.

As preferable examples of the N-sulfonyloximide compound (2), compounds of the following formulas (2-A) or (2-B) can be given.

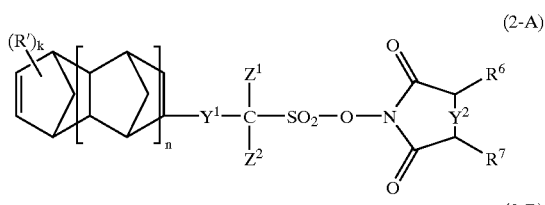

(2-A)

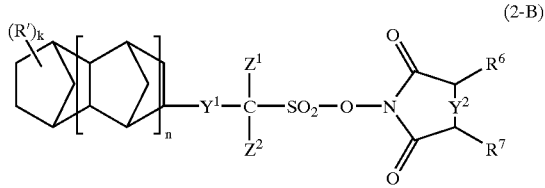

(2-B)

wherein $Z^1$ and $Z^2$ are as defined in formula (I), $Y^1$, R', k, and n are as defined in formulas (I-A) and (I-B), and $R^6$, $R^7$, and $Y^2$ are as defined in formula (2).

As preferable imide groups for bonding with the sulfonyloxy group ($SO_2$—O—) of formulas (2), (2-A), or (2-B), the groups of the following formulas (2-1) to (2-9) can be given.

(2-1)

(2-2)

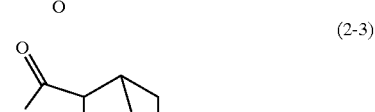

(2-3)

-continued

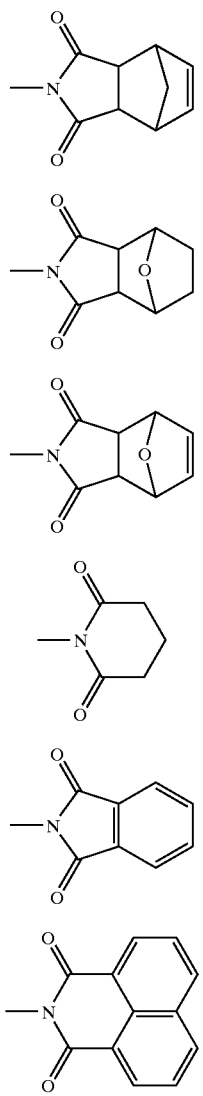

(2-4)

(2-5)

(2-6)

(2-7)

(2-8)

(2-9)

Of these imide groups, the groups of the formulas (2-1), (2-4), (2-8), or (2-9) are preferable.

The process of manufacturing the onium sulfonate compound (1) will now be described in detail.

The onium sulfonate compound (1) can be manufactured using known methods such as a method of D. D. Des Marteau (Inorganic Chemistry, Vol. 32, 5007, 1993) or a method of J. V. Crivello (Advances in Polymer Science 62, 49, 1984).

Specifically, as shown in the following reaction formula (1), the onium sulfonate compound (1) is manufactured by causing a precursor (1a) to react with sodium dithionite in the presence of an inorganic base to produce a sulfinate (1b), oxidizing the sulfinate (1b) using an oxidizing agent such as hydrogen peroxide or the like to produce a sulfonate (1c), and then conducting an ion-exchange reaction using a counter-ion-exchange precursor $M^+X^-$.

Reaction Formula (1)

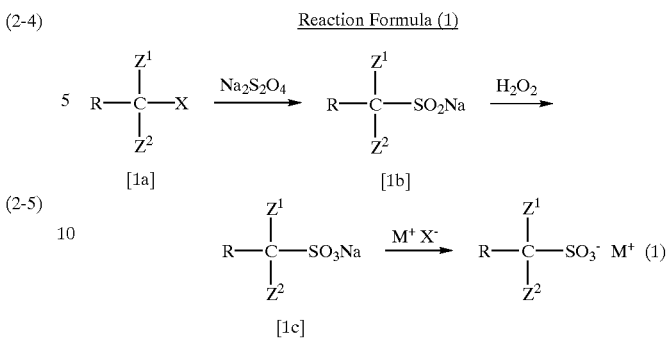

wherein X is a releasable monovalent group and $X^-$ is a monovalent anion.

As examples of the releasable monovalent group for X of the precursor (1a), in addition to halogen atoms such as a chlorine, bromine, and iodine, a methanesulfonate group, p-toluenesulfonate group, and the like can be given, with bromine and iodine atoms being preferable.

In the reaction of the precursor (1a) with sodium dithionite, the molar ratio of sodium dithionite to the precursor (1a) is usually 0.01–100 and preferably 1.0–10.

As examples of the inorganic base used in the reaction, lithium carbonate, sodium carbonate, potassium carbonate, lithium hydrogencarbonate, sodium hydrogencarbonate, potassium hydrogencarbonate, and the like can be given, with sodium hydrogencarbonate and potassium hydrogencarbonate being preferable.

The molar ratio of the inorganic base to the sodium dithionite is usually 1.0–10.0 and preferably 2.0–4.0.

This reaction is preferably carried out in a mixed solvent of an organic solvent and water. As the organic solvent, solvents having a high mutual solubility with water such as lower alcohols, tetrahydrofuran, N,N-dimethylformamide, N,N-dimethylacetoamide, acetonitrile, dimethylsulfoxide, and the like can be given as preferable examples, with N,N-dimethylacetoamide, acetonitrile, and dimethylsulfoxide being more preferable, and acetonitrile being particularly preferable.

The amount of the organic solvent used is usually 5–100 parts by weight, preferably 10–100 parts by weight, and particularly preferably 20–90 parts by weight for 100 parts by weight of the total amount of the organic solvent and water.

The reaction is carried out at a temperature of usually 40–200° C., and preferably 60–120° C. for usually 0.5–72 hours, and preferably 2–24 hours. If the reaction temperature used is higher than the boiling point of the organic solvent or water, a pressure vessel such as an autoclave is used.

As the oxidizer used in the oxidation reaction of the sulfinate (1b), in addition to hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmium oxide (VII), ruthenium oxide (VII), sodium hypochlorite, sodium chlorite, oxygen gas, ozone gas, and the like can be given, with hydrogen peroxide, methachloroperbenzoic acid, and t-butyl hydroperoxide being preferable.

The molar ratio of the oxidizer to the sulfinate (1b) is usually 1.0–10.0 and preferably 1.5–4.0.

Furthermore, a transition metal catalyst may be used together with the above-mentioned oxidizer.

As examples of the transition metal catalyst, disodium tungstate, iron (III) chloride, ruthenium (III) chloride, and selenium (IV) oxide can be given, with disodiumtungstate being preferable.

The molar ratio of the transition metal catalyst to the sulfinate (1b) is usually 0.001–2.0, preferably 0.01–1.0, and particularly preferably 0.03–0.5.

Furthermore, in addition to the above-mentioned oxidizer and transition metal catalyst, a buffer agent may be used for controlling the pH of the reaction solution.

As examples of the buffer agent, disodium hydrogenphosphate, sodium dihydrogenphosphate, dipotassium hydrogenphosphate, potassium dihydrogenphosphate, and the like can be given. The molar ratio of the buffer agent to the sulfinate (1b) is usually 0.01–2.0, preferably 0.03–1.0, and particularly preferably 0.05–0.5.

This reaction is usually carried out in a reaction solvent. As the reaction solvent, water, organic solvents such as lower alcohols, tetrahydrofuran, N,N-dimethylformamide, N,N-dimethylacetoamide, acetonitrile, dimethylsulfoxide, acetic acid, trifluoroacetic acid, and the like can be given as preferable examples, with methanol, N,N-dimethylacetoamide, acetonitrile, and dimethylsulfoxide being more preferable, and methanol being particularly preferable.

The amount of the reaction solvent used is usually 5–100 parts by weight, preferably 10–100 parts by weight, and particularly preferably 20–50 parts by weight for 100 parts by weight of the sulfinate (1b). If necessary, the above-mentioned organic solvent may be used with water. In this case, the amount of the organic solvent used is usually 5–100 parts by weight, preferably 10–100 parts by weight, and particularly preferably 20–90 parts by weight.

The reaction is carried out at a temperature of usually 0–100° C., preferably 5–60° C., and particularly preferably 5–40° C. for usually 0.5–72 hours, and preferably 2–24 hours.

A known method may be used for the ion exchange reaction of sulfonate (1c), for example the method described in "J. V. Crivello, Advances in Polymer Science 62, 49, 1984".

A method such as ion exchange chromatography may be used during the above-mentioned ion exchange reaction.

As examples of the monovalent anion for $X^-$ in the reaction formula (1), $F^-$, $Cl^-$, $Br^-$, $I^-$, perchlorate, hydrogen sulfurate, dihydrogen phosphorate, tetrafluorinated borate, aliphatic sulfonate, aromatic sulfonate, trifluoromethane sulfonate, fluorosulfonate, hexaflucrinated phosphorate, hexachlorinated antimonate, and the like can be given, with $Cl^-$, $Br^-$, hydrogen sulfurate, tetrafluorinated borate, and aliphatic sulfonate being preferable, and $Cl^-$, $Br^-$, and hydrogen sulfurate being particularly preferable. The molar ratio of the counter-ion exchange precursor to the sulfonate (1c) is usually 0.1–10.0, preferably 0.3–4.0, and particularly preferably 0.7–2.0.

This reaction is usually carried out in a reaction solvent. As the reaction solvent, water, organic solvents such as lower alcohols, tetrahydrofuran, N,N-dimethylformamide, N,N-dimethylacetoamide, acetonitrile, dimethylsulfoxide, and the like can be given as preferable examples, with water, methanol, N,N-dimethylacetoamide, acetonitrile, and dimethylsulfoxide being more preferable, and water being particularly preferable.

The amount of the reaction solvent used is usually 5–100 parts by weight, preferably 10–100 parts by weight, and particularly preferably 20–50 parts by weight for 100 parts by weight of the counter-ion exchange precursor. If necessary, water may be used with an organic solvent. In this case, the amount of the organic solvent used is usually 5–100 parts by weight, preferably 10–100 parts by weight, and particularly preferably 20–90 parts by weight for 100 parts by weight of the total amount of the organic solvent and water.

The reaction is usually carried out at a temperature of 0–80° C., and preferably 5–30° C. for usually 10 minutes to 6 hours, and preferably 30 minutes to 2 hours.

The onium sulfonate compound (1) obtained in this manner can also be purified by extraction using an organic solvent.

As the organic solvent used for purification, organic solvents that do not mix with water are preferable. Examples include esters such as ethyl acetate and n-butyl acetate, ethers such as diethyl ether, and halogenated alkyls such as methylene chloride and chloroform.

The onium sulfonate compound (1) shown by the formula (1-A) is obtained by the reaction of a norbornene derivative (2b), which is obtained by the Diels-Alder reaction of an ethylene derivative (2a) and a cyclopentadiene compound in accordance with the following reaction formula (2), or a norbornene derivative (3b), which is obtained by the Diels-Alder reaction of a cyclopentadiene compound and the norbornene derivative (2b) obtained in the reaction formula (3), in accordance with the reaction formula (1). The onium sulfonate compound (1) having three or more norbornene or norbornane rings can be produced by synthesizing a polycyclic norbornene derivative by repeatedly conducting the procedure shown in the reaction formula (3), then following the above-mentioned procedure.

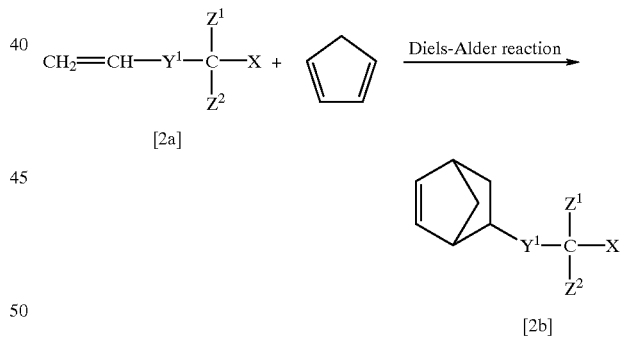

In the reaction formula (2), $Z^1$ and $Z^2$ are the same as defined in formula (I), $Y^1$ is the same as defined in formula (I-A) and (I-B), and X is the same as defined in reaction formula (1).

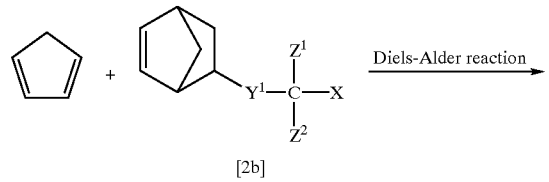

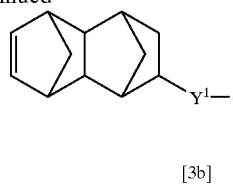

[3b]

In the reaction formula (3), $Z^1$ and $Z^2$ are the same as defined in formula (I), $Y^1$ is the same as defined in formula (I-A) and (I-B), and X is the same as defined in reaction formula (1).

The reaction formulas (2) and (3) will now be described in more detail. For the Diels-Alder reaction in reaction formulas (2) and (3), a known method such as that described in "Comprehensive Organic Synthesis, B. M. Trost & I. Fleming, Pergamon Press, New York, 1991, Vol. V, pp 315" may be used.

When conducting the Diels-Alder reaction, the molar ratio of the ethylene derivative (2a) to the cyclopentadiene compound and the molar ratio of the cyclopentadiene compound to the norbornene derivative (2b) are usually 0.01–100 and preferably 0.1–10.

This reaction may be conducted without the presence of a solvent, or in a reaction solvent such as toluene, xylene, N,N,-dimethylformamide, tetrahydrofuran, 1,2-dichloroethane, or the like.

The reaction is carried out at a temperature of usually 20–250° C., and preferably 80–180° C. for usually 0.5–24 hours, and preferably 4–12 hours. If the reaction temperature used is higher than the boiling point of the reaction raw materials or reaction solvent, a pressure vessel such as an autoclave is used.

The onium sulfonate compound (1) shown by the formula (1-B) can be produced by causing a norbornene derivative (for example the norbornene derivatives (2b) or (3b)) obtained in the manner shown by the reaction formulas (2) or (3)) to come in contact with hydrogen gas in a reaction solvent in the presence of a hydrogenation catalyst.

As examples of the hydrogenation catalyst, transition metal catalysts such as Raney nickel, palladium-carbon, platinum (IV) oxide, rhodium-carbon, rhodium-alumina, ruthenium-carbon, tris-(triphenylphosphine)chlororhodium (I), and the like can be given.

The weight ratio of the transition metal catalyst to each of the norbornene derivatives is usually 0.001–1 and preferably 0.01–0.2.

The pressure of the hydrogen gas during the hydrogenation reaction is usually 1–120 atm, preferably 1–100 atm, and particularly preferably 1–50 atm.

This reaction is usually carried out in a reaction solvent. As examples of the reaction solvent, organic solvents such as methanol, ethanol, ethyl acetate, toluene, xylene, tetrahydrofuran, 1,2-dichloroethane, and the like can be given.

The weight ratio of the reaction solvent to each of the norbornene derivatives is usually 1–100, preferably 5–100, and particularly preferably 10–80.

The reaction is carried out at a temperature of usually 20–200° C., preferably 20–150° C., and particularly preferably 20–100° C. for usually 0.5–24 hours, and preferably 4–12 hours. If the reaction temperature used is higher than the boiling point of the reaction raw materials or reaction solvent or if the pressure of the hydrogen gas used exceeds 1 atm, a pressure vessel such as an autoclave is used.

Next, the manufacturing method of N-sulfonyloxy imide compound (2) will be described in detail.

N-sulfonyloxyimide compound (2) is manufactured by, for example, using the sulfinate (1b) or sulfonate (1c) shown in the reaction formula (1).

Specifically, as shown in the following reaction formula (4), a sulfinate (1b) is converted into a sulfonyl halide compound (4A) such as a sulfonyl chloride (4a) using a halogenating agent such as chlorine gas. The sulfonyl halide compound (4A) is reacted with an N-hydroxyimide compound in a reaction solvent in the presence of a base catalyst to produce the N-sulfonyloxyimide compound (2).

Reaction Formula (4)

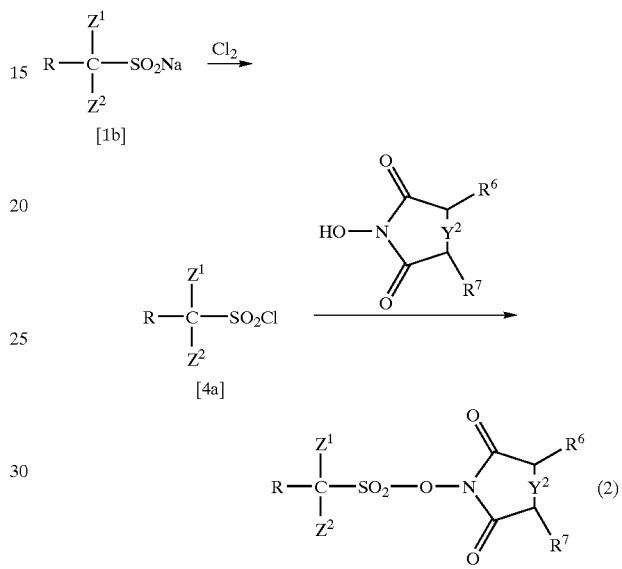

For the reaction of the sulfinate (1b) and the chlorinating agent, a known method such as that described in "D. D. DesMarteau, Inorganic Chemistry, Vol. 32, 5007, 1993" or the method described later in Synthesis Example may be used.

A method of bubbling chlorine gas into the reaction solution, for example, may be used for the reaction.

Usually, a great excess amount of the chlorinating agent for the amount of the sulfinate (1b) is used in the reaction.

This reaction is usually carried out in a reaction solvent. As the reaction solvent, water, organic solvents such as tetrahydrofuran, N,N-dimethylformamide, N,N-dimethylacetoamide, acetonitrile, dimethylsulfoxide, and the like can be given as preferable examples, with water, methanol, N,N-dimethylacetoamide, acetonitrile, and dimethylsulfoxide being more preferable, and water being particularly preferable.

The amount of the reaction solvent used is usually 5–100 parts by weight, preferably 10–100 parts by weight, and particularly preferably 20–50 parts by weight for 100 parts by weight of the sulfinate (1b). If necessary, the above-mentioned organic solvent may be used together with water In this case, the amount of the organic solvent used is usually 5–100 parts by weight, preferably 10–100 parts by weight, and particularly preferably 20–90 parts by weight for 100 parts by weight of the total amount of water and the organic solvent.

The reaction is carried out at a temperature of usually 0–100° C., preferably 5–60° C., and particularly preferably 5–40° C. for usually 5 minutes to 12 hours, and preferably 10 minutes to 5 hours.

In the reaction of sulfonyl chloride (4a) and N-hydroxyimide compound, the molar ratio of N-hydroxyimide compound to sulfonyl chloride (4a) is usually 0.1–10.0, preferably 0.3–5.0, and particularly preferably 0.5–2.0.

This reaction is usually carried out in a reaction solvent. As the reaction solvent, acetonitrile, dimethyl formamide, tetrahydrofuran, dimethyl sulfoxide, methylene chloride, methylene bromide, and chloroform can be given as preferable examples, with acetonitrile, tetrahydrofuran, and methylene chloride being particularly preferable.

The amount of the reaction solvent used is usually 5–100 parts by weight, preferably 10–100 parts by weight, and particularly preferably 20–50 parts by weight for 100 parts by weight of the sulfonyl chloride (4a).

As the base catalyst, triethylamine, pyridine, N,N-diisopropylethylamine, 2,6-lutidine, N,N-diethylaniline, 4-dimethylaminopyridine, and diazabicycloundecene can be given as preferable examples, with triethylamine and 4-dimethylaminopyridine being particularly preferable.

The molar ratio of the base catalyst to the sulfonyl chloride (4a) is usually 1.0–10.0, preferably 1.5–5.0, and particularly preferably 1.5–3.0.

The reaction is usually carried out at a temperature of 0–80° C., and preferably 5–30° C. for usually 5 minutes to 6 hours, and preferably 10 minutes to 2 hours.

The N-sulfonyloxyimide compound (2) of the formulas (2-A) or (2-B) can be manufactured by preparing a sulfinate (1b) from a norbornene derivative such as a norbornene derivative (2b) or (3b) or the hydrogenation derivative thereof, previously described relating to the method of manufacturing the onium sulfonate compound (1) of the formulas (1-A) or (1-B), using the procedure shown in the reaction formula (1), then following the procedure shown in the reaction formula (4).

Moreover, as examples of the acid generator (I) other than the onium sulfonate compound (1) and the N-sulfonyloxyimide compound (2), a sulfone compound, sulfonate compound, disulfonyl diazomethane compound, disulfonyl methane compound, oxime sulfonate compound, hydrazinesulfonate compound, and the like can be given.

These compounds will now be discussed.

As examples of the sulfone compounds, β-ketosulfone, β-sulfonylsulfone, and α-diazo compounds of these compounds can be given.

Specific examples of the sulfone compounds include the compounds of the following formulas (3-1) and (3-2):

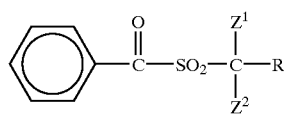

(3-1)

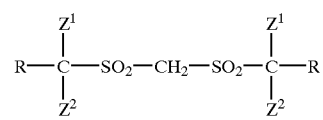

(3-2)

wherein R, $Z^1$, and $Z^2$ are the same as defined in the formula (I), the two R, $Z^1$, and $Z^2$ groups in the formula (3-2) being either identical or different.

As examples of the sulfonate compounds, alkyl sulfonate, haloalkyl sulfonate, aryl sulfonate, and imino sulfonate can be given.

Specific examples of the sulfonate compounds include the compound of the following formula (4):

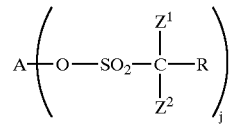

(4)

wherein R, $Z^1$, and $Z^2$ are the same as defined in the formula (I), when two or more R, $Z^1$, and $Z^2$ groups are present, such groups may be either identical or different; A represents a j-valent organic residue originating from pyrogallol, α-methylol benzoin, and the like; and j is an integer from 1–3.

As examples of the disulfonyl diazomethane compounds, compounds of the following formula (5) can be given:

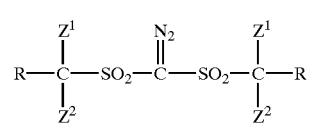

(5)

wherein R, $Z^1$, and $Z^2$ are the same as defined in the formula (I), the two R, $Z^1$, and $Z^2$ groups being either identical or different.

As examples of the disulfonyl methane compounds, compounds of the following formula (6) can be given:

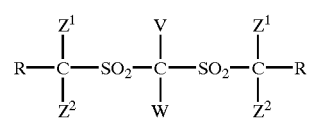

(6)

wherein R, $Z^1$, and $Z^2$ are the same as defined in the formula (I), the two R, $Z^1$, and $Z^2$ groups being either identical or different; V and W individually represent an aryl group, a hydrogen atom, a linear or branched monovalent aliphatic hydrocarbon group, or a monovalent organic group having a hetero atom, provided that at least one of V or W is an aryl group, or V and W may combine to form a monocyclic or polycyclic structure containing at least one unsaturated bond, or a group of the following formula (7):

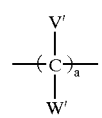

(7)

wherein V' and W' individually represent a hydrogen atom, halogen atom, alkyl group, cycloalkyl group, aryl group, or aralkyl group, or V' and W', each combining with the same or different carbon atoms, combine to form a monocyclic carbon structure, and a is an integer from 2 to 10.

As examples of oxime sulfonate compounds, compounds of the following formulas (8-1) or (8-2) can be given:

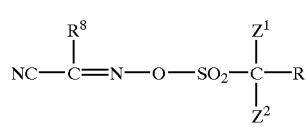

(8-1)

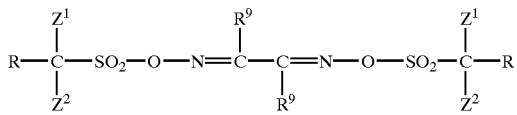

(8-2)

wherein R, $Z^1$, and $Z^2$ are the same as defined in the formula (I), the two R, $Z^1$, and $Z^2$ groups in the formula (8-2) being either identical or different, and $R^8$ and $R^9$ individually represent a monovalent organic group.

As examples of hydrazine sulfonate compounds, compounds of the following formulas (9-1) or (9-2) can be given:

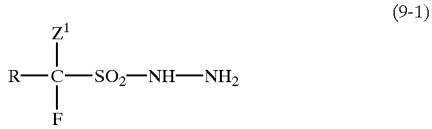

(9-1)

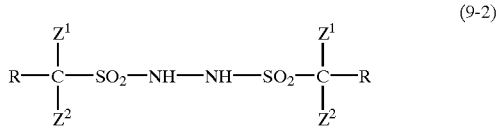

(9-2)

wherein R, $Z^1$, and $Z^2$ are the same as defined in the formula (I), the two R, $Z^1$, and $Z^2$ groups in the formula (9-2) being either identical or different.

Positive-Tone Radiation-Sensitive Resin Composition

The positive-tone radiation-sensitive resin composition of the present invention is a composition comprising either: (i) (a) the acid generator (I) and (b) an acid-cleavable group-containing resin which is insoluble or scarcely soluble in alkali and becomes alkali soluble when the acid-cleavable group dissociates (hereinafter referred to as "acid-cleavable group-containing resin") (hereinafter referred to as "positive-tone radiation-sensitive resin composition (i)"); or (ii) (a) the acid generator (I), (c) an alkali-soluble resin, and (d) an alkali-soluble control agent (hereinafter referred to as "positive-tone radiation-sensitive resin composition (ii)").

As the acid generator (I) used in these positive-tone radiation-sensitive resin compositions, acid generators having heat and chemical stability are preferable.

The positive-tone radiation-sensitive resin composition (i) and positive-tone radiation-sensitive resin composition (ii) of the present invention will now be described.

In the positive-tone radiation-sensitive resin composition (i) and positive-tone radiation-sensitive resin composition (ii), the acid generator (I) may be used either individually or in combination of two or more.

The amount of the acid generator (I) used in the positive-tone radiation-sensitive resin composition (i) and positive-tone radiation-sensitive resin composition (ii) varies depending on the type of the acid generator (I) or other acid generators which are optionally used. Such an amount is usually 0.1–20 parts by weight, preferably 0.1–15 parts by weight, and particularly preferably 0.2–12 parts by weight for 100 parts by weight of the acid-cleavable group-containing resin or alkali-soluble resin. If the amount of acid generator (I) is less than 0.1 part by weight, it is difficult to achieve the intended effect of the present invention; if more than 20 parts by weight, transparency to radiation, pattern shape, and heat resistance tends to decrease.

Acid-Cleavable Group-Containing Resin

As the acid-cleavable group-containing resin for the positive-tone radiation-sensitive resin composition (i), a resin, insoluble or scarcely soluble in alkali by itself and becomes alkali-soluble when the acid-cleavable group dissociates, obtainable from a resin containing one or more oxygen containing functional groups such as a phenolic hydroxyl group, alcoholic hydroxyl group, or carboxyl group by substituting the hydrogen atoms in the oxygen containing functional groups with one or more acid-cleavable groups through disassociation in the presence of an acid can be given.

If 50% or more of the initial film thickness of a resist coating remains after development when a resist coating made only from the acid-cleavable group-containing resin is developed under the same alkaline development conditions employed for forming a resist pattern using a resist coating formed from a positive-tone radiation-sensitive resin composition comprising the acid-cleavable group-containing resin, such a characteristic of the acid-cleavable group-containing resin is referred to as "insoluble or scarcely soluble in alkali" in the present invention.

As examples of the acid-cleavable group in the acid-cleavable group-containing resin, a substituted methyl group, 1-substituted ethyl group, 1-substituted n-propyl group, 1-branched alkyl group, silyl group, germyl group, alkoxycarbonyl group, acyl group, cyclic acid-cleavable group, and the like can be given.

As examples of a substituted methyl group, a methoxymethyl group, methylthiomethyl group, ethoxymethyl group, ethylthiomethyl group, methoxyethoxymethyl group, benzyloxymethyl group, benzylthiomethyl group, phenacylgroup, 4-bromophenacyl group, 4-methoxyphenacyl group, 4-methylthiophenacyl group, α-methylphenacyl group, cyclopropylmethyl group, benzyl group, diphenylmethyl group, triphenylmethyl group, adamantylmethyl group, 4-bromobenzyl group, 4-nitrobenzyl group, 4-methoxybenzyl group, 4-methylthiobenzyl group, 4-ethoxybenzyl group, 4-ethylthiobenzyl group, piperonyl group, methoxycarbonylmethyl group, ethoxycarbonylmethyl group, n-propoxycarbonylmethyl group, i-propoxycarbonylmethyl group, n-butoxycarbonylmethyl group, t-butoxycarbonylmethyl group, and the like can be given.

As examples of a 1-substituted ethyl group, a 1-methoxyethyl group, 1-methylthioethyl group, 1,1-dimethoxyethyl group, 1-ethoxyethyl group, 1-ethylthioethyl group, 1,1-diethoxyethyl group, 1-phenoxyethyl group, 1-phenylthioethyl group, 1,1-diphenoxyethyl group, 1-benzyloxyethyl group, 1-benzylthioethyl group, 1-cyclopropyloxyethyl group, 1-cyclohexyloxyethyl group, 1-phenylethyl group, 1,1-diphenylethyl group, 1-methoxycarbonylethyl group, 1-ethoxycarbonylethyl group, 1-n-propoxycarbonylethyl group, 1-i-propoxycarbonylethyl group, 1-n-butoxycarbonylethyl group, 1-t-butoxycarbonylethyl group, 1-cyclohexyloxycarbonylethyl group and the like can be given.

As examples of 1-substituted n-propyl group, a 1-methoxy-n-propyl group, 1-ethoxy-n-propyl group, and the like can be given.

As examples of 1-branched alkyl group, an i-propyl group, sec-butyl group, t-butyl group, 1,1-dimethylpropyl group, 1-methylbutyl group, 1,1-dimethylbutyl group, and the like can be given.

As examples of the silyl groups, a trimethylsilyl group, ethyldimethylsilyl group, methyldiethylsilyl group, triethylsilyl group, i-propyldimethylsilyl group, methyldi-i-propylsilyl group, tri-i-propylsilyl group, t-butyldimethylsilyl group, methyldi-t-butylsilyl group, trit-butylsilyl group, phenyldimethylsilyl group, methyldiphenylsilyl group, triphenylsilyl group, and the like can be given.

As examples of the germyl groups, a trimethylgermyl group, ethyldimethylgermyl group, methyldiethylgermyl group, triethylgermyl group, i-propyldimethylgermyl group, methyldi-i-propylgermyl group, tri-i-propylgermyl group, t-butyldimethylgermyl group, methyldi-t-butylgermyl group, tri-t-butylgermyl group, phenyldimethylgermyl group, methyldiphenylgermyl group, triphenylgermyl group, and the like can be given.

As examples of the alkoxycarbonyl groups, a methoxycarbonyl group, ethoxycarbonyl group, i-propoxycarbonyl group, t-butoxycarbonyl group, and the like can be given.

As examples of the acyl groups, an acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, scucinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluenesulfonyl group, mesyl group, and the like can be given.

As examples of the cyclic acid-cleavable group, cyclopropyl group, cyclopentyl group, cyclohexyl group, 4-t-butyl cyclohexyl group, 4-methoxy cyclohexyl group, cyclohexenyl group, norbornyl group, isobornyl group, tricyclodecanyl group, adamantyl group, tetrahydropyranyl group, tetrahydrofuranyl group, tetrahydrothiopyranyl group, tetrahydrothiofuranyl group, 3-bromotetrahydropyranyl group, 4-methoxy tetrahydropyranyl group, 4-methoxy tetrahydrothiopyranyl group, 3-tetrahydrothiophene-1,1-dioxide group, methyl adamantyl group, ethyl adamantyl group, methyl tricyclodecanyl group, ethyl tricyclodecanyl group, methyl cyclopentyl group, ethyl cyclopentyl group, methyl cyclohexyl group, ethyl cyclohexyl group, and —C($R^{10}$)$_3$ group (wherein the $R^{10}$ independently represents a linear or branched alkyl group having 1–4 carbon atoms or a substituted or unsubstituted monovalent alicyclic hydrocarbon group having 4–20 carbon atoms, provided that at least one of the groups $R^{10}$ is a substituted or unsubstituted monovalent alicyclic hydrocarbon group having 4–20 carbon atoms, or any two of the groups $R^{10}$ form, in combination and together with the carbon atoms to which the two $R^{10}$ groups bond, a substituted or unsubstituted divalent alicyclic hydrocarbon group having 4–20 carbon atoms, with the remaining $R^{10}$ being a linear or branched alkyl group having 1–4 carbon atoms or a substituted or unsubstituted monovalent alicyclic hydrocarbon group having 4–20 carbon atoms) can be given.

Of these acid-cleavable groups, the benzyl group, t-butoxycarbonylmethyl group, 1-methoxyethyl group, 1-ethoxyethyl group, 1-cyclohexyloxyethyl group, 1-ethoxy-n-propyl group, t-butyl group, 1,1-dimethylpropyl group, trimethylsilyl group, t-butoxycarbonyl group, 4-t-butyl cyclohexyl group, isobornyl group, tricyclodecanyl group, tetrahydropyranyl group, tetrahydrofuranyl group, tetrahydrothiopyranyl group, tetrahydrothiofuranyl group, methyl adamantyl group, ethyl adamantyl group, methyl tricyclodecanyl group, ethyl tricyclodecanyl group, methyl cyclopentyl group, ethyl cyclopentyl group, methyl cyclohexyl group, ethyl cyclohexyl group, —C($R^{10}$)$_3$ group, and the like are preferable.

As specific examples of the —C($R^{10}$)$_3$ group, 1-(2-norbornyl)-1-methylethyl group, 1-(5-hydroxy-2-norbornyl)-1-methylethyl group, 1-(3-tetracyclodecanyl)-1-methylethyl group, 1-(8-hydroxy-3-tetracyclodecanyl)-1-methylethyl group, 1-(1-adamantyl)-1-methylethyl group, 1-(3-hydroxy-1-adamantyl)-1-methylethyl group, 2-methyl-2-norbornyl group, 2-methyl-5-hydroxy-2-norbornyl group, 3-methyl-3-tetracyclodecanyl group, 3-methyl-8-hydroxy-3-tetracyclodecanyl group, 2-methyl-2-adamantyl group, 2-methyl-7-hydroxy-2-adamantyl group, and the like can be given.

The amount of the acid-cleavable group introduced into the acid-cleavable group-containing resin (the amount of the number of acid-cleavable groups in the total number of oxygen containing functional groups and acid-cleavable groups in the acid-cleavable group-containing resin) is preferably 10–100%, and still more preferably 15–100%, although the amount varies depending on types of acid-cleavable group and the alkali-soluble resin into which the acid-cleavable group is introduced.

The polystyrene-reduced weight average molecular weight (hereinafter referred to as "Mw") of the acid-cleavable group-containing resin (A) determined by gel permeation chromatography is preferably 1,000–500,000, more preferably 1,000–300,000, and particularly preferably 3,000–300,000.

The ratio of Mw to the polystyrene-reduced number average molecular weight (hereinafter referred to as "Mn") determined by gel permeation chromatography (Mw/Mn) of the acid-cleavable group-containing resin is usually 1–10, and preferably 1–5.

These acid-cleavable group-containing resins may be used either individually or in combination of two or more.

As a suitable acid-cleavable group-containing resin for the positive-tone radiation-sensitive resin composition (i) using a KrF excimer laser, a resin insoluble or scarcely soluble in alkali comprising one or more recurring units of the following formula (10) and one or more recurring units containing an acid-cleavable group is preferable (this resin is hereinafter referred to as "resin (B1)"). The resin (B1) is also suitable for use in a positive-tone radiation-sensitive resin composition (i) using an ArF excimer laser, $F_2$ excimer laser, electron beams, or the like.

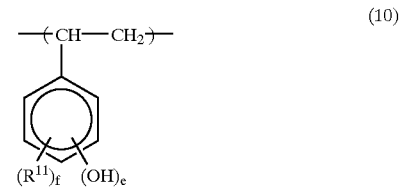

(10)

wherein $R^{11}$ represents a hydrogen atom or a monovalent organic group, and e and f are integers from 1–3, satisfying the formula (e+f)≦5.

As examples of the recurring units of the formula (10), units obtainable by cleavage of a polymerizable unsaturated bond of a compound such as 4-hydroxystyrene, 3-hydroxystyrene, 2-hydroxystyrene, 4-hydroxy-α-methylstyrene, 3-methyl-4-hydroxystyrene, 2-methyl-4-hydroxystyrene, 2-methyl-3-hydroxystyrene, 4-methyl-3-hydroxystyrene, 5-methyl-3-hydroxystyrene, 3,4-dihydroxystyrene, and 2,4,6-trihydroxystyrene can be given.

Of these recurring units, units obtainable by cleavage of a polymerizable unsaturated bond of 4-hydroxystyrene, 3-hydroxystyrene, 2-hydroxystyrene, or 4-hydroxy-α-methylstyrene are preferable.

As the recurring units having the above-mentioned acid-cleavable group, recurring units having one or more types of acid functional group such as a phenolic hydroxyl group and carboxyl group can be given, with the recurring units shown by the formula (10) or recurring units obtained by cleavage of the polymerizable unsaturated bond of a (meth)acrylic acid wherein the hydrogen atom of a phenolic hydroxyl group or carboxyl group is replaced by the above-mentioned acid-cleavable groups being preferable. Particularly preferable groups are recurring units obtained by the cleavage of a polymerizable unsaturated bond of a 4-t-butoxystyrene, 4-t-butoxycarbonyloxystyrene, 4-t-butoxycarbonylmethyloxystyrene, 4-tetrahydrofuranyloxystyrene, 4-tetrahydropyranyloxystyrene, 2-ethoxyethoxystyrene, 2-cyclopentyloxyethoxystyrene, 2-cyclohexyloxyethoxystyrene, t-butyl(meth)acrylate, methyladamantyl(meth)acrylate, ethyladamantyl(meth)acrylate, methylcyclopentyl(meth)acrylate, ethylcyclopentyl(meth)acrylate, methylcyclohexyl(meth)acrylate, ethylcyclohexyl(meth)acrylate, and the like.

The resin (B1) can comprise one or more recurring units other than the above-mentioned recurring units (hereinafter referred to as "other recurring units (b1)").

As examples of the other recurring units (b1), units obtained by the cleavage of an polymerizable unsaturated bond of the following compounds can be given: vinyl aromatic compounds such as styrenes such as styrene, α-methylstyrene, 2-methylstyrene, 3-methylstyrene, 4-methylstyrene, 2-methoxystyrene, 3-methoxystyrene, 4-methoxystyrene, and 4-(2-t-butoxycarbonylethyloxy)styrene;

(meth)acrylates such as methyl (meth)acrylate, ethyl (meth)acrylate, n-propyl (meth)acrylate, n-butyl (meth)acrylate, i-butyl (meth)acrylate, n-pentyl (meth)acrylate, n-hexyl (meth)acrylate, 2-ethylhexyl (meth)acrylate, 2-hydroxyethyl (meth)acrylate, 2-hydroxypropyl (meth)acrylate, 3-hydroxypropyl (meth)acrylate, phenyl (meth)acrylate, phenethyl (meth)acrylate, and the monomers of the following formulas (11)–(13);

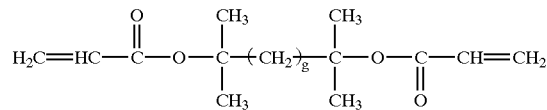

(11)

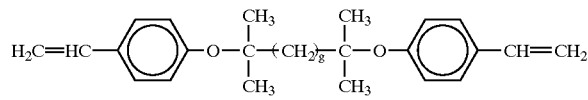

(12)

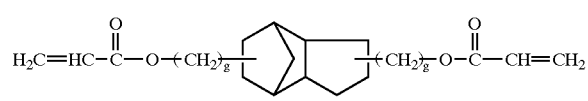

(13)

wherein g is an integer of 1–6;

unsaturated carboxylic acids such as (meth)acrylic acid, crotonic acid, maleic acid, fumaric acid, and cinnamic acid;

carboxyalkyl esters of unsaturated carboxylic acids such as 2-carboxyethyl (meth)acrylate, 2-carboxypropyl (meth)acrylate, and 3-carboxypropyl (meth)acrylate;

unsaturated nitryl compounds such as (meth)acrylonitrile, α-chloroacrylonitrile, crotonitrile, maleinitrile, and fumaronitrile;

unsaturated amide compounds such as (meth)acrylamide, N,N-dimethyl(meth)acrylamide, crotonamide, maleinamide, and fumaramide;

unsaturated imide compounds such as maleimide, N-phenylmaleimide, and N-cyclohexylmaleimide;

and other nitrogen-containing vinyl compounds such as N-vinyl-ε-caprolactam, N-vinylpyrrolidone, 2-vinylpyridine, 3-vinylpyridine, 4-vinylpyridine, 2-vinylimidazole, and 4-vinylimidazole.

Of these other recurring units (b1), units obtainable by cleavage of a polymerizable unsaturated bond in the compound such as α-methylstyrene, 4-(2-t-butoxycarbonylethyloxy)styrene, a monomer of the formula (11), or a monomer of the formula (12) are preferable.

As other acid-cleavable group-containing resins for the positive-tone radiation-sensitive resin composition (i) using a KrF excimer laser, a resin wherein the hydrogen atom of a phenolic hydroxyl group of a cresol novolac resin is replaced by the acid-cleavable group can be suitably used. As examples of preferable acid-cleavable groups for this resin, an ethoxyethyl group, t-butyl group, t-butoxycarbonyl group, t-butoxycarbonylmethyl group, and the like can be given.

As a suitable acid-cleavable group-containing resin for the positive-tone radiation-sensitive resin composition (i) using an ArF excimer laser, a resin insoluble or scarcely soluble in alkali comprising one or more recurring units of the following formula (14) and/or one or more recurring units of the following formula (15) is preferable (this resin is hereinafter referred to as "resin (B2)"). The resin (B2) is also suitable for use in a positive-tone radiation-sensitive resin composition (i) using a KrF excimer laser, ArF eximer laser, $F_2$ excimer laser, electron beams, or the like.

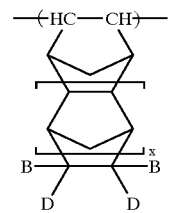

(14)

wherein B individually represent a hydrogen atom or an acid-cleavable group, at least one of B being the acid-cleavable group, D individually represent a hydrogen atom or a linear or branched monovalent alkyl group having 1–4 carbon atoms, and x is an integer of 0 to 2.

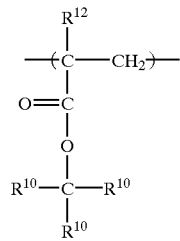

(15)

wherein $R^{12}$ represents a hydrogen atom, methyl group, hydroxyalkyl group or perfluoroalkyl group and $R^{10}$ individually represents a linear or branched alkyl group having 1–4 carbon atoms or a substituted or unsubstituted monovalent alicyclic hydrocarbon group having 4–20 carbon atoms, or any two of $R^{10}$ groups form in combination a substituted or unsubstituted divalent alicyclic hydrocarbon group having 4–20 carbon atoms, with the remaining $R^{10}$ group being a substituted or unsubstituted linear or branched alkyl group having 1–4 carbon atoms or a substituted or unsubstituted monovalent alicyclic hydrocarbon group having 4–20 carbon atoms.

As preferable recurring units of the formula (14), units having a norbornene skeleton obtainable by cleavage of a polymerizable unsaturated bond of the following monomers, for example, 5-t-butoxycarbonylbicyclo[2.2.1]hept-2-ene, 5-(4-t-butylcyclohexyloxy)carbonylbicyclo[2.2.1]hept-2-ene, 5-(1-ethoxyethoxy)carbonylbicyclo[2.2.1]hept-2-ene, 5-(1-cyclohexyloxyethoxy)carbonylbicyclo[2.2.1]hept-2-ene, 5-t-butoxycarbonylmethoxycarbonylbicyclo[2.2.1]hept-2-ene, 5-tetrahydrofuranyloxycarbonylbicyclo[2.2.1]hept-2-ene, 5-tetrahydropyranyloxycarbonylbicyclo[2.2.1]hept-2-ene, 8-t-butoxycarbonyltetracyclo[$4.4.0.1^{2,5}.1^{7,10}$]dodec-3-ene, 8-(4-t-butylcyclohexyloxy)carbonyltetracyclo[$4.4.0.1^{2,5}.1^{7,10}$]dodec-3-ene, 8-(1-ethoxyethoxy)carbonyltetracyclo[$4.4.0.1^{2,5}.1^{7,10}$]dodec-3-ene, 8-(1-cyclohexyloxyethoxy)carbonyltetracyclo[$4.4.0.1^{2,5}.1^{7,10}$]dodec-3-ene, 8-t-butoxycarbonylmethoxycarbonyltetracyclo[$4.4.0.1^{2,5}.1^{7,10}$]dodec-3-ene, 8-tetrahydrofuranyloxycarbonyltetracyclo[$4.4.0.1^{2,5}.1^{7,10}$]dodec-3-ene, and 8-tetrahydropyranyloxycarbonyltetracyclo[$4.4.0.1^{2,5}.1^{7,10}$]dodec-3-ene can be given.

As examples of the preferable recurring units of the formula (15), units obtained by the cleavage of a polymerizable unsaturated bond of t-butyl(meth)acrylate, 2-methyl-2-adamantyl(meth)acrylate, 2-ethyl-2-adamantyl(meth)acrylate, 2-methylcyclopentyl(meth)acrylate, 2-ethylcyclopentyl(meth)acrylate, 2-methylcyclohexyl(meth)acrylate, 2-ethocyclohexyl(meth)acrylate, and the units of the following formulas (15-1)–(15-12) can be given.

(15-1)

(15-2)

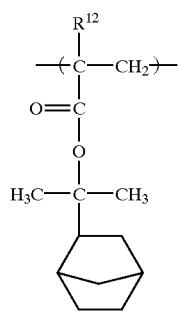

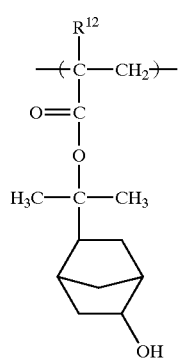

(15-3)

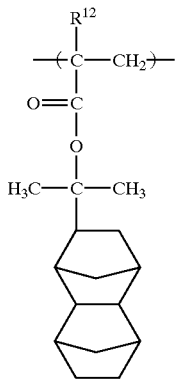

(15-4)

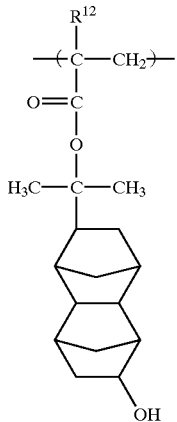

(15-5)

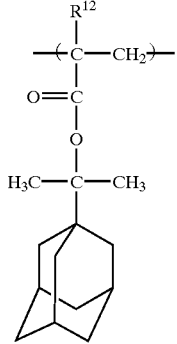

(15-6)

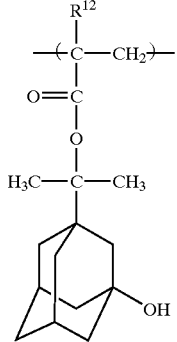

(15-7) 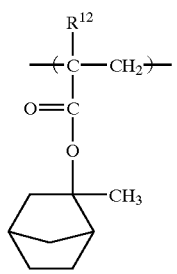

(15-8) 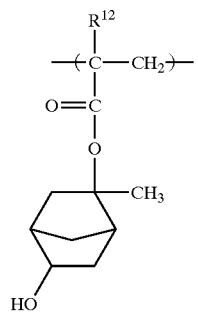

(15-9) 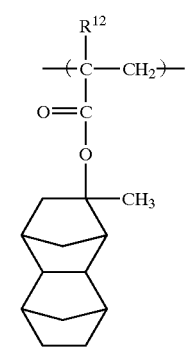

(15-10) 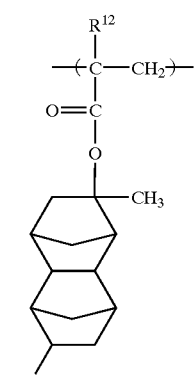

(15-11) 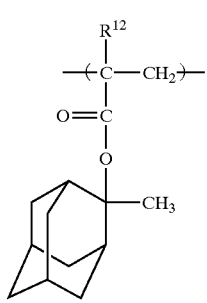

(15-12) 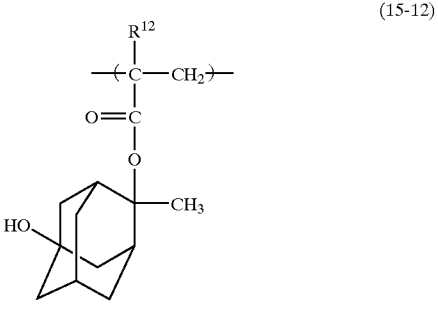

The resin (B2) can comprise one or more recurring units other than the above-mentioned recurring units (hereinafter referred to as "other recurring units (b2)").

As other recurring units (b2), units obtained by the cleavage of a polymerizable unsaturated bond of monomers having a norbornene skeleton such as norbornene(bicyclo[2.2.1]hept-2-ene, 5-methylbicyclo[2.2.1]hept-2-ene, 5-ethylbicyclo[2.2.1]hept-2-ene, 5-hydroxybicyclo[2.2.1]hept-2-ene, 5-fluorobicyclo[2.2.1]hept-2-ene, tetracyclo[$4.4.0.1^{2,5}.1^{7,10}$]dodec-3-ene, 8-methyltetracyclo[$4.4.0.1^{2,5}.1^{7,10}$]dodec-3-ene, 8-ethyltetracyclo[$4.4.0.1^{2,5}.1^{7,10}$]dodec-3-ene, 8-hydroxytetracyclo[$4.4.0.1^{2,5}.1^{7,10}$]dodec-3-ene, 8-fluorotetracyclo[$4.4.0.1^{2,5}.1^{7,10}$]dodec-3-ene;

unsaturated carboxylic acid anhydrides such as maleic anhydride and itaconic anhydride;

the (meth)acrylates previously given as examples of the other recurring units (b1) for the resin (B1);

3-hydroxy-1-adamantyl(meth)acrylate, the (meth)acrylate shown by the following formula (16):

(16) 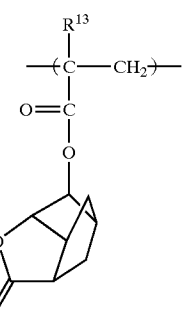

wherein $R^{13}$ represents a hydrogen atom or a methyl group; and the like can be given.

When the resin (B2) has the recurring units of the above formula (14), the recurring units originating from maleic anhydride are preferable as the other recurring units (b2).

As a suitable acid-cleavable group-containing resin for the positive-tone radiation-sensitive resin composition (i) using an $F_2$ excimer laser, a polysiloxane, insoluble or scarcely soluble in alkali, comprising one or more structural units of the following formula (17) and/or one or more structural units of the following formula (18) can be given (this resin is hereinafter referred to as "resin (B3)"). The resin (B3) preferably contains a structural unit of the formula (17). The resin (B3) is also suitable for use in a positive-tone radiation-sensitive resin composition (i) using a KrF excimer laser, ArF excimer laser, electron beams, or the like.

(17)

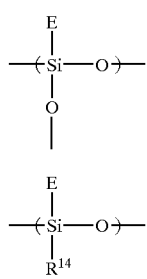

(18)

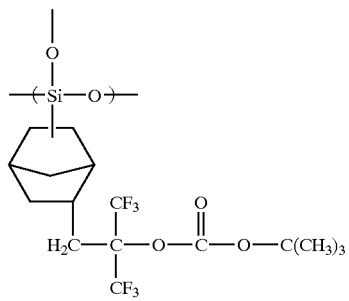

wherein E individually represents a monovalent organic group-containing an acid-cleavable group, and $R^{14}$ represents a substituted or unsubstituted linear, branched, or cyclic monovalent hydrocarbon group having 1–20 carbon atoms.

As preferable examples of the group E in the formulas (17) and (18), alicyclic hydrocarbon groups (such as a cycloalkyl group, norbornyl group, tricyclodecanyl group, tetracyclodecanyl group, and adamantyl group) having an acid-cleavable group, halogenated aromatic hydrocarbon groups having an acid-cleavable group, and the like can be given.

As particularly preferable examples of the structural unit of the formula (17) for the resin (B3), structural units of the following formulas (17-1) to (17-4) can be given.

(17-1)

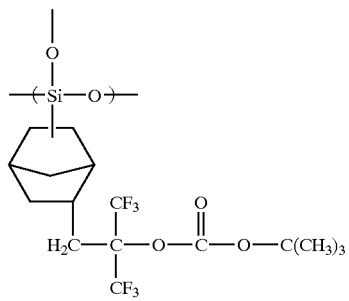

(17-2)

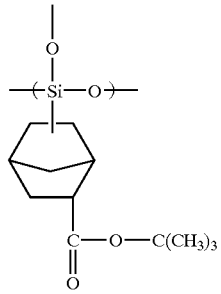

(17-3)

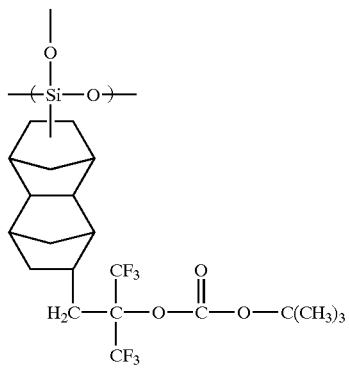

(17-4)

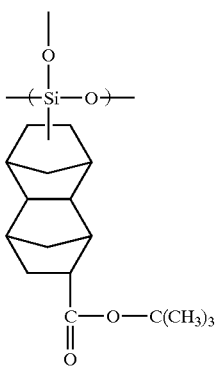

The resin (B3) can comprise one or more structural units other than the above-mentioned structural units (hereinafter referred to as "other structural units (b3)").

As preferable other structural units (b3), structural units produced by hydrolysis and condensation of alkylalkoxysilanes such as methyltrimethoxysilane, methyltriethoxysilane, ethyltrimethoxysilane, ethyltriethoxysilane, and the like; and the structural units shown by the following formulas (18-1)–(18-4) can be given.

(18-1)

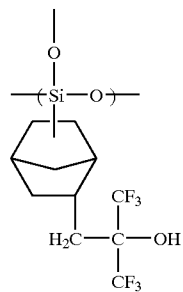

(18-2)

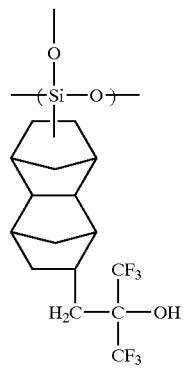

(18-3)

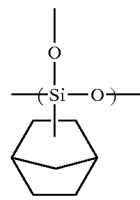

(18-4)

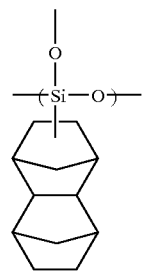

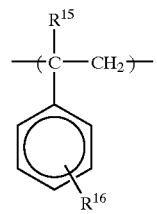
(19)

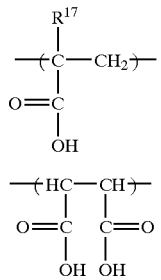
(20)

(21)

The resin (B3) can be produced by the (co)polycondensation of a silane compound having a monovalent organic group with an acid-cleavable group, or by the introduction of an acid-cleavable group and/or monovalent organic group having an acid-cleavable group into a previously prepared organic polysiloxane.

In the (co)polycondensation of the silane compound having a monovalent organic compound with an acid-cleavable group, it is preferable to use an acidic catalyst as the catalyst, and particularly preferable to react the silane compound by polycondensation in the presence of an acidic catalyst, and to continue the reaction with an addition of a base catalyst.

As examples of the acidic catalyst, inorganic acids such as hydrochloric acid, sulfuric acid, nitric acid, boric acid, phosphoric acid, titanium tetrachloride, zinc chloride and aluminium chloride; organic acids such as formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzene sulfonic acid, p-toluenesulfonic acid, and methane sulfonic acid can be given.

Of these acidic catalysts, hydrochloric acid, sulfuric acid, acetic acid, oxalic acid, malonic acid, maleic acid, fumaric acid, acetic anhydride, and maleic anhydride are particularly preferable.

As examples of the above base catalysts, inorganic bases such as lithium hydroxide, sodium hydroxide, potassium hydroxide, calcium hydroxide, barium hydroxide, sodium hydrogencarbonate, potassium hydrogencarbonate, sodium carbonate, and potassium carbonate; organic bases such as triethylamine, tri-n-propylamine, tri-n-butylamine, and pyridine can be given.

Alkali-Soluble Resin

The alkali-soluble resin used in the positive-tone radiation-sensitive resin composition (ii) is a resin having one or more functional groups exihibiting affinity with an alkaline developing solution, for example, an oxygen-containing functional group such as a phenolic hydroxyl group, alcoholic hydroxyl group, or carboxyl group.

As examples of such an alkali-soluble resin, an addition polymerization resin having one or more recurring units of the following formulas (19) to (21), and a polycondensation resin having one or more recurring units of the following formula (22) can be given.

wherein $R^{15}$ and $R^{17}$ individually represent a hydrogen atom or a methyl group, $R^{16}$ represents a hydroxyl group, a carboxyl group, —$R^{18}$COOH, —O$R^{18}$COOH, —OCO$R^{18}$COOH, or —COO$R^{18}$COOH ($R^{18}$ individually represents a group —(CH$_2$)h-, wherein h is an integer of 1–4).

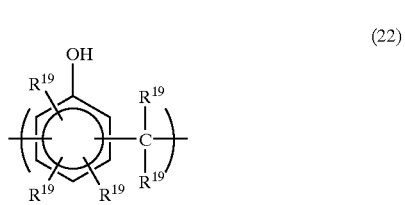
(22)

wherein $R^{19}$ individually represent a hydrogen atom or a linear or branched alkyl group having 1–4 carbon atoms.

In the case where the alkali-soluble resin is an addition polymerization resin, such a resin may be formed only from the recurring units of the formulas (19) to (21), or may further contain one or more other recurring units (hereinafter referred to as "other recurring units (c1)") inasmuch as the resin is soluble in an alkaline developer.

As examples of the other recurring units (c1), the other recurring units (b1) for the resin (B1) and the like can be given.

In the case where the alkali-soluble resin is a polycondensation resin, such a resin may be formed only from the recurring units of the formula (22), or may further contain one or more other recurring units (hereinafter referred to as "other recurring units (c2)") inasmuch as the resin is soluble in an alkaline developer.

Although the content of the recurring units of the formulas (19) to (22) in the alkali-soluble resin cannot be generically specified and varies according to the types of the other recurring units (c1) or other recurring units (c2), such a content is preferably 10–100 mol %, and more preferably 20–100 mol %.

The alkali soluble resin may be used as the hydrogenate when the resin has a recurring unit which contains a carbon-carbon unsaturated bond such as a recurring unit of the formulas (19) and (22), for example. In this instance, the hydrogenation degree is usually 70% or less, preferably 50% or less, and still more preferably 40% or less of the total amount of the carbon-carbon unsaturated bonds in the recurring units of the formulas (19), (22), and the other similar recurring units. If the hydrogenation degree is more than 70%, developability of the alkali-soluble resin by an alkaline developer may decrease.

As an alkali-soluble resin in the positive-tone radiation-sensitive resin composition (ii), a resin containing poly(4-hydroxystyrene), 4-hydroxystyrene/4-hydroxy-α-methylstyrene copolymer, 4-hydroxystyrene/styrene copolymer, or the like as a major component is particularly preferable.

Although Mw of the alkali-soluble resin varies according to the characteristics desired for the positive-tone radiation-sensitive resin composition (ii), a preferable range is 1,000–150,000, with the range of 3,000–100,000 being more preferable.

These alkali-soluble resins may be used either individually or in combination of two or more.

Alkali Solubility Control Agent

As examples of the alkali solubility control agent in the positive-tone radiation-sensitive resin composition (ii), compounds in which a hydrogen atom in the acidic functional group such as a phenolic hydroxyl group and a carboxyl group is replaced by an acid-cleavable group or t-butoxycarbonylmethyl group can be given.

As examples of the acid-cleavable group, the same acid-cleavable groups as mentioned in connection with the acid-cleavable group-containing resin, such as a substituted methyl group, 1-substituted ethyl group, 1-substituted n-propyl group, 1-branched alkyl group, silyl group, germyl group, alkoxycarbonyl group, acyl group, cyclic acid-cleavable group, and the like, can be given.

The alkali solubility control agent may be either a low molecular weight compound or a high molecular weight compound. As examples of the low molecular weight compound, the compounds of the following formulas (23) to (27):

(23)

(24)

(25)

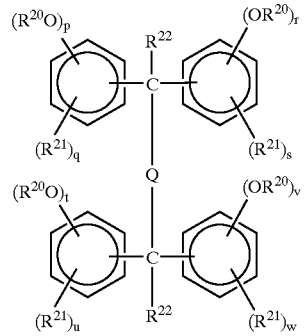
(26)

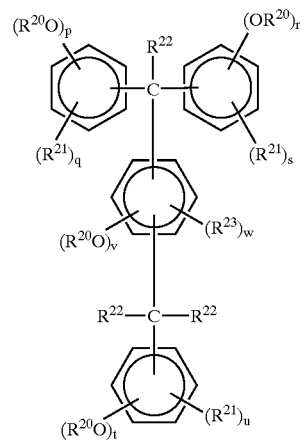
(27)

wherein $R^{20}$ individually represent an acid-cleavable group or a t-butoxycarbonylmethyl group, $R^{21}$ individually represent a linear or branched alkyl group, phenyl group, or 1-naphtyl group having 1–4 carbon atoms, $R^{22}$ individually represent a hydrogen atom, a linear or branched alkyl group having 1–4 carbon atoms, or a phenyl group, Q represents a single bond, —O—, —S—, —CO—, —COO—, —SO—, —$SO_2$—, —$C(R^{23})(R^{24})$— (wherein $R^{23}$ and $R^{24}$ individually represent a hydrogen atom, a linear or branched alkyl group having 1–6 carbon atoms, a linear or branched acyl group having 2–11 carbon atoms, a phenyl group, or a 1-naphtyl group), or a substituted or unsubstituted phenylene group, p, q, r, s, t, u, v, and w represent an integer of 0 or more, provided that $5 \geq p \geq 1$ for formula (23), $10 \geq (p+r) \geq 1$ for formula (24), $15 \geq (p+r+t) \geq 1$ for formula (25), $20 \geq (p+r+t+v) \geq 1$ for formula (26), and $19 \geq (p+r+t+v) \geq 1$ for formula (27); steroids (bile acids) such as cholic acid, deoxycholic acid, and lithocholic acid; compounds containing an alicyclic ring or aromatic ring such as adamantane carbonic acid or adamantane dicarbonic acid, wherein the hydrogen atom of the carboxyl group in the carbonic acid compound is replaced by the above-mentioned acid-cleavable group or t-butoxycarbonylmethyl group; and the like can be given.

As a high molecular weight alkali solubility control agent, the above-described acid-cleavable group-containing resins, for example, can be used.

As preferable alkali solubility control agents for the positive-tone radiation-sensitive resin composition (ii), steroids (bile acids) such as cholic acid, deoxycholic acid, and lithocholic acid, compounds containing an alicyclic ring or aromatic ring such as adamantane carbonic acid or adamantane dicarbonic acid, wherein the hydrogen atom of the carboxyl group in the carbonic acid compound is replaced by the above-mentioned acid-cleavable group or t-butoxycarbonylmethyl group, and the like can be given.

These alkali solubility control agents may be used either individually or in combination of two or more.

Negative-Tone Radiation-Sensitive Resin Composition

The negative-tone radiation-sensitive resin composition of the present invention (hereinafter referred to as "negative-tone radiation-sensitive resin composition (iii)") comprises: (A) the acid generator (I), (C) an alkali soluble resin, and (E) a compound that cross-links an alkali soluble resin in the presence of an acid (hereinafter referred to as "crosslinking agent (E)").

As the acid generator (I) used in the negative-tone radiation-sensitive resin composition (iii), acid generators having heat and chemical stability are preferable.

The negative-tone radiation-sensitive resin composition (iii) of the present invention will now be described.

Alkali-Soluble Resin

As examples of the alkali-soluble resin for the negative-tone radiation-sensitive resin composition (iii), the resins given for the positive-tone radiation-sensitive resin composition (ii) can be given.

As an alkali-soluble resin in the negative-tone radiation-sensitive resin composition (iii), a resin containing poly(4-hydroxystyrene), 4-hydroxystyrene/4-hydroxy-α-methylstyrene copolymer, 4-hydroxystyrene/styrene copolymer, or the like as a major component is preferable.

Although Mw of the alkali-soluble resin varies according to the characteristics desired for the negative-tone radiation-sensitive resin composition (iii), a preferable range is 1,000–150,000, with the range of 3,000–100,000 being more preferable.

These alkali-soluble resins may be used either individually or in combination of two or more.

Crosslinking Agent (E)

As an example of the crosslinking agent (E) for the negative-tone radiation-sensitive resin composition (iii), a compound having one or more functional groups (hereinafter referred to as "crosslinkable functional group") which exhibit crosslinking reactivity with the alkali-soluble resin can be given.

As examples of the crosslinkable functional group, a glycidyl ether group, glycidyl ester group, glycidyl amino group, methoxymethyl group, ethoxymethyl group, benzyloxymethyl group, acetoxymethyl group, benzoiloxy methyl group, formyl group, acetyl group, vinyl group, iso-propenyl group, (dimethylamino)methyl group, (diethylamino)methyl group, (dimethylolamino)methyl group, (diethylolamino) methyl group, morpholinomethyl group, and the like can be given.

As examples of the crosslinking agent (E), a bisphenol A epoxy compound, bisphenol F epoxy compound, bisphenol S epoxy compound, novolac resin epoxy compound, resol resin epoxy compound, poly(hydroxystyrene) epoxy compound, methylol group-containing melamine compound, methylol group-containing benzoguanamine compound, methylol group-containing urea compound, methylol group-containing phenol compound, alkoxyalkyl group-containing melamine compound, alkoxyalkyl group-containing benzoguanamine compound, alkoxyalkyl group-containing urea compound, alkoxyalkyl group-containing phenol compound, carboxymethyl group-containing melamine resin, carboxymethyl group-containing benzoguanamine resin, carboxymethyl group-containing urea resin, carboxymethyl group-containing phenol resin, carboxymethyl group-containing melamine compound, carboxymethyl group-containing benzoquanamine compound, carboxymethyl group-containing urea compound, carboxymethyl group-containing phenol compound, and the like can be given.

Of these crosslinking agents (E), a methylol group-containing phenol compound, methoxymethyl group-containing melamine compound, methoxymethyl group-containing phenol compound, methoxymethyl group-containing glycoluril compound, methoxymethyl group-containing urea compound, and acetoxymethyl group-containing phenol compound are preferable, with particularly preferable compounds being a methoxymethyl group-containing melamine compound (for example, hexamethoxymethylmelamine), methoxymethyl group-containing glycoluril compound, methoxymethyl group-containing urea compound, and the like. Methoxymethyl group-containing melamine compounds are commercially available under the trademarks CYMEL300, CYMEL301, CYMEL303, and CYMEL305 (manufactured by Mitsui Cyanamid Co., Ltd.), methoxymethyl group-containing glycoluril compounds are commercially available under the trademark CYMEL 1174 (manufactured by Mitsui Cyanamid Co., Ltd.) and the like; and methoxymethyl group-containing urea compounds are commercially available under the trademark MX290 (manufactured by Sanwa Chemical Co., Ltd.) and the like.

A resin provided with crosslinking agent characteristics by replacing a hydrogen atom of an oxygen containing functional group in an alkali-soluble resin with the above-mentioned crosslinkable functional group can also be suitably used as the crosslinking agent (E) The amount of the crosslinkable functional group introduced is usually 5–60 mol %, preferably 10–50 mol %, and still more preferably 15–40 mol % of the total oxygen containing functional groups in the alkali-soluble resin, although the specific percentage may vary depending on types of crosslinkable functional group and the alkali-soluble resin into which the crosslinkable functional group is introduced. The amount of crosslinkable functional group less than 5 mol % may decrease the rate of residual coatings and tends to induce meandering and swelling of the patterns. If the amount exceeds 60 mol %, developability of exposed areas tends to decrease.

Methoxymethyl group-containing compounds such as dimethoxymethyl urea and tetramethoxymethyl glycoluril are preferable as the crosslinking agent (E) for the negative-tone radiation-sensitive resin composition (iii).

The crosslinking agent (E) may be used either individually or in combination of two or more.

Other Acid Generators

The positive-tone radiation-sensitive resin composition (i), positive-tone radiation-sensitive resin composition (ii), and negative-tone radiation-sensitive resin composition (iii) may contain acid generators other than the acid generator (I) as required (hereinafter referred to as "other acid generators").

As examples of the other acid generators, sulfonimide compounds, onium salt compounds, sulfone compounds, sulfonate compounds, disulfonyl diazomethane compounds, disulfonyl methane compounds, oxime sulfonate compounds, hydrazinesulfonate compounds, and the like can be given.

Examples of these other acid generators are as follows:

<Sulfonimide Compounds>

As examples of sulfonimide compounds, compounds of the following formula (28) can be given:

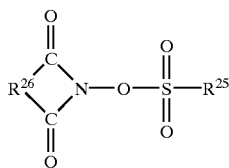

(28)

wherein $R^{25}$ is a monovalent organic group and $R^{26}$ is a divalent organic group.

Specific examples of sulfonimide compounds include:
N-(trifluoromethanesulfonyloxy)succinimide,
N-(trifluoromethylsulfonyloxy)phthalimide,
N-(trifluoromethylsulfonyloxy)diphenylmaleimide,
N-(trifluoromethylsulfonyloxy)bicyclo[2.2.1]hept-5-ene-2,3-dicarboxyimide,
N-(trifluoromethylsulfonyloxy)-7-oxabicyclo[2.2.1]hept-5-ene-2,3-dicarboxyimide,
N-(trifluoromethylsulfonyloxy)bicyclo[2.2.1]heptan-5,6-oxy-2,3-dicarboxyimide,
N-(trifluoromethylsulfonyloxy)naphthylimide,
N-(10-camphorsulfonyloxy)succinimide,
N-(10-camphorsulfonyloxy)phthalimide,
N-(10-camphorsulfonyloxy)diphenylmaleimide,
N-(10-camphorsulfonyloxy)bicyclo[2.2.1]hept-5-ene-2,3-dicarboxyimide,
N-(10-camphorsulfonyloxy)-7-oxabicyclo[2.2.1]hept-5-ene-2,3-dicarboxyimide,
N-(10-camphorsulfonyloxy)bicyclo[2.2.1]heptan-5,6-oxy-2,3-dicarboxyimide,
N-(10-camphorsulfonyloxy)naphthylimide,
N-(n-octanesulfonyloxy)succinimide,
N-(n-octanesulfonyloxy)phthalimide,
N-(n-octanesulfonyloxy)diphenylmaleimide,
N-(n-octanesulfonyloxy)bicyclo[2.2.1]hept-5-ene-2,3-dicarboxyimide,
N-(n-octanesulfonyloxy)-7-oxabicyclo[2.2.1]hept-5-ene-2,3-dicarboxyimide,
N-(n-octanesulfonyloxy)bicyclo[2.2.1]heptane-5,6-oxy-2,3-dicarboxyimide,
N-(n-octanesulfonyloxy)naphthylimide,
N-(p-toluenesulfonyloxy)succinimide,
N-(p-toluenesulfonyloxy)phthalimide,
N-(p-toluenesulfonyloxy)diphenylmaleimide,
N-(p-toluenesulfonyloxy)bicyclo[2.2.1]hept-5-ene-2,3-dicarboxyimide,
N-(p-toluenesulfonyloxy)-7-oxabicyclo[2.2.1]hept-5-ene-2,3-dicarboxyimide,
N-(p-toluenesulfonyloxy)bicyclo[2.2.1]heptane-5,6-oxy-2,3-dicarboxyimide,
N-(p-toluenesulfonyloxy)naphthylimide,
N-(2-trifluoromethylbenzenesulfonyloxy)succinimide,
N-(2-trifluoromethylbenzenesulfonyloxy)phthalimide,
N-(2-trifluoromethylbenzenesulfonyloxy)diphenylmaleimide,
N-(2-trifluoromethylbenzenesulfonyloxy)bicyclo[2.2.1]hept-5-ene-2,3-dicarboxyimide,
N-(2-trifluoromethylbenzenesulfonyloxy)-7-oxabicyclo[2.2.1]hept-5-ene-2,3-dicarboxyimide,
N-(2-trifluoromethylbenzenesulfonyloxy)bicyclo[2.2.1]heptan-5,6-oxy-2,3-dicarboxyimide,
N-(2-trifluoromethylbenzenesulfonyloxy)naphthylimide,
N-(4-trifluoromethylbenzenesulfonyloxy)succinimide,
N-(4-trifluoromethylbenzenesulfonyloxy)phthalimide,
N-(4-trifluoromethylbenzenesulfonyloxy)diphenylmaleimide,
N-(4-trifluoromethylbenzenesulfonyloxy)bicyclo[2.2.1]hept-5-ene-2,3-dicarboxyimide,
N-(4-trifluoromethylbenzenesulfonyloxy)-7-oxabicyclo[2.2.1]hept-5-ene-2,3-dicarboxyimide,
N-(4-trifluoromethylbenzenesulfonyloxy)bicyclo[2.2.1]heptane-5,6-oxy-2,3-dicarboxyimide,
N-(4-trifluoromethylbenzenesulfonyloxy)naphthylimide,
N-(perfluorobenzenesulfonyloxy)succinimide,
N-(perfluorobenzenesulfonyloxy)phthalimide,
N-(perfluorobenzenesulfonyloxy)diphenylmaleimide,
N-(perfluorobenzenesulfonyloxy)bicyclo[2.2.1]hept-5-ene-2,3-dicarboxyimide,
N-(perfluorobenzenesulfonyloxy)-7-oxabicyclo[2.2.1]hept-5-ene-2,3-dicarboxyimide,
N-(perfluorobenzenesulfonyloxy)bicyclo[2.2.1]heptan-5,6-oxy-2,3-dicarboxyimide,
N-(perfluorobenzenesulfonyloxy)naphthylimide,
N-(1-naphtalenesulfonyloxy)succinimide,
N-(1-naphtalenesulfonyloxy)phthalimide,
N-(1-naphtalenesulfonyloxy)diphenylmaleimide,
N-(1-naphtalenesulfonyloxy)bicyclo[2.2.1]hept-5-ene-2,3-dicarboxyimide,
N-(1-naphtalenesulfonyloxy)-7-oxabicyclo[2.2.1]hept-5-ene-2,3-dicarboxyimide,
N-(1-naphtalenesulfonyloxy)bicyclo[2.2.1]heptan-5,6-oxy-2,3-dicarboxyimide,
N-(1-naphtalenesulfonyloxy)naphthylimide,
N-(benzenesulfonyloxy)succinimide,
N-(benzenesulfonyloxy)phthalimide,
N-(benzenesulfonyloxy)diphenylmaleimide,
N-(benzenesulfonyloxy)bicyclo[2.2.1]hept-5-ene-2,3-dicarboxyimide,
N-(benzenesulfonyloxy)-7-oxabicyclo[2.2.1]hept-5-ene-2,3-dicarboxyimide,
N-(benzenesulfonyloxy)bicyclo[2.2.1]heptan-5,6-oxy-2,3-dicarboxyimide, N-(benzenesulfonyloxy)naphthylimide,
N-{(5-methyl-5-methoxycarbonylbicyclo[2.2.1]heptan-2-yl)sulfonyloxy}succinimide,
N-{(5-methyl-5-methoxycarbonylbicyclo[2.2.1]heptan-2-yl)sulfonyloxy}bicyclo[2.2.1]hept-5-ene-2,3-dicarboxyimide,
and the like can be given.

<Onium Salt Compounds>

As examples of onium salt compounds, iodonium salts, sulfonium salts (including thiophenium salts), phosphonium salts, diazonium salts, ammonium salts, and pyridinium salts can be given.

Specific examples of onium salts include: bis(4-t-butylphenyl)iodonium trifluoromethanesufonate, bis(4-t-butylphenyl)iodonium pyrenesulfonate, bis(4-t-butylphenyl)iodonium n-dodecylbenzenesulfonate, bis(4-t-butylphenyl)iodonium p-toluenesulfonate, bis(4-t-butylphenyl)iodonium benzenesulfonate, bis(4-t-butylphenyl)iodonium 10-camphorsulfonate, bis(4-t-butylphenyl)iodonium n-octanesulfonate, bis(4-t-butylphenyl)iodonium 2-trifluoromethylbenzenesulfonate, bis(4-t-butylphenyl)iodonium 4-trifluoromethylbenzenesulfonate, bis(4-t-butylphenyl)iodonium perfluorobenzenesulfonate, diphenyliodonium trifluoromethanesulfonate, diphenyliodonium pyrenesulfonate, diphenyliodonium n-dodecylbenzenesulfonate, diphenyliodonium p-toluenesulfonate, diphenyliodonium benzenesulfonate, diphenyliodonium 10-camphorsulfonate, diphenyliodonium n-octanesulfonate, diphenyliodonium 2-trifluoromethylbenzenesulfonate, diphenyliodonium 4-trifluoromethylbenzenesulfonate, diphenyliodonium perfluorobenzenesulfonate, di(p-tolyl)iodonium trifluoromethane sulfonate, di(p-tolyl)iodonium pyrenesulfonate, di(p-tolyl)iodonium n-dodecylbenzenesulfonate, di(p-tolyl)iodonium p-toluene sulfonate, di(p-tolyl)iodonium benzenesulfonate, di(p-tolyl)iodonium 10-camphorsulfonate, di(p-tolyl)iodonium n-octanesulfonate, di(p-tolyl)iodonium 2-trifluoromethylbenzene sulfonate, di(p-tolyl)iodonium 4-trifluoromethylbenzenesulfonate, di(p-tolyl)iodonium perfluorobenzenesulfonate, di(3,4-dimethylphenyl)iodonium trifluoromethanesufonate, di(3,4-dimethylphenyl)iodonium pyrenesulfonate, di(3,4-dimethylphenyl)iodonium n-dodecylbenzenesulfonate, di(3,4-dimethylphenyl)iodonium p-toluenesulfonate, di(3,4-dimethylphenyl)iodonium benzenesulfonate, di(3,4-dimethylphenyl)iodonium 10-camphorsulfonate, di(3,4-dimethylphenyl)iodonium n-octanesulfonate, di(3,4-dimethylphenyl)iodonium 2-trifluoromethylbenzenesulfonate, di(3,4-dimethylphenyl)iodonium 4-trifluoromethyl benzenesulfonate, di(3,4-dimethylphenyl)iodonium perfluorobenzenesulfonate, 4-nitrophenyl.phenyliodonium trifluoromethanesulfonate, 4-nitrophenyl.phenyliodonium pyrenesulfonate, 4-nitrophenyl.phenyliodonium n-dodecylbenzenesulfonate, 4-nitrophenyl.phenyliodonium p-toluenesulfonate, 4-nitrophenyl.phenyliodonium benzenesulfonate, 4-nitrophenyl.phenyliodonium 10-camphorsulfonate, 4-nitrophenyl.phenyliodonium n-octanesulfonate, 4-nitrophenyl.phenyliodonium 2-trifluoromethylbenzenesulfonate, 4-nitrophenyl.phenyliodonium 4-trifluoromethylbenzenesulfonate, 4-nitrophenyl.phenyliodonium perfluorobenzenesulfonate, di(3-nitrophenyl)iodonium trifluoromethane sulfonate, di(3-nitrophenyl)iodonium pyrenesulfonate, di(3-nitrophenyl)iodonium n-dodecylbenzenesulfonate, di(3-nitrophenyl)iodonium p-toluene sulfonate, di(3-nitrophenyl)iodonium benzenesulfonate, di(3-nitrophenyl)iodonium 10-camphorsulfonate, di(3-nitrophenyl)iodonium n-octanesulfonate, di(3-nitrophenyl)iodonium 2-trifluoromethylbenzene sulfonate, di(3-nitrophenyl)iodonium 4-trifluoromethylbenzenesulfonate, di(3-nitrophenyl)iodonium perfluorobenzenesulfonate, 4-methoxyphenyl.phenyliodonium trifluoromethanesulfonate, 4-methoxyphenyl.phenyliodonium pyrenesulfonate, 4-methoxyphenyl.phenyliodonium n-dodecylbenzenesulfonate, 4-methoxyphenyl.phenyliodonium p-toluenesulfonate, 4-methoxyphenyl.phenyliodonium benzenesulfonate, 4-methoxyphenyl.phenyliodonium 10-camphorsulfonate, 4-methoxyphenyl.phenyliodonium n-octanesulfonate, 4-methoxyphenyl.phenyliodonium 2-trifluoromethylbenzenesulfonate, 4-methoxyphenyl.phenyliodonium 4-trifluoromethylbenzenesulfonate, 4-methoxyphenyl.phenyliodonium perfluorobenzenesulfonate, di(4-chlorophenyl)iodonium trifluoromethane sulfonate, di(4-chlorophenyl)iodonium pyrenesulfonate, di(4-chlorophenyl)iodonium n-dodecylbenzenesulfonate, di(4-chlorophenyl)iodonium p-toluenesulfonate, di(4-chlorophenyl)iodonium benzenesulfonate, di(4-chlorophenyl)iodonium 10-camphorsulfonate, di(4-chlorophenyl)iodonium n-octanesulfonate, di(4-chlorophenyl)iodonium 2-trifluoromethylbenzenesulfonate, di(4-chlorophenyl)iodonium 4-trifluoromethylbenzenesulfonate, di(4-chlorophenyl)iodonium perfluorobenzenesulfonate, di(4-trifluoromethylphenyl)iodonium trifluoromethanesulfonate, di(4-trifluoromethylphenyl)iodonium pyrenesulfonate, di(4-trifluoromethylphenyl)iodonium n-dodecylbenzenesulfonate, di(4-trifluoromethylphenyl)iodonium p-toluenesulfonate, di(4-trifluoromethylphenyl)iodonium benzenesulfonate, di(4-trifluoromethylphenyl)iodonium 10-camphorsulfonate, di(4-trifluoromethylphenyl)iodonium n-octanesulfonate, di(4-trifluoromethylphenyl)iodonium 2-trifluoromethylbenzenesulfonate, di(4-trifluoromethylphenyl)iodonium 4-trifluoromethylbenzenesulfonate, di(4-trifluoromethylphenyl)iodonium perfluorobenzenesulfonate, di(1-napthyl)iodonium trifluoromethanesulfonate, di(1-napthyl)iodonium trifluoromethanesulfonate, di(1-napthyl)iodonium nonafluoro-n-butanesulfonate, di(1-napthyl)iodonium perfluoro-n-octanesulfonate, di(1-napthyl)iodonium pyrenesulfonate, di(1-napthyl)iodonium n-dodecylbenzenesulfonate, di(1-napthyl)iodonium p-toluenesulfonate, di(1-napthyl)iodonium benzenesulfonate, di(1-napthyl)iodonium 10-camphorsulfonate, di(1-napthyl)iodonium n-octanesulfonate, di(1-napthyl)iodonium 2-trifluoromethylbenzenesulfonate, di(1-napthyl)iodonium 4-trifluoromethylbenzenesulfonate, di(1-napthyl)iodonium perfluorobenzenesulfonate, biphenyleneiodonium trifluoromethanesulfonate, biphenyleneiodonium pyrenesulfonate, biphenyleneiodonium n-dodecylbenzenesulfonate, biphenyleneiodonium p-toluenesulfonate, biphenyleneiodonium benzenesulfonate, biphenyleneiodonium 10-camphorsulfonate, biphenyleneiodonium n-octanesulfonate, biphenyleneiodonium 2-trifluoromethylbenzenesulfonate, biphenyleneiodonium 4-trifluoromethylbenzenesulfonate, biphenyleneiodonium perfluorobenzenesulfonate, 2-chlorobiphenyleneiodonium trifluoromethanesulfonate, 2-chlorobiphenyleneiodonium pyrenesulfonate, 2-chlorobiphenyleneiodonium n-dodecylbenzenesulfonate, 2-chlorobiphenyleneiodonium p-toluenesulfonate, 2-chlorobiphenyleneiodonium benzenesulfonate, 2-chlorobiphenyleneiodonium 10-camphorsulfonate, 2-chlorobiphenyleneiodonium n-octanesulfonate, 2-chlorobiphenyleneiodonium 2-trifluoromethylbenzenesulfonate, 2-chlorobiphenyleneiodonium 4-trifluoromethylbenzenesulfonate, 2-chlorobiphenyleneiodonium perfluorobenzenesulfonate, triphenylsulfonium trifluoromethanesulfonate, triphenylsulfonium pyrenesulfonate, triphenylsulfonium n-dodecylbenzenesulfonate, triphenylsulfonium p-toluenesulfonate, triphenylsulfonium benzenesulfonate, triphenylsulfonium 10-camphorsulfonate, triphenylsulfonium n-octanesulfonate, triphenylsulfonium 2-trifluoromethylbenzenesulfonate, triphenylsulfonium 4-trifluoromethylbenzenesulfonate, triphenylsulfonium hexafluoroantimonate, triphenylsulfonium naphthalenesulfonate, triphenylsulfonium perfluorobenzenesulfonate, 4-t-butylphenyl.diphenylsulfonium trifluoromethanesulfonate, 4-t-butylphenyl.diphenylsulfonium pyrenesulfonate, 4-t-butylphenyl.diphenylsulfonium n-dodecylbenzenesulfonate, 4-t-butylphenyl.diphenylsulfonium p-toluenesulfonate, 4-t-butylphenyl.diphenylsulfonium benzenesulfonate, 4-t-butylphenyl.diphenylsulfonium 10-camphorsulfonate, 4-t-butylphenyl.diphenylsulfonium n-octanesulfonate, 4-t-butylphenyl.diphenylsulfonium 2-trifluoromethylbenzenesulfonate, 4-t- butylphenyl.diphenylsulfonium 4-trifluoromethanebenzenesulfonate, 4-t-butylphenyl.diphenylsulfonium perfluorobenzenesulfonate, 4-t-butoxyphenyl.diphenylsulfonium trifluoromethanesulfonate, 4-t-butoxyphenyl.diphenylsulfonium pyrenesulfonate, 4-t-butoxyphenyl.diphenylsulfonium n-dodecylbenzenesulfonate, 4-t-butoxyphenyl.diphenylsulfonium p-toluenesulfonate, 4-t-butoxyphenyl.diphenylsulfonium benzenesulfonate, 4-t-butoxyphenyl.diphenylsulfonium 10-camphorsulfonate, 4-t-butoxyphenyl.diphenylsulfonium n-octanesulfonate, 4-t-butoxyphenyl.diphenylsulfonium 2-trifluoromethylbenzenesulfonate, 4-t-butoxyphenyl.diphenylsulfonium 4-trifluoromethylbenzenesulfonate, 4-t-butoxyphenyl.diphenylsulfonium perfluorobenzenesulfonate, 4-hydroxyphenyl.diphenylsulfonium trifluoromethanesulfonate, 4-hydroxyphenyl.diphenylsulfonium pyrenesulfonate, 4-hydroxyphenyl.diphenylsulfonium n-dodecylbenzenesulfonate, 4-hydroxyphenyl.diphenylsulfonium p-toluenesulfonate, 4-hydroxyphenyl.diphenylsulfonium benzenesulfonate, 4-hydroxyphenyl.diphenylsulfonium 10-camphorsulfonate, 4-hydroxyphenyl.diphenylsulfonium n-octanesulfonate, 4-hydroxyphenyl.diphenylsulfonium 2-trifluoromethylbenzenesulfonate, 4-hydroxyphenyl.diphenylsulfonium 4-trifluoromethylbenzenesulfonate, 4-hydroxyphenyl.diphenylsulfonium perfluorobenzenesulfonate, tri(4-methoxyphenyl)sulfonium trifluoromethanesulfonate, tri(4-methoxyphenyl)sulfonium pyrenesulfonate, tri(4-methoxyphenyl)sulfonium n-dodecylbenzenesulfonate, tri(4-methoxyphenyl)sulfonium p-toluenesulfonate, tri(4-methoxyphenyl)sulfonium benzenesulfonate, tri(4-methoxyphenyl)sulfonium 10-camphorsulfonate, tri(4-methoxyphenyl)sulfonium n-octanesulfonate, tri(4-methoxyphenyl)sulfonium 2-trifluoromethylbenzenesulfonate, tri(4-methoxyphenyl)sulfonium 4-trifluoromethylbenzenesulfonate, tri(4-methoxyphenyl)sulfonium perfluorobenzenesulfonate, di(4-methoxyphenyl).p-tolylsulfonium trifluoromethanesulfonate, di(4-methoxyphenyl).p-tolylsulfonium pyrenesulfonate, di(4-methoxyphenyl).p-tolylsulfonium n-dodecylbenzenesulfonate, di(4-methoxyphenyl).p-tolylsulfonium p-toluenesulfonate, di(4-methoxyphenyl).p-tolylsulfonium benzenesulfonate, di(4-methoxyphenyl).p-tolylsulfonium 10-camphorsulfonate, di(4-methoxyphenyl).p-tolylsulfonium n-octanesulfonate, di(4-methoxyphenyl).p-tolylsulfonium 2-trifluoromethylbenzenesulfonate, di(4-methoxyphenyl).p-tolylsulfonium 4-trifluoromethylbenzenesulfonate, di(4-methoxyphenyl).p-tolylsulfonium perfluorobenzenesulfonate, phenyl.biphenylenesulfonium trifluoromethanesulfonate, phenyl.biphenylenesulfonium pyrenesulfonate, phenyl.biphenylenesulfonium n-dodecylbenzenesulfonate, phenyl.biphenylenesulfonium p-toluenesulfonate, phenyl.biphenylenesulfonium benzenesulfonate, phenyl.biphenylenesulfonium 10-camphorsulfonate, phenyl.biphenylenesulfonium n-octanesulfonate, phenyl.biphenylenesulfonium 2-trifluoromethylbenzenesulfonate, phenyl.biphenylenesulfonium 4-trifluoromethylbenzenesulfonate, phenyl.biphenylenesulfonium perfluorobenzenesulfonate, (4-phenylthiophenyl).diphenylsulfonium trifluoromethanesulfonate, (4-phenylthiophenyl).diphenylsulfonium pyrenesulfonate, (4-phenylthiophenyl).diphenylsulfonium n-dodecylbenzenesulfonate, (4-phenylthiophenyl).diphenylsulfonium p-toluenesulfonate, (4-phenylthiophenyl).diphenylsulfonium benzenesulfonate, (4-phenylthiophenyl).diphenylsulfonium 10-camphorsulfonate, (4-phenylthiophenyl).diphenylsulfonium n-octanesulfonate, (4-phenylthiophenyl).diphenylsulfonium 2-trifluoromethylbenzenesulfonate, (4-phenylthiophenyl).diphenylsulfonium 4-trifluoromethylbenzenesulfonate, (4-phenylthiophenyl).diphenylsulfonium perfltiorobenzenesulfonate, 4,4'-bis(diphenylsulfoniophenyl)sulfide di(trifluoromethanesulfonate), 4,4'-bis(diphenylsulfoniophenyl)sulfide di(pyrenesulfonate), 4,4'-bis(diphenylsulfoniophenyl)sulfide di(n-dodecylbenzenesulfonate), 4,4'-bis(diphenylsulfoniophenyl)sulfide di(p-toluenesulfonate), 4,4'-bis(diphenylsulfoniophenyl)sulfide di(benzenesulfonate), 4,4'-bis(diphenylsulfoniophenyl)sulfide di(10-camphorsulfonate), 4,4'-bis(diphenylsulfoniophenyl)sulfide di(n-octanesulfonate), 4,4'-bis(diphenylsulfoniophenyl)sulfide di(2-trifluoromethylbenzenesulfonate), 4,4'-bis(diphenylsulfoniophenyl)sulfide di(4-trifluoromethylbenzenesulfonate), 4,4'-bis(diphenylsulfoniophenyl)sulfide di(perfluorobenzenesulfonate), 1-phenyltetrahydrothiophenium trifluoromethanesulfonate, 1-(4-hydroxyphenyl)tetrahydrothiophenium trifluoromethanesulfonate, 1-(3,5-dimethyl-4-hydroxyphenyl)tetrahydrothiophenium trifluoromethanesulfonate, 1-(4-n-butoxyphenyl) tetrahydrothiophenium trifluoromethanesulfonate, 1-(4-hydroxynaphthalen-1-yl)tetrahydrothiophenium trifluoromethanesulfonate, 1-(4-methoxynaphthalen-1-yl) tetrahydrothiophenium trifluoromethanesulfonate, 1-(4-ethoxynaphthalen-1-yl)tetrahydrothiophenium trifluoromethanesulfonate, 1-(4-n-butoxynaphthalen-1-yl) tetrahydrothiophenium trifluoromethanesulfonate, 1-(4-methoxymethoxynaphthalen-1-yl)tetrahydrothiophenium trifluoromethanesulfonate, 1-(4-ethoxymethoxynaphthalen-1-yl)tetrahydrothiophenium trifluoromethanesulfonate, 1-[4-(1-methoxyethoxy)naphthalen-1-yl] tetrahydrothiophenium trifluoromethanesulfonate, 1-[4-(2-methoxyethoxy)naphthalen-1-yl]tetrahydrothiophenium trifluoromethanesulfonate, 1-[4-(2-methoxyethoxy) naphthalen-1-yl]tetrahydrothiophenium nonafluoro-n-butanesulfonate, 1-[4-(2-methoxyethoxy)naphthalen-1-yl] tetrahydrothiophenium perfluoro-n-octanesulfonate, 1-(4-methoxycarbonyloxynaphthalen-1-yl) tetrahydrothiophenium trifluoromethanesulfonate, 1-(4-ethoxycarbonyloxynaphthalen-1-yl)tetrahydrothiophenium trifluoromethanesulfonate, 1-(4-n-propoxycarbonyloxynaphthalen-1-yl) tetrahydrothiophenium trifluoromethanesulfonate, 1-(4-i-propoxycarbonyloxynaphthalen-1-yl) tetrahydrothiophenium trifluoromethanesulfonate, 1-(4-n-butoxycarbonyloxynaphthalen-1-yl)tetrahydrothiophenium trifluoromethanesulfonate, 1-(4-t-butoxycarbonyloxynaphthalen-1-yl)tetrahydrothiophenium trifluoromethanesulfonate, 1-(4-benzyloxynaphthalen-1-yl) tetrahydrothiophenium trifluoromethanesulfonate, 1-(2-naphthalen-1-yl-2-oxoethyl)tetrahydrothiophenium trifluoromethanesulfonate, 1-[4-(2-tetrahydrofuranyloxy) naphthalen-1-yl]tetrahydrothiophenium trifluoromethanesulfonate, 1-[4-(2-tetrahydropyranyloxy) naphthalen-1-yl]tetrahydrothiophenium trifluoromethanesulfonate, and the like can be given.

<Sulfone Compounds>

As examples of sulfone compounds, b-ketosulfone, b-sulfonylsulfone, and a-diazo compounds of these compounds can be given.

As specific examples of sulfone compounds, phenacylphenylsulfone, mesitylphenacylsulfone, bis(phenylsulfonyl)methane, and 4-trisphenacylsulfone can be given.

<Sulfonate Compounds>

As examples of sulfonate compounds, alkyl sulfonate, haloalkyl sulfonate, aryl sulfonate, and imino sulfonate can be given.

As specific examples of sulfonate compounds, benzointosylate, pyrogallol methanetrisulfonate, nitrobenzyl-9,10-diethoxyanthracene-2-sulfonate, a-methylolbenzointosylate, a-methylolbenzoin trifluoromethanesulfonate, a-methylolbenzoin n-octanesulfonate, a-methylolbenzoin dodecylsulfonate, and the like can be given.

<Disulfonyldiazomethane Compound>

As examples of disulfonyldiazomethane compounds, a compound shown by the following formula (29) and the like can be given:

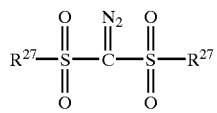

(29)

wherein $R^{27}$ individually represents a monovalent group such as an alkyl group, aryl group, halogenated alkyl group, and halogenated aryl group.

As specific examples of disulfonyldiazomethane compounds, bis(trifluoromethylsulfonyl)diazomethane, bis(cyclohexylsulfonyl)diazomethane, bis(phenylsulfonyl)diazomethane, bis(p-toluenesulfonyl)diazomethane, bis(2,4-dimethylbenzenesulfonyl)diazomethane, methylsulfonyl p-toluenesulfonyldiazomethane, bis(4-t-butylphenylsulfonyl)diazomethane, bis(4-chlorobenzenesulfonyl)diazomethane, (cyclohexylsulfonyl)(p-toluenesulfonyl)diazomethane, (cyclohexylsulfonyl)(1,1-dimethylethylsulfonyl)diazomethane, bis(1,1-dimethylethylsulfonyl)diazomethane, bis(1-methylethylsulfonyl)diazomethane, bis(3,3-dimethyl-1,5-dioxaspiro[5.5]dodecane-8-sulfonyl)diazomethane, bis(1,4-dioxaspiro[4.5]decane-7-sulfonyl)diazomethane, and the like can be given.

<Disulfonylmethane Compound>

As examples of disulfonylmethane compounds, a compound shown by the following formula (30) and the like can be given:

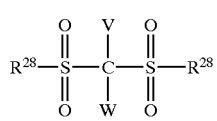

(30)

wherein $R^{28}$ individually represent a linear or branched monovalent aliphatic hydrocarbon group, a cycloalkyl group, aryl group, aralkyl group, or other monovalent organic groups having a hetero atom, V and W individually represent an aryl group, a hydrogen atom, a linear or branched monovalent aliphatic hydrocarbon group, or other monovalent organic groups having a hetero atom, provided that at least one of V and W represents an aryl group, or V and W bond to form a monocyclic or polycyclic ring having at least one unsaturated bond, or V and W bond to form a group shown by the following formula (31):

(31)

wherein V' and W' individually represent a hydrogen atom, halogen atom, an alkyl group, cycloalkyl group, aryl group, or aralkyl group, or V' and W' each bonded to the same or different carbon atoms bond to form a monocyclic carbon structure, and b is an integer from 2 to 10.

<Oxime Sulfonate Compounds>

As examples of oxime sulfonate compounds, compounds of the following formulas (32-1) or (32-2) can be given:

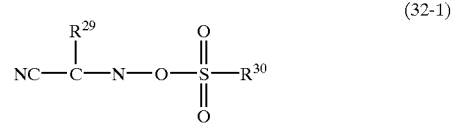

(32-1)

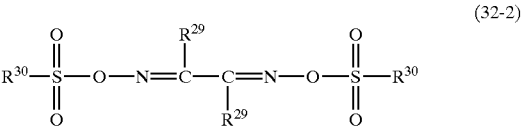

(32-2)

wherein $R^{29}$ and $R^{30}$ individually represent a monovalent organic group, and when two $R^{29}$ and $R^{30}$ groups are present, such groups may be identical or different.

As specific examples of $R^{29}$ in the formula (32-1) and (32-2), a methyl group, ethyl group, n-propyl group, phenyl group, tosyl group, and the like can be given.

As specific examples of $R^{30}$ in the formula (32-1) and (32-2), a phenyl group, tosyl group, naphthyl group, and the like can be given.

<Hydrazinesulfonate Compounds>

As examples of hydrazinesulfonate compounds, bis(benzene)sulfonylhydrazine, bis(p-toluene)sulfonylhydrazine, bis(trifluoromethane)sulfonylhydrazine, bis(nonafluoro-n-butane)sulfonylhydrazine, bis(n-propane)sulfonylhydrazine, benzenesulfonylhydrazine, p-toluenesulfonylhydrazine, trifluoromethanesulfonylhydrazine, nonafluoro-n-butanesulfonylhydrazine, n-propanesulfonylhydrazine, trifluoromethanesulfonyl p-toluenesulfonylhydrazine, and the like can be given.

Of these other acid generators, di(t-butylphenyl)iodonium trifluoromethanesulfonate, di(t-butylphenyl) 10-camphorsulfonate, triphenylsulfonium trifluoromethanesulfonate, triphenylsulfonium 10-camphorsulfonate, N-(trifluoromethylsulfonyloxy)-7-oxabicyclo[2.2.1]hept-5-ene-2,3-dicarboxyimide, N-(10-camphorsulfonyloxy)succinimide, and the like are preferable.

These other acid generators may be used either individually or in combination of two or more.

In the radiation-sensitive resin compositions (i)–(iii), the proportion of the other acid generators to be used is preferably 90 wt % or less, and particularly preferably 80 wt % or less for 100 wt % of the total amount of the acid generator (I) and other acid generators.

Although the proportion of the components in the positive-tone radiation-sensitive resin composition (i), positive-tone radiation-sensitive resin composition (ii), and the negative-tone radiation-sensitive resin composition (iii) varies according to the characteristics desired for the resist, a preferable proportion is as follows.

For the positive-tone radiation-sensitive resin composition (i) and the positive-tone radiation-sensitive resin composition (ii), the amount of the acid generator (I) to be added is preferably 0.01–70 parts by weight, still more preferably 0.1–50 parts by weight, and particularly preferably 0.5–20 parts by weight for 100 parts by weight of the acid-cleavable group-containing resin or alkali-soluble resin. The amount of the acid generator (I) less than 0.01 part by weight may impair sensitivity and resolution. If the amount exceeds 70 parts by weight, resist coating properties and pattern configuration tend to be adversely affected.

For the positive-tone radiation-sensitive resin composition (ii), the amount of the alkali solubility control agent to be added is preferably 5–150 parts by weight, still more preferably 5–100 parts by weight, and particularly preferably 5–50 parts by weight for 100 parts by weight of the alkali-soluble resin. The amount of alkali solubility control agent less than 5 parts by weight may decrease the rate of residual coatings and induce swelling of patterns. If the amount exceeds 150 parts by weight, coating surface roughening and decrease in the coating surface strength tends to occur.

For the negative-tone radiation-sensitive resin composition (iii), the amount of the acid generator (I) to be added is preferably 0.01–70 parts by weight, still more preferably 0.1–50 parts by weight, and particularly preferably 0.5–20 parts by weight for 100 parts by weight of the alkali-soluble resin. The amount of the acid generator (I) less than 0.01 part by weight may impair sensitivity and resolution. If the amount exceeds 70 parts by weight, resist coating properties and pattern configuration tend to be adversely affected.

The amount of the crosslinking agent (E) to be added is preferably 5–95 parts by weight, still more preferably 15–85 parts by weight, and particularly preferably 20–75 parts by weight for 100 parts by weight of the alkali-soluble resin. The amount of the crosslinking agent (E) less than 5 parts by weight may decrease the rate of residual coatings and tends to induce meandering and swelling of the patterns. If the amount exceeds 95 parts by weight, developability of exposed areas tends to decrease.

Other Components

<Acid Diffusion Controller>

It is preferable to add an acid diffusion controller to the positive-tone radiation-sensitive resin composition (i), positive-tone radiation-sensitive resin composition (ii), and negative-tone radiation-sensitive resin composition (iii). The acid diffusion controller controls diffusion of an acid generated from the acid generator upon exposure in the resist coating to hinder unfavorable chemical reactions in the unexposed area.

The addition of the acid diffusion controller improves storage stability of the composition and resolution as a resist. Moreover, the addition of the acid diffusion controller prevents the line width of the resist pattern from changing due to variation of post-exposure delay (PED) from exposure to post-exposure heat treatment, whereby a composition with remarkably superior process stability can be obtained.

As the acid diffusion controller, organic compounds containing nitrogen of which the basicity does not change during exposure or heating for forming a resist pattern are preferable.

As examples of such nitrogen-containing organic compounds, a compound shown by the following formula (33) (hereinafter called "nitrogen-containing compound (α)"),

(33)

wherein $R^{31}$ individually represents a hydrogen atom, alkyl group, aryl group, or aralkyl group which are either unsubstituted or substituted by a functional group such as a hydroxy group.

A diamino compound having two nitrogen atoms in the molecule (hereinafter referred to as "nitrogen-containing compound (β)"), a diamino polymer having three or more nitrogen atoms in the molecule (hereinafter referred to as "nitrogen-containing compound (γ)"), an amide group-containing compound, urea compound, and nitrogen-containing heterocyclic compound can be given.

Examples of the nitrogen-containing compound (α) include monoalkylamines such as n-hexylamine, n-heptylamine, n-octylamine, n-nonylamine, and n-decylamine; dialkylamines such as di-n-butylamine, di-n-pentylamine, di-n-hexylamine, di-n-heptylamine, di-n-octylamine, di-n-nonylamine, and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, and tri-n-decylamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Examples of the nitrogen-containing compounds (β) include ethylenediamine, N,N,N',N'-tetramethylethylenediamine, N,N,N',N'-tetrakis(2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Examples of the nitrogen-containing compounds (γ) include polyethyleneimine, polyallylamine, a polymer of dimethylaminoethylacrylamide, and the like.

Examples of compounds containing an amide group include formamide, N-methylformamide, N,N-dimethylformamide, acetamide, N-methylacetamide, N,N-dimethylacetamide, propionamide, benzamide, pyrrolidone, and N-methylpyrrolidone.

Examples of urea compounds include urea, methylurea, 1,1-dimethylurea, 1,3-dimethylurea, 1,1,3,3-tetramethylurea, 1,3-diphenylurea, and tributylthiourea.

Examples of the nitrogen-containing heterocyclic compounds include imidazoles such as imidazole, 4-methylimidazole, 4-methyl-2-phenylimidazole, benzimidazole and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, N-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, morpholine, 4-methylmorpholine, piperazine, 1,4-dimethylpiperazine, 1,4-diazabicyclo[2.2.2]octane, phenanthroline, and the like.

A nitrogen-containing compound having an acid-cleavable group can also be used as a nitrogen-containing organic compound.

As examples of the nitrogen-containing compound having an acid-cleavable group, N-(t-butoxycarbonyl)piperidine, N-(t-butoxycarbonyl)imidazole, N-(t-butoxycarbonyl) benzimidazole, N-(t-butoxycarbonyl)-2-phenylbenzimidazole, N-(t-butoxycarbonyl)dioctylamine, N-(t-butoxycarbonyl)diethanolamine, N-(t-butoxycarbonyl) dicyclohexylamine, N-(t-butoxycarbonyl)diphenylamine, and the like can be given.

Of these nitrogen-containing organic compounds, the nitrogen-containing compounds ($\alpha$), nitrogen-containing compounds ($\beta$), nitrogen-containing heterocyclic compound, and nitrogen-containing compounds having an acid-cleavable group and the like are preferable.

The acid diffusion controller may be used either individually or in combination of two or more.

The amount of the acid diffusion controller to be added is usually 15 parts by weight or less, preferably 0.001–10 parts by weight, and still more preferably 0.005–5 parts by weight for 100 parts by weight of the acid-cleavable group-containing resin or alkali-soluble resin. If the proportion of the acid diffusion controller exceeds 15 parts by weight, sensitivity as a resist and developability of the exposed area tend to decrease. If the amount is less than 0.001 part by weight, the pattern shape or dimensional accuracy as a resist may decrease depending on the processing conditions.

<Alkali-Soluble Resin>

An alkali-soluble resin (hereinafter referred to as "alkali-soluble resin (c)") can be optionally added to the positive-tone radiation-sensitive resin composition (i).

As examples of the alkali-soluble resin (c), poly(4-hydroxystyrene), partially hydrogenated poly(4-hydroxystyrene), poly(3-hydroxystyrene), partially hydrogenated poly(3-hydroxystyrene), 4-hydroxystyrene/3-hydroxystyrene copolymer, 4-hydroxystyrene/styrene copolymer, novolac resin, polyvinyl alcohol, polyacrytic acid, and the like can be given.

Mw of the alkali-soluble resin (c) is 1,000–1,000,000, and preferably 2,000–100,000.

These alkali-soluble resins (c) may be used either individually or in combination of two or more.

The amount of alkali-soluble resins (c) to be added is preferably 30 parts by weight or less for 100 parts by weight of the acid-cleavable group-containing resin.

<Surfactant>

Surfactants exhibiting an action of improving the applicability or striation of the composition and developability as a resist may be added to the positive-tone radiation-sensitive resin composition (i), positive-tone radiation-sensitive resin composition (ii), and negative-tone radiation-sensitive resin composition (iii).

Examples of such surfactants include polyoxyethylene lauryl ether, polyoxyethylene stearyl ether, polyoxyethylene oleyl ether, polyoxyethylene n-octyl phenol ether, polyoxyethylene n-nonyl phenol ether, polyethylene glycol dilaurate, polyethylene glycol distearate; and commercially available products such as FTOP EF301, EF303, EF352 (manufactured by TOHKEM PRODUCTS CORPORATION), MEGAFAC F171, F173 (manufactured by Dainippon Ink and Chemicals, Inc.), Fluorad FC430, FC431 (manufactured by Sumitomo 3M Ltd.), Asahi Guard AG710, Surflon S-382, SC-101, SC-102, SC-103, SC-104, SC-105, SC-106 (manufactured by Asahi Glass Co., Ltd.), KP341 (manufactured by Shin-Etsu Chemical Co., Ltd.), and Polyflow No. 75, No. 95 (manufactured by Kyoeisha Chemical Co., Ltd.).

These surfactants may be used either individually or in combination of two or more.

The amount of the surfactant to be added is preferably 2 parts by weight or less for 100 parts by weight of the acid-cleavable group-containing resin or alkali-soluble resin.

<Photosensitizer>

A photosensitizer may be added to the positive-tone radiation-sensitive resin composition (i), positive-tone radiation-sensitive resin composition (ii), and negative-tone radiation-sensitive resin composition (iii).

As examples of photosensitizers, carbazoles, benzophenones, rose bengals, anthracenes, and the like can be given.

These sensitizers may be used either individually or in combinations of two or more. The amount of the photosensitizer to be added is preferably 50 parts by weight or less for 100 parts by weight of the acid-cleavable group-containing resin or alkali-soluble resin.

<Other Additives>

In addition, a dye and/or a pigment may be added to visualize latent images of exposed areas and to reduce the effect of halation during exposure. An adhesion adjuvant may be added to improve adhesion to the substrate.

As other additives, halation inhibitors such as 4-hydroxy-4'-methylchalcone, form improvers, preservation stabilizers, antifoaming agents, and the like can be added.

Solvent

The positive-tone radiation-sensitive resin composition (i), positive-tone radiation-sensitive resin composition (ii), and negative-tone radiation-sensitive resin composition (iii) are used as a composition solution. Such a composition solution is prepared by homogeneously dissolving the composition in a solvent so that the total solid concentration is 0.1–50 wt %, and preferably 1–40 wt %, and filtering the solution through a filter with a pore diameter of about 0.2 mm.

Examples of solvents used for preparation of the composition solution include:

ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate;

propylene glycol monoalkyl ethers such as propylene glycol monomethyl ether, propylene glycol monoethyl ether, propylene glycol mono-n-propyl ether, and propylene glycol mono-n-butyl ether;

propylene glycol dialkyl ethers such as propylene glycol dimethyl ether, propylene glycol diethyl ether, propylene glycol di-n-propyl ether, and propylene glycol di-n-butyl ether;

propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate;

lactic acid esters such as methyl lactate, ethyl lactate, n-propyl lactate, and i-propyl lactate;

aliphatic carboxylic acid esters such as n-amyl formate, i-amyl formate, ethyl acetate, n-propyl acetate, i-propyl acetate, n-butyl acetate, i-butyl acetate, n-amyl acetate, i-amyl acetate, i-propyl propionate, n-butyl propionate, and i-butyl propionate;

other esters such as ethyl hydroxyacetate, ethyl 2-hydroxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, butyl 3-methoxyacetate, butyl 3-methyl-3-methoxyacetate, butyl 3-methyl-3-methoxypropionate, butyl 3-methyl-3-methoxybutyrate, methyl acetoacetate, ethyl acetoacetate, methyl pyruvate, and ethyl pyruvate;

aromatic hydrocarbons such as toluene and xylene;

ketones such as methyl ethyl ketone, methyl propyl ketone, methyl butyl ketone, 2-heptanone, 3-heptanone, 4-heptanone, and cyclohexanone;

amides such as N-methylformamide, N,N-dimethylformamide, N-methylacetamide, N,N-dimethyl acetamide, and N-methylpyrrolidone; and lactones such as g-butyrolactone.

and the like can be given.

These solvents may be used either individually or in combinations of two or more.

Formation of Resist Pattern

A resist pattern is formed from the positive-tone radiation-sensitive resin composition (i), positive-tone radiation-sensitive resin composition (ii), and negative-tone radiation-sensitive resin composition (iii) by applying the composition solution prepared as mentioned above to substrates such as a silicon wafer or a wafer covered with aluminum using an appropriate application method such as rotational coating, cast coating, and roll coating to form a resist coating. The resist coating is then optionally prebaked at a temperature of about 70–160° C. (hereinafter referred to as "PB") and exposed to light through a predetermined mask pattern. As examples of the radiation used here, deep ultraviolet rays such as ultraviolet rays, KrF excimer laser (wavelength: 248 nm), ArF excimer laser (wavelength: 193 nm), $F_2$ excimer laser (wavelength: 157 nm), or EUV (extreme ultraviolet, wavelength: 13 nm), charged particle rays such as electron beams, and X-rays such as synchrotron radiation can be given, with deep ultraviolet rays and electron beams being preferable. The exposure conditions such as the amount of exposure are appropriately determined depending on the composition of the radiation-sensitive resin composition, types of additives, and the like.

In the present invention, it is preferable to perform post-exposure bake (hereinafter referred to as "PEB") at 70–160° C. for 30 seconds or more to consistently form minute resist patterns with high precision. If the heating temperature for PEB is less than 70° C., sensitivity may fluctuate according to the type of substrates.

A desired resist pattern is obtained by developing the resist using an alkaline developer at 10–50° C. for 10–200 seconds, preferably at 15–30° C. for 15–100 seconds, and still more preferably at 20–25° C. for 15–90 seconds.

As the alkaline developer, an alkaline aqueous solution prepared by dissolving an alkali such as an alkali metal hydroxide, aqueous ammonia, mono-, di-, or tri-alkylamine, mono-, di-, or tri-alkanolamine, heterocyclic amine, tetraalkylammonium hydroxide, choline, 1,8-diazabicyclo [5.4.0]-7-undecene, or 1,5-diazabicyclo[4.3.0]-5-nonene to a concentration of 1–10 wt %, preferably 1–5 wt %, and particularly preferably 1–3 wt % can be used.

Moreover, an appropriate amount of a water-soluble organic solvent such as methanol and ethanol or a surfactant can be added to the developer comprising the above alkaline aqueous solution.

When forming a resist pattern, a protective film may be provided on the resist coating in order to prevent an adverse effect of basic impurities and the like which are present in the environmental atmosphere. Also, an antireflection film may be provided on the lower or upper layer.

EXAMPLES

The present invention will be described in more detail by way of examples. However, these examples should not be construed as limiting the present invention.

In the examples, part(s) and % refer to part(s) by weight and wt % unless otherwise indicated.

Synthesis of Acid Generator (I)

Synthesis Example 1

An autoclave was charged with 108.5 g of dicyclopentadiene and 322.4 g of 1-bromo-1,1,2,2-tetrafluoro-3-butene. A solution of 0.3 g of 4-methoxyphenol dissolved in 5 ml of toluene was added to the autoclave as a polymerization inhibitor and the mixture was stirred for 5 hours at 170° C. The reaction product was purified by distillation under reduced pressure at 85° C. and 25 mmHg to obtain 326 g of 1-bromo-1,1,2,2-tetrafluoro-2-(norborn-5-en-2-yl)ethane as a clear liquid (hereinafter referred to as "compound (1-a)").

Next, a solution of 62 g of the compound (1-a) dissolved in 1 liter of ethyl acetate was added to a 2 liter eggplant flask. After the addition of 12 g of alumina containing 5% rhodium, the mixture was stirred vigorously for 3 hours under a hydrogen atmosphere. Then, the reaction solution was filtrated under reduced pressure through a glass filter covered with celite. The filtrate was concentrated under reduced pressure and the concentrate was purified by distillation under reduced pressure to obtain 56 g of 1-bromo-1,1,2,2-tetrafluoro-2-(norbornan-2-yl)ethane as a clear liquid (hereinafter referred to as "compound (1-b)").

A 2 liter three-necked flask, in which the atmosphere was thoroughly replaced with nitrogen, was charged with a solution of 70 g of sodium dithionite and 52 g of sodium hydrogencarbonate dissolved in 300 ml of water. Then, 300 ml of a solution of 55 g of the compound (1-b) dissolved in acetonitrile was added by dripping for one hour at room temperature, and the solution was reacted for two hours at 75° C. After evaporating the acetonitrile under reduced pressure, 350 mg of sodium tungstate dihydrate and 5.0 g of disodium hydrogenphosphate were added. 5.6 ml of 30% hydrogen peroxide aqueous solution was added by dripping at room temperature while carefully maintaining the pH of the reaction solution. The solution was distilled under reduced pressure to remove the water, the residue was extracted with methanol and distilled under reduced pressure to remove the methanol, thereby obtaining 35 g of 1,1,2,2-tetrafluoro-2-(norbornan-2-yl)ethane sodium sulfonate (hereinafter referred to as "compound (1-c)").

Next, 80 g of 1-n-butoxynaphthalene and 212 g of a phosphorus pentoxide-methanesulfonic acid mixture were added to a five liter eggplant flask and the mixture was stirred for 15 minutes at room temperature. 47 g of tetramethylene sulfoxide was added to the mixture by dripping at 0° C. and the mixture was stirred for 20 minutes, then the temperature of the mixture was gradually increased to room temperature. The mixture was stirred for an additional hour. The mixture was again cooled to 0° C. After the addition of 2 liters of water and adjusting the pH to 7.0 using 25% aqueous ammonia, the mixture was stirred for one hour at room temperature. After the addition of a solution of 116 g of the compound (1-c) dissolved in 150 ml of water, the mixture was stirred for an additional hour at room temperature. The reaction solution was extracted with methylene chloride and the extract was washed with water. The methylene chloride was evaporated under reduced pressure and the residue was purified using a silica gel column (methylene chloride:methanol=20:1). 76 g of 1,4-butylene-(1-n-butoxynaphta-4-yl)sulfonium 1,1,2,2-tetrafluoro-2-(norbornan-2-yl)ethane sulfonate was obtained by reprecipitation using methylene chloride/n-hexane.

Figure 2:
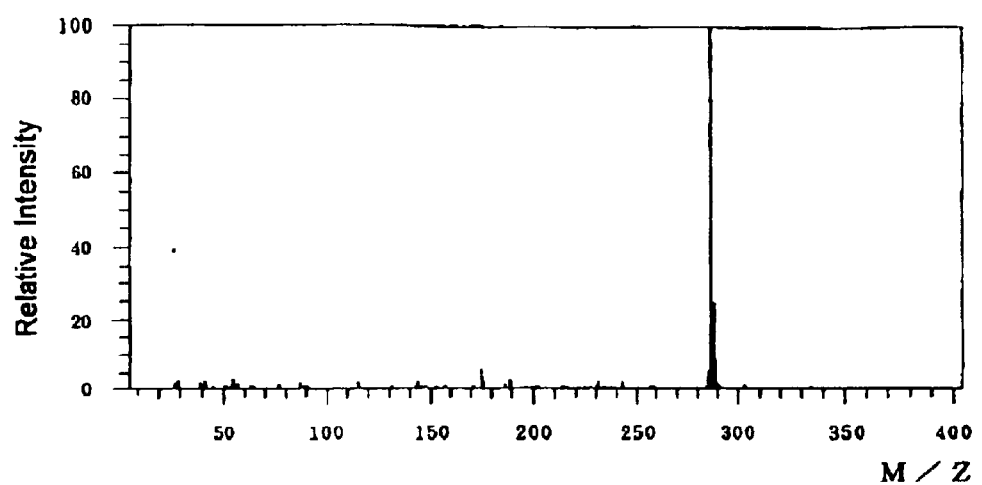
FIG. 2 shows the mass analysis results of the cation moiety of the acid generator (A-1).
Figure 3:
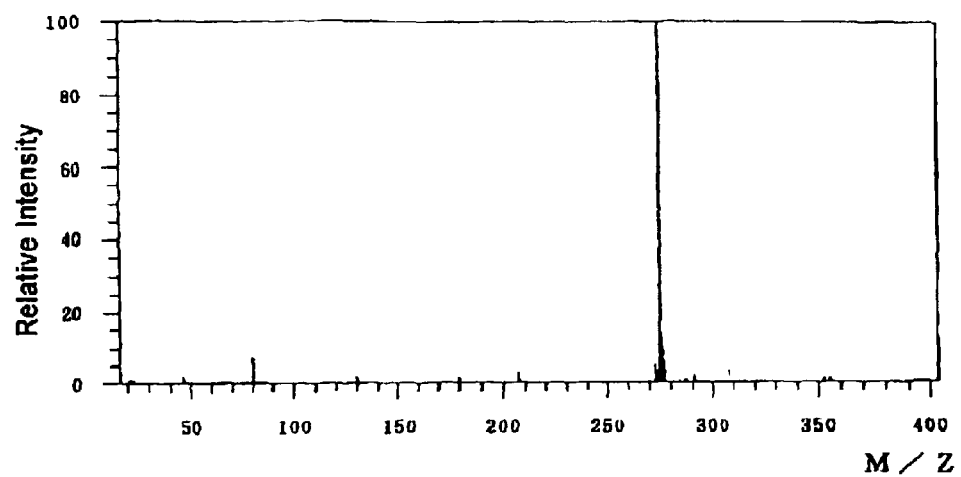
FIG. 3 shows the mass analysis results of the anion moiety of the acid generator (A-1).

The results of ¹H-NMR analysis for this compound are shown in FIG. 1. The results of mass analysis for the cation moiety and anion moiety are shown in FIGS. 2 and 3 respectively.

This compound is referred to as "acid generator (A-1)".

The mass analysis of the acid generator (A-1) and the following acid generators (A-2) to (A-6) was carried out according to the following conditions Apparatus: JMS-AX505W mass spectrometer (manufactured by JEOL, Ltd.)

Emitter current: 5 mA (gas used: Xe)

Acceleration voltage: 3.0 kV

10N MULTI: 1.3

Ionization method: fast atom bombardment (FAB)

Detection ion: cation(+)

Measured mass range: 20–1500 m/z

Scan: 30 sec

Resolution: 1500

Matrix: 3-nitrobenzyl alcohol

Synthesis Example 2

Figure 4:
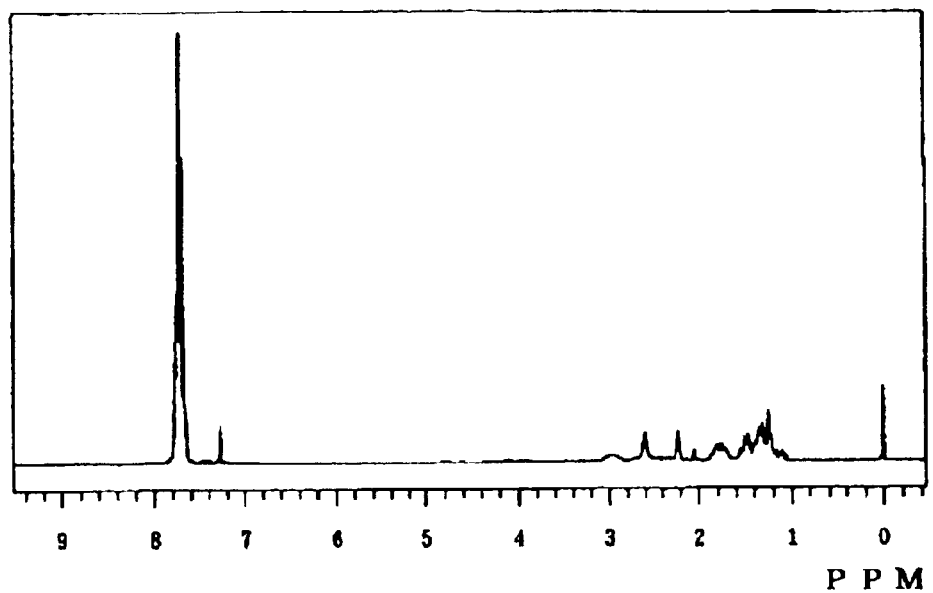
FIG. 4 shows the $^1$H-NMR analysis results of the acid generator (A-2).
Figure 5:
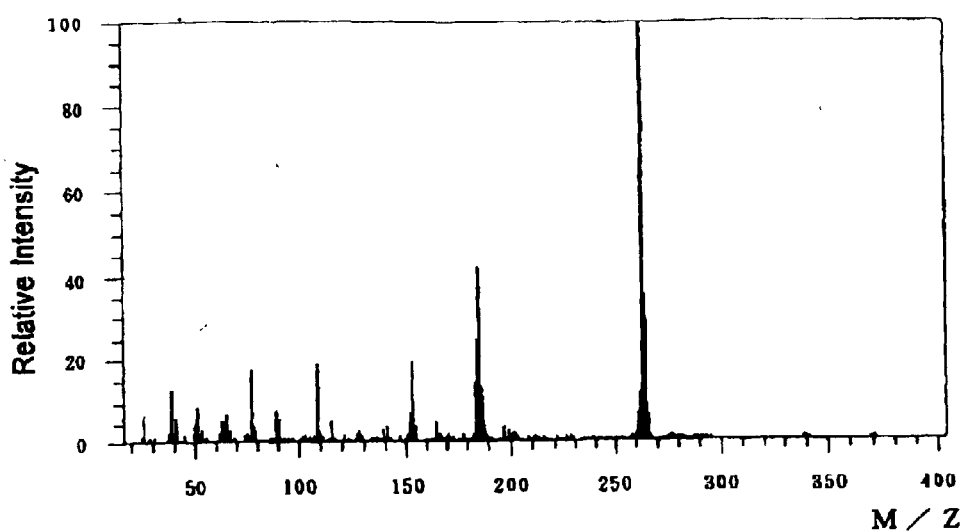
FIG. 5 shows the mass analysis results of the cation moiety of the acid generator (A-2).
Figure 6:
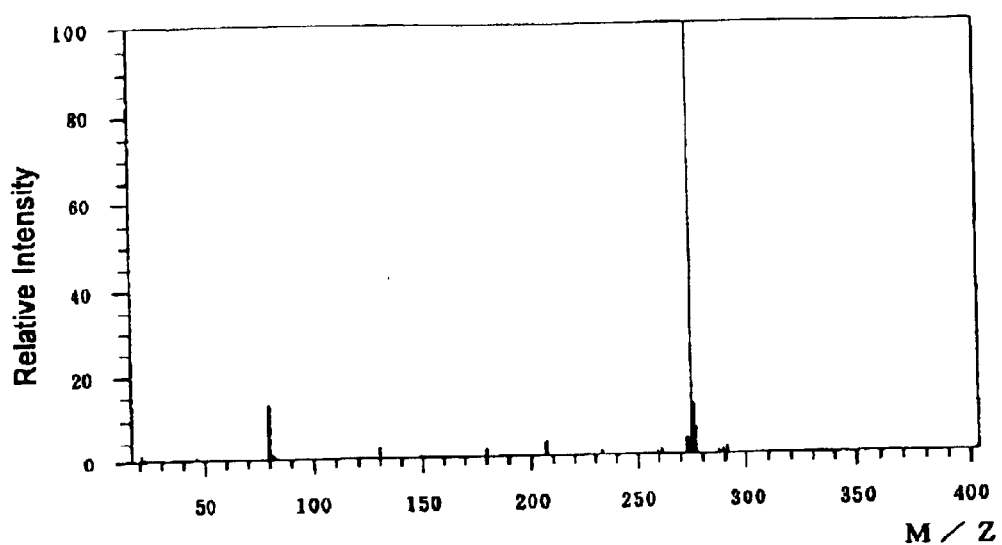
FIG. 6 shows the mass analysis results of the anion moiety of the acid generator (A-2).

A 2 liter eggplant flask was charged with a solution of 20 g of triphenylsulfonium chloride dissolved in 500 ml of water. A 500 ml aqueous solution containing 20 g of the compound (1-d) was added by dripping at room temperature and the mixture was stirred for 30 minutes. The reaction solution was extracted with ethyl acetate and the organic layer was washed twice using water. 16 g of triphenylsulfonium 1,1,2,2-tetrafluoro-2-(norbornan-2-yl)ethane sulfonate was obtained as a clear high viscous oil by concentrating the solution by distillation under reduced pressure. The results of ¹H-NMR analysis for this compound are shown in FIG. 4. The results of mass analysis for the cation moiety and anion moiety are shown in FIGS. 5 and 6 respectively.

This compound is referred to as "acid generator (A-2)".

Synthesis Example 3

A 2 liter eggplant flask was charged with a solution of 20 g of diphenyliodonium chloride dissolved in 1 liter of water. A 500 ml aqueous solution containing 20 g of the compound (1-c) was added by dripping at room temperature and the mixture was stirred for 15 minutes. The deposited crystals were filtered through a glass filter, sufficiently washed with water, and dried under reduced pressure to obtain 12 g of diphenyliodonium 1,1,2,2-tetrafluoro-2-(norbornan-2-yl)ethane sulfonate.

Figure 7:
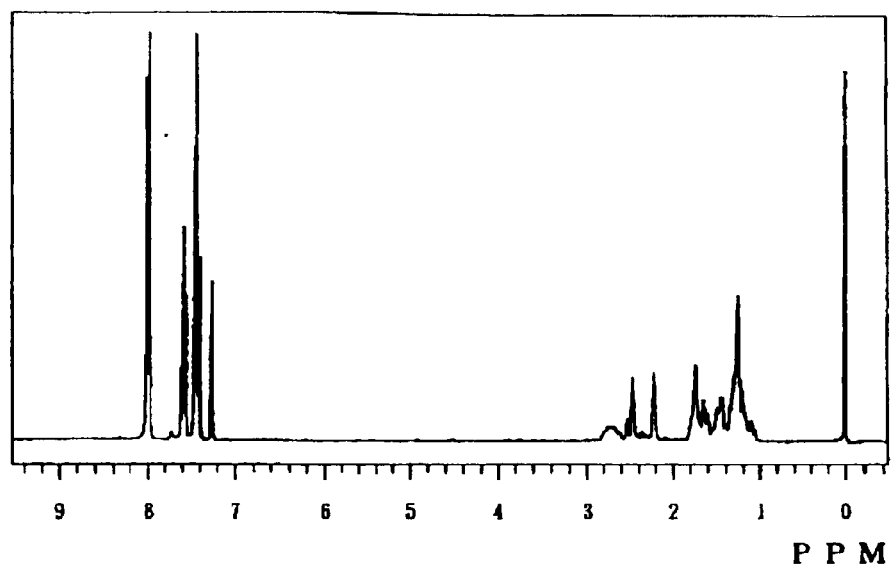
FIG. 7 shows the $^1$H-NMR analysis results of the acid generator (A-3).
Figure 8:
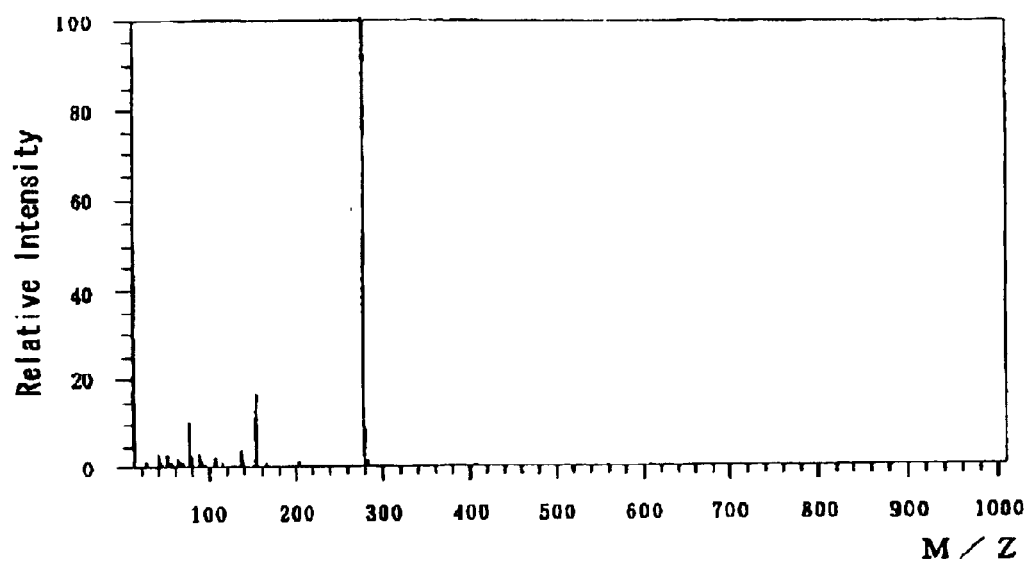
FIG. 8 shows the mass analysis results of the cation moiety of the acid generator (A-3).
Figure 9:
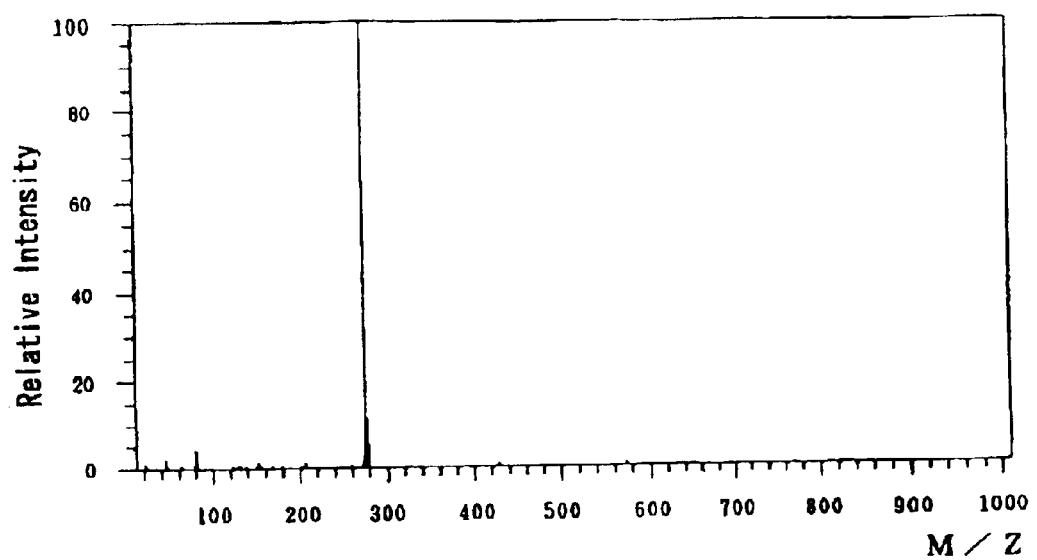
FIG. 9 shows the mass analysis results of the anion moiety of the acid generator (A-3).

The results of ¹H-NMR analysis for this compound are shown in FIG. 7. The results of mass analysis for the cation moiety and anion moiety are shown in FIGS. 8 and 9 respectively.

This compound is referred to as "acid generator (A-3)".

Synthesis Example 4

A 2 liter three-necked flask, in which the atmosphere was thoroughly replaced with nitrogen, was charged with a solution of 70 g of sodium dithionite and 52 g of sodium hydrogencarbonate dissolved in 300 ml of water. 300 ml of a solution of 55 g of the compound (1-b) dissolved in acetonitrile was added by dripping for one hour at room temperature and the mixture was reacted for two hours at 75° C. After evaporating the acetonitrile under reduced pressure, the reaction solution was extracted with ethyl acetate. The organic layer was washed with saturated brine and dried over anhydrous magnesium sulfate. The ethyl acetate was evaporated under reduced pressure to obtain 35 g of 1,1,2,2-tetrafluoro-2-(norbornan-2-yl)ethane sodium sulfonate (hereinafter referred to as "compound (1-d)").

Next, a 2 liter eggplant flask was charged with a solution of 80 g of the compound (1-d) dissolved in 250 ml of water. The solution was bubbled with superfluous chlorine gas for more than 15 minutes while stirring at room temperature. The oily matter collected on the bottom of the flask was extracted with methylene chloride. The organic layer was washed with a sodium hydrogencarbonate aqueous solution and dried over anhydrous magnesium sulfate. The methylene chloride was evaporated under reduced pressure to obtain 68 g of 1,1,2,2-tetrafluoro-2-(norbornan-2-yl)ethane sulfonyl chloride (hereinafter referred to as "compound (4-a)").

Next, after adding 22 g of N-hydroxy-5-norbornene-2,3-dicarboxyimide to a solution of 30 g of the compound (4-a) dissolved in 150 g of tetrahydrofuran, 29 g of triethylamine was added to the mixture by dripping. After stirring the reaction solution for 10 minutes at room temperature, water was added by dripping to obtain the reaction product as white crystals. After filtering, the crystals were dissolved in methylene chloride and the solution was consecutively washed with sodium hydrogencarbonate aqueous solution, oxalic acid aqueous solution, and water. After drying the solution over anhydrous magnesium sulfate, the methylene chloride was evaporated under reduced pressure to obtain 35 g of N-(1,1,2,2-tetrafluoro-2-(norbornan-2-yl)ethylsulfonyloxy)-5-norbornene-2,3-dicarboxyimide.

Figure 10:
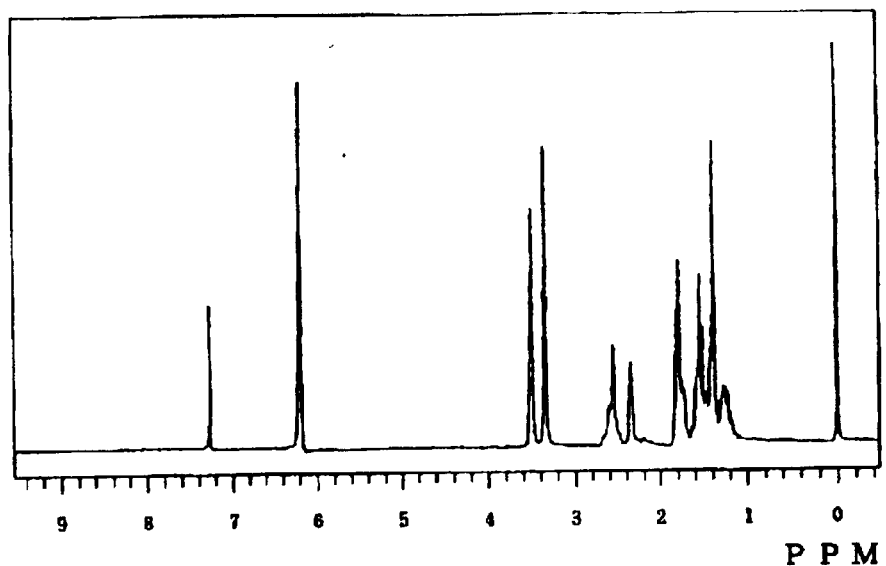
FIG. 10 shows the $^1$H-NMR analysis results of the acid generator (A-4).

FIG. 10 shows the ¹H-NMR analysis results of this compound.

This compound is referred to as "acid generator (A-4)".

Synthesis Example 5

An autoclave was charged with 108.5 g of dicyclopentadiene and 322.4 g of 1-bromo-1,1,2,2-tetrafluoro-3-butene. A solution of 0.3 g of 4-methoxyphenol dissolved in 5 ml of toluene was added to the autoclave as a polymerization inhibitor and the mixture was stirred for 5 hours at 170° C. The reaction product was purified by distillation under reduced pressure at 85° C. and 0.1 mmHg to obtain 226 g of 1-bromo-1,1,2,2-tetrafluoro-2-(tetracyclo[$4.4.0.1^{2,5}.1^{7,10}$]dodec-3-en-8-yl)ethane as a clear liquid (hereinafter referred to as "compound (5-a)").

Next, a solution of 93 g of the compound (5-a) dissolved in 1.5 liters of ethyl acetate was added to a 3 liter eggplant flask. After the addition of 18 g of alumina containing 5% rhodium, the mixture was stirred vigorously for 3 hours under a hydrogen atmosphere. Then, the reaction solution was filtrated under reduced pressure through a glass filter covered with celite. The filtrate was concentrated under reduced pressure and the concentrate was purified by distillation under reduced pressure to obtain 85 g of 1-bromo-1,1,2,2-tetrafluoro-2-(tetracyclo[$4.4.0.1^{2,5}.1^{7,10}$]dodecan-8-yl)ethane as a clear liquid (hereinafter referred to as "compound (5-b)").

A 2 liter three-necked flask, in which the atmosphere was thoroughly replaced with nitrogen, was charged with a solution of 10.2 g of sodium dithionite and 7.4 g of sodium hydrogencarbonate dissolved in 170 ml of water. Then, a solution of 10 g of the compound (5-b) dissolved in 750 ml of acetonitrile was added by dripping for one hour at room temperature, and the solution was reacted for seven hours at 100° C. After precipitating the acetonitrile, the aqueous solution was filtrated and the filtrate was concentrated under reduced pressure. The residue was extracted with methanol and distilled under reduced pressure to remove the methanol, thereby obtaining 10.2 g of 1,1,2,2-tetrafluoro-2-(tetracyclo[4.4.0.1$^{2,5}$.1$^{7,10}$]dodecan-8-yl)ethane sodium sulfinate (hereinafter referred to as "compound (5-c)").

Next, a 500 ml three-necked flask was charged with a solution of 9 g of the compound (5-c) dissolved in 75 ml of water. 50 mg of sodium tungstate dihydrate and 1.2 g of disodium hydrogenphosphate were added. 3 ml of 30% hydrogen peroxide aqueous solution was added by dripping at room temperature while carefully maintaining the pH of the reaction solution. The mixture was reacted for one hour at 60° C., 100 ml of water was added and the mixture was cooled to room temperature. Then, a solution of 10 g of triphenylsulfonium chloride dissolved in 250 ml of water was added by dripping at room temperature and the reaction solution was stirred for one hour. Next, the reaction solution was extracted with ethyl acetate and the organic layer was washed three times using water. The ethyl acetate was removed under reduced pressure and the residue was purified using a silica gel column (methylene chloride:methanol=8:1) to obtain 1 g of triphenylsulfonium 1,1,2,2-tetrafluoro-2-(tetracyclo[4.4.0.1$^{2,5}$.1$^{7,10}$]dodecan-8-yl)ethane sulfonate.

Figure 11:
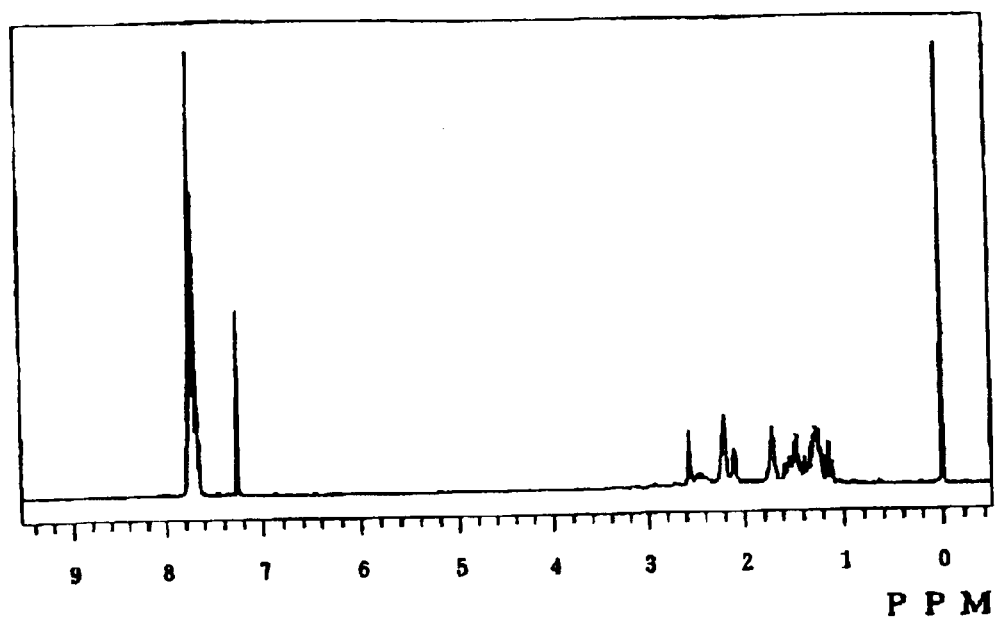
FIG. 11 shows the $^1$H-NMR analysis results of the acid generator (A-5).
Figure 12:
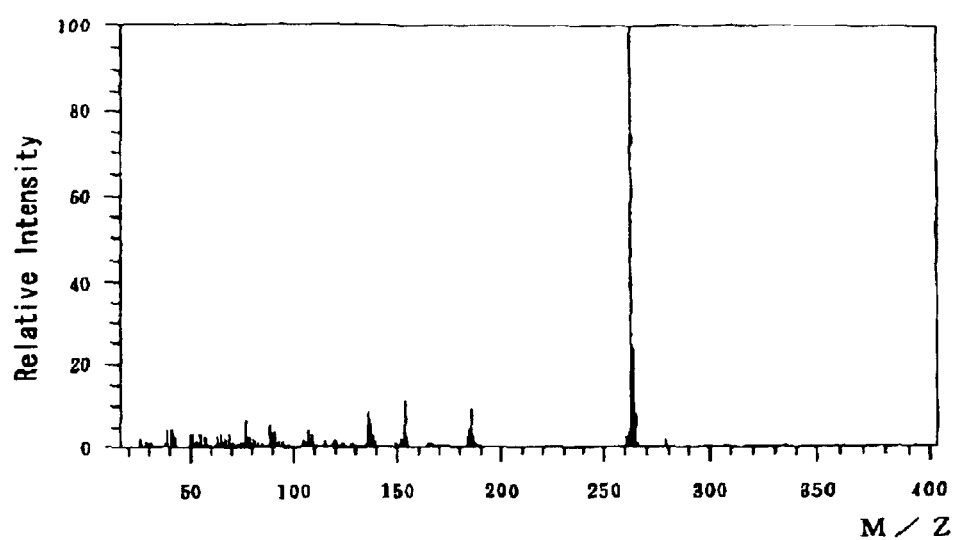
FIG. 12 shows the mass analysis results of the cation moiety of the acid generator (A-5).
Figure 13:
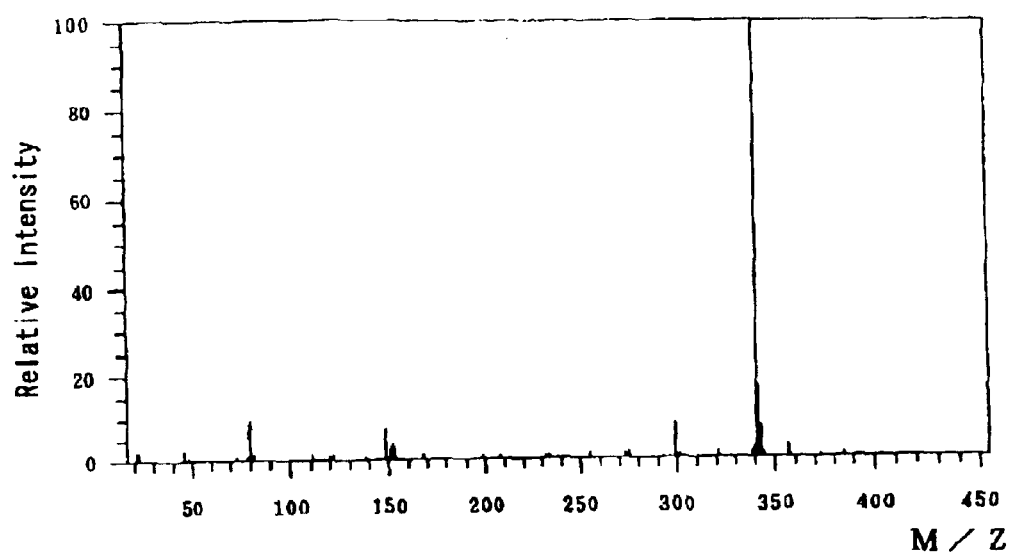
FIG. 13 shows the mass analysis results of the anion moiety of the acid generator (A-5).

The results of $^1$H-NMR analysis for this compound are shown in FIG. 11. The results of mass analysis for the cation moiety and anion moiety are shown in FIGS. 12 and 13 respectively.

This compound is referred to as "acid generator (A-5)".

Synthesis Example 6

A 2 liter eggplant flask was charged with a solution of 25.2 g of sodium hydrogencarbonate dissolved in 500 ml of water. 19.2 g of 2-(fluorosulfonyl)difluoromethyl acetate was added by dripping while stirring the solution at room temperature. Then, the mixture was stirred for a further 2 hours at room temperature, followed by evaporation of water under reduced pressure. The resulting solid was dried overnight under vacuum at room temperature, purified by extraction with 200 ml of methanol, and dried under vacuum at room temperature to obtain 0.34 g of methoxycarbonyldifluoromethane sodium sulfonate (hereinafter referred to as "compound (6-a)").

Next, a solution of 0.478 g of triphenylsulfoniumchloride dissolved in 5 ml of water was added to a solution of 0.34 g of the compound (6-a) dissolved in 15 ml of water. This mixed solution was extracted twice with 20 ml of ethyl acetate. The organic layer was washed with 20 ml of water and dried over anhydrous sodium sulfate. The ethyl acetate was removed by evaporation under reduced pressure and the residue was dried under vacuum to obtain 0.25 g of a highly viscous and oily triphenylsulfonium methoxycarbonyl difluoromethane sulfonate.

Figure 14:
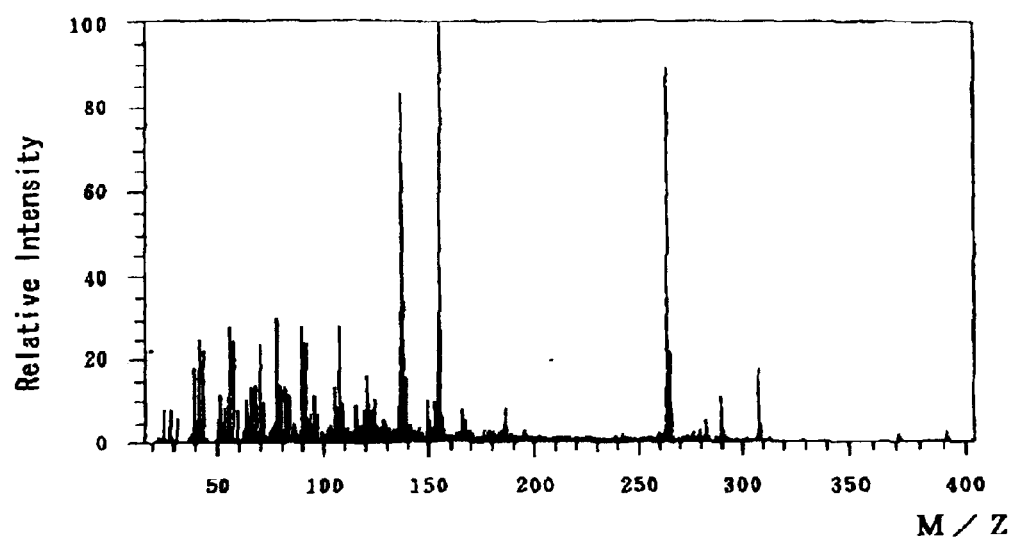
FIG. 14 shows the mass analysis results of the cation moiety of the acid generator (A-6).
Figure 15:
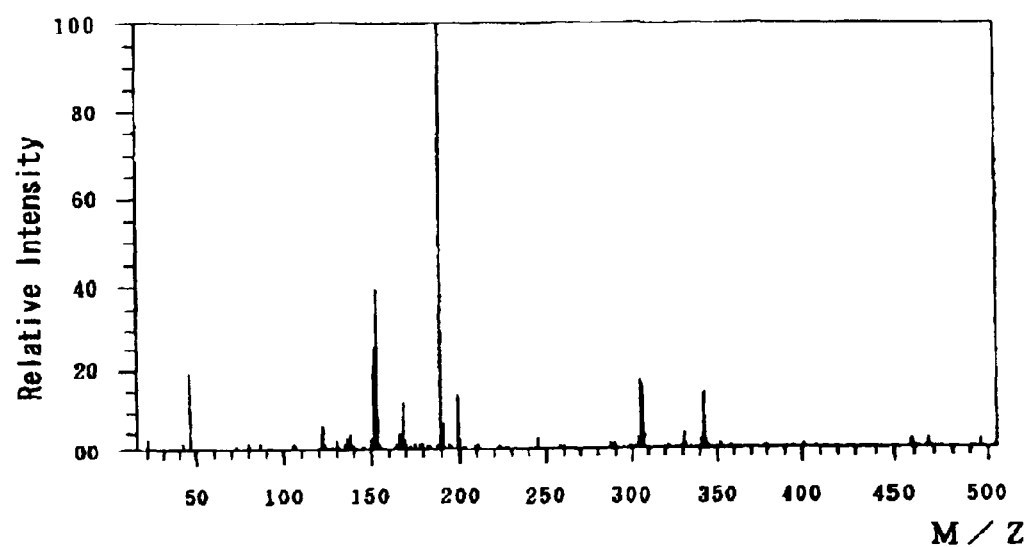
FIG. 15 shows the mass analysis results of the anion moiety of the acid generator (A-6).

The mass analysis results of the cation moiety and anion moiety of this compound are shown in FIGS. 14 and 15 respectively.

This compound is referred to as "acid generator (A-6)".

Synthesis Example 7

A 2 liter eggplant flask was charged with a solution of 20 g of 1-(4-hydroxy-3,5-dimethylphenyl) tetrahydrothiophenium methanesulfonate dissolved in 500 ml of water. A 500 ml aqueous solution containing 20 g of the compound (1-c) was added by dripping at room temperature and the mixture was stirred for 15 minutes. The precipitated crystals were filtered through a glass filter and dissolved in methylene chloride. The solution was added to hexane by dripping to obtain a white precipitate. The resulting precipitate was again filtered through a glass filter and collected. The collected solid was dissolved in acetone and the solution was added to water by dripping to obtain a white precipitate. The precipitate was again filtered through a glass filter, collected, and dried under reduced pressure to obtain 16 g of 1-(4-hydroxy-3,5-dimethylphenyl) tetrahydrothiophenium 1,1,2,2-tetrafluoro-2-(norbornan-2-yl)ethane sulfonate.

FIG. 16 shows the $^1$H-NMR analysis results of this compound.

This compound is referred to as "acid generator (A-7)".

Synthesis Example 8

A 2 liter eggplant flask was charged with a solution of 20 g of the compound (1-c) dissolved in 1,000 ml of a methanol/water(70/30) mixed solvent. While stirring the solution at room temperature, a solution of 36 g of bis(4-t-butylphenyl)iodonium hydrogensulfate dissolved in 1 liter of methanol was added by dripping. Then, the mixture was stirred for an additional 1 hour at room temperature and left to stand for one day. The organic substance in the reaction solution was extracted with methylene chloride. The organic layer was washed with water and dried over anhydrous magnesium sulfate. The product was dissolved in methylene chloride and the solution was added to hexane by dripping to obtain white crystals. The crystals were filtered through a glass filter and dried under reduced pressure to obtain 18 g of bis(4-t-butylphenyl)iodonium 1,1,2,2-tetrafluoro-2-(norbornan-2-yl)ethane sulfonate. FIG. 17 shows the $^1$H-NMR analysis results of this compound.

This compound is referred to as "acid generator (A-8)".

Synthesis of Acid-Cleavable Group-Containing Resin

Synthesis Example 9

101 g of 4-acetoxystyrene, 5 g of styrene, 42 g of 4-t-butoxystyrene, 6 g of azobisisobutyronitrile (AIBN), and 1 g of t-dodecylmercaptan were dissolved in 160 g of propylene glycol monomethyl ether. The mixture was polymerized for 16 hours at 70° C. in a nitrogen atmosphere. After polymerization, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of water were added. The mixture was hydrolyzed for 8 hours while refluxing at the boiling point. After the reaction, the solvent and triethylamine were evaporated under reduced pressure. The resulting resin was dissolved in acetone and the solution was added dropwise to a large quantity of water to coagulate the resin. The resulting white powder was filtered and dried overnight at 50° C. under reduced pressure.

The resin was found to have Mw and Mw/Mn of 16,000 and 1.7 respectively. The result of $^{13}$C-NMR analysis confirmed that the copolymerization molar ratio of 4-hydroxystyrene, styrene, and 4-t-butoxystyrene of the copolymer was 72:5:23.

This resin is referred to as a "resin (B-1)".

Mw and Mn of the resin (B-1) and the following resins (B-2) through (B-13) were measured by gel permeation chromatography (GPC) using GPC columns (manufactured by Tosoh Corp., G2000HXL×2, G3000HXL×1, G4000HXL×1) under the following conditions. Flow rate: 1.0 ml/minute, eluate: tetrahydrofuran, column temperature: 40° C., standard reference material: monodispersed polystyrene.

Synthesis Example 10

100 g of 4-acetoxystyrene, 25 g of t-butyl acrylate, 18 g of styrene, 6 g of AIBN, and 1 g of t-dodecylmercaptan were dissolved in 230 g of propylene glycol monomethyl ether. The mixture was polymerized for 16 hours at 70° C. in a nitrogen atmosphere. After polymerization, the reaction solution was added dropwise to a large quantity of hexane to coagulate and purify the resulting resin.

After the addition of 150 g of propylene glycol monomethyl ether to the resin, 300 g of methanol, 80 g of triethylamine, and 15 g of water were added. The mixture was hydrolyzed for 8 hours while refluxing at the boiling point. After the reaction, the solvent and triethylamine were evaporated under reduced pressure. The resulting resin was dissolved in acetone and the solution was added dropwise to a large quantity of water to coagulate the resin. The resulting white powder was filtered and dried overnight at 50° C. under reduced pressure.

The resin was found to have Mw and Mw/Mn of 11,500 and 1.6 respectively. The result of $^{13}$C-NMR analysis confirmed that the copolymerization molar ratio of 4-hydroxystyrene, t-butyl acrylate, and styrene of the copolymer was 61:19:20.

This resin is referred to as a "resin (B-2)".

Synthesis Example 11

176 g of 4-t-butoxystyrene was anionically polymerized at −78° C. in 500 ml of tetrahydrofuran using n-butyllithium as a catalyst. After polymerization, the resulting resin solution was coagulated in methanol to obtain 150 g of white poly(4-t-butoxystyrene).

150 g of poly(4-t-butoxystyrene) was dissolved in 600 g of dioxane. After the addition of diluted hydrochloric acid, the mixture was hydrolyzed at 70° C. for 2 hours. The reaction product was added dropwise to a large quantity of water, thereby causing the resin to coagulate. A step of dissolving the resulting resin in acetone and adding dropwise to a large quantity of water to coagulate the resin was repeated. The resulting white powder was filtered and dried overnight at 50° C. under reduced pressure.

The Mw and Mw/Mn of this resin were 10,400 and 1.10, respectively. $^{13}$C-NMR analysis confirmed that only part of t-butyl group in the poly(4-t-butoxystyrene) had a hydrolyzed structure and the molar ratio of 4-t-butoxystyrene and 4-hydroxystyrene was 68:32.

This resin is referred to as a "resin (B-3)".

Synthesis Example 12

25 g of a copolymer of 4-hydroxystyrene and 4-t-butoxystyrene (copolymerization molar ratio, 90:10) was dissolved in 100 q of n-butyl acetate. Nitrogen gas was bubbled through the solution for 30 minutes. After the addition of 3.3 g of ethyl vinyl ether and 1 g of pyridinium p-toluenesulfonate as a catalyst, the mixture was reacted at room temperature for 12 hours. The reaction solution was added dropwise to a 1% ammonium aqueous solution to coagulate the resin. The resin was filtered and dried overnight in a vacuum drier at 50° C.

Mw and Mw/Mn of this resin were respectively 13,000 and 1.01. As a result of $^{13}$C-NMR analysis, the resin was found to have a structure in which 23 mol % of hydrogen atoms of the phenolic hydroxyl group in poly(4-hydroxystyrene) was replaced by ethoxyethyl groups, and 10 mol % by t-butyl groups.

This resin is referred to as a "resin (B-4)".

Synthesis Example 13

5 g of norbornene, 11 g of maleic anhydride, 11 g of 8-hydroxytetracyclo[4.4.0.1$^{2,5}$.1$^{7,10}$]dodec-3-ene, and 23 g of 2-methyl-2-adamantyl methacrylate were dissolved in 50 g of tetrahydrofuran to obtain a homogeneous solution. After injection of nitrogen for 30 minutes, 3 g of AIBN was added. The mixture was heated to 65° C. and stirred for 6 hours at this temperature. After polymerization, the reaction solution was cooled to room temperature and diluted with 50 g of tetrahydrofuran. The diluted solution was poured into 1,000 ml of n-hexane. The precipitated white powder was collected by filtration and dried to obtain a resin.

This resin was a copolymer with an Mw of 6,100, having a copolymerization ratio of norbornene: maleic anhydride: 8-hydroxytetracyclo[4.4.0.1$^{2,5}$.1$^{7,10}$]dodec-3-ene: 2-methyl-2-adamantyl methacrylate=15:35:20:30.

This resin is referred to as a "resin (B-5)".

Synthesis Example 14

46.31 g of 2-methyl-2-adamantyl methacrylate and 53.69 g of the following compound (34) were dissolved in 200 g of 2-butanone to obtain a homogeneous solution, followed by the addition of 4.04 g of methyl azobisisovalerate as an initiator to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitate was filtrated and dried for 17 hours at 50° C. to obtain a resin.

This resin was a copolymer with an Mw of 12,200, having a copolymerization ratio of 2-methyl-2-adamantyl methacrylate: compound of formula (34)=40.6:59.4.

This resin is referred to as a "resin (B-6)".

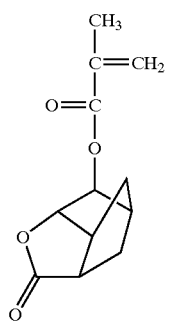

(34)

Synthesis Example 15

40.90 g of 2-methyl-2-adamantyl methacrylate, 15.47 g of 3-hydroxy-1-adamantyl methacrylate, and 43.64 g of the compound of formula (34) were dissolved in 200 g of 2-butanone to obtain a homogeneous solution, followed by the addition of 4.02 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitate was filtrated and dried for 17 hours at 50° C. to obtain a resin.

This resin was a copolymer with an Mw of 9,200, having a copolymerization ratio of 2-methyl-2-adamantyl methacrylate: 3-hydroxy-1-adamantyl methacrylate: compound of formula (34)=36.2:15.2:48.6.

This resin is referred to as a "resin (B-7)".

Synthesis Example 16

50.55 g of 2-methyl-2-adamantyl methacrylate, 25.49 g of 3-hydroxy-1-adamantyl methacrylate, and 23.97 g of the compound of formula (34) were dissolved in 200 g of 2-butanone to obtain a homogeneous solution, followed by the addition of 3.97 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitate was filtrated and dried for 17 hours at 50° C. to obtain a resin.

This resin was a copolymer with an Mw of 9,800, having a copolymerization ratio of 2-methyl-2-adamantyl methacrylate: 3-hydroxy-1-adamantyl methacrylate: compound of formula (34)=45.2:25.6:29.2.

This resin is referred to as a "resin (B-8)".

Synthesis Example 17

46.17 g of 2-methyl-2-adamantyl methacrylate, 5.179 g of 3-hydroxy-1-adamantyl methacrylate, and 48.65 g of the compound of formula (34) were dissolved in 200 g of 2-butanone to obtain a homogeneous solution, followed by the addition of 4.03 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitant was filtrated and dried for 17 hours at 50° C. to obtain a resin.

This resin was a copolymer with an Mw of 9,400, having a copolymerization ratio of 2-methyl-2-adamantyl methacrylate: 3-hydroxy-1-adamantyl methacrylate: compound of formula (34)=39.2:5.4:55.4.

This resin is referred to as a "resin (B-9)".

Synthesis Example 18

47.76 g of 2-ethyl-2-adamantyl methacrylate and 52.24 g of the compound shown by formula (34) were dissolved in 200 g of 2-butanone to obtain a homogeneous solution, followed by the addition of 3.93 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitate was filtrated and dried for 17 hours at 50° C. to obtain a resin.

This resin was a copolymer with an Mw of 11,600, having a copolymerization ratio of 2-ethyl-2-adamantyl methacrylate: compound of formula (34)=39.8:60.2.

This resin is referred to as a "resin (B-10)".

Synthesis Example 19

41.95 g of 1-ethylcyclohexyl methacrylate and 58.05 g of the compound shown by formula (34) were dissolved in 200 g of 2-butanone to obtain a homogeneous solution, followed by the addition of 4.37 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitate was filtrated and dried for 17 hours at 50° C. to obtain a resin.

This resin was a copolymer with an Mw of 13,400, having a copolymerization ratio of 1-ethylcyclohexyl methacrylate: compound of formula (34)=42.1:57.9.

This resin is referred to as a "resin (B-11)".

Synthesis Example 20

52.00 g of 2-ethyl-2-adamantyl methacrylate, 24.74 g of 3-hydroxy-1-adamantyl methacrylate, and 23.26 g of the compound of formula (34) were dissolved in 200 g of 2-butanone to obtain a homogeneous solution, followed by the addition of 3.85 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitant was filtrated and dried for 17 hours at 50° C. to obtain a resin.

This resin was a copolymer with an Mw of 8,700, having a copolymerization ratio of 2-ethyl-2-adamantyl methacrylate: 3-hydroxy-1-adamantyl methacrylate: compound of formula (34)=44.4:25.3:30.3.

This resin is referred to as a "resin (B-12)".

Synthesis Example 21

A three-necked flask was charged with 1.52 g of the silane compound of formula (35), 1.57 g of the silane compound of formula (36), 1.91 g of methyltriethoxysilane, 15 g of 4-methyl-2-pentanone, and 1.31 g of a 1.75% aqueous solution of oxalic acid. The mixture was reacted for six hours at 80° C. while stirring, followed by cooling with ice to terminate the reaction. The reaction mixture was poured into a separating funnel to remove the water layer. The organic layer was washed with ion-exchanged water until the reaction solution becomes neutral. The organic layer was evaporated under reduced pressure to obtain a resin.

The Mw of the resin was 2,500.

This resin is referred to as a "resin (B-13)".

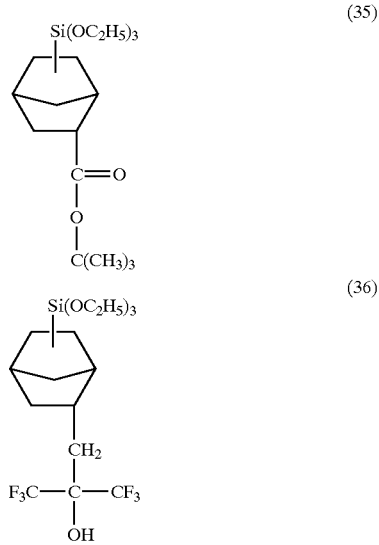

Synthesis Example 22

7 g of di-t-butyl carbonate was added to a solution in which 12 g of poly(4-hydroxystyrene) and 5 g of triethylamine were dissolved in 50 g of dioxane while stirring. The mixture was stirred for 6 hours at room temperature. Oxalic acid was then added to neutralize triethylamine. The reaction solution was dropped into a large quantity of water to coagulate the resin. The coagulated resin was washed with purified water several times. The resin was then filtered and dried at 50° C. overnight under reduced pressure.

Mw and Mw/Mn of this resin were respectively 9,200 and 1.8. As a result of $^{13}$C-NMR analysis, the resin was found to have a structure in which 30 mol % of hydrogen atoms of a phenolic hydroxyl group in poly(4-hydroxystyrene) was replaced by t-butoxycarbonyl groups.

This resin is referred to as a "resin (B-14)".

Synthesis Example 23

41.15 g of 2-methyl-2-adamantyl methacrylate, 5.19 g of 3-hydroxy-1-adamantyl methacrylate, and 53.66 g of the compound of formula (34) were dissolved in 200 g of 2-butanone to obtain a homogeneous solution, followed by the addition of 4.04 g of methyl azobisisovalerate to obtain a monomer solution.

Nitrogen gas was bubbled through a one liter three-necked flask containing 100 g of 2-butanone for 30 minutes. The temperature was increased to 80° C. while stirring. The above monomer solution was added by dripping at a rate of 10 ml/5 minutes, and the mixture was polymerized for 5 hours. The reaction solution was cooled to 30° C. or less and poured into 2,000 g of methanol. White precipitate produced was collected by filtration, mixed with 400 g of methanol, and washed twice. The white precipitant was filtrated and dried for 17 hours at 50° C. to obtain a resin.

This resin was a copolymer with an Mw of 9,800, having a copolymerization ratio of 2-methyl-2-adamantyl methacrylate: 3-hydroxy-1-adamantyl methacrylate: compound of formula (34)=35.8:5.1:59.1.

This resin is referred to as a "resin (B-15)".

Radiation-Sensitive Resin Composition

Examples 1–19 and Comparative Example 1

Components shown in Table 1 were mixed to prepare homogeneous solutions. The solutions were filtered through a membrane filter with a pore diameter of 0.2 μm to obtain composition solutions. The solution compositions were spin-coated on silicon wafers. PB was then performed under the conditions shown in Table 2 to form resist coatings with the thickness shown in Table 2.

As the radiation light sources in the examples: a stepper NSR 2205 EX 12B (numerical aperture: 0.55), manufactured by Nikon Corporation, was used as the KrF excimer laser (indicated by "KrF" in Table 2); an ArF excimer laser exposure apparatus (numerical aperture: 0.55), manufactured by Nikon Corporation, was used as the ArF excimer laser (indicated by "ArF" in Table 1); an $F_2$ excimer laser exposure apparatus XLS (numerical aperture: 0.60), manufactured by Ultratech Stepper, Inc., was used as the $F_2$ excimer laser (indicated by "$F_2$" in Table 1); a direct-write electron-beam lithography machine HL-700 (an apparatus wherein the acceleration voltage was improved to a range of 30 KeV to 50 KeV), manufactured by Hitachi, Ltd., was used as the electron beam. After conducting exposure in accordance with the conditions of Table 2, PEB was conducted in accordance with the conditions of Table 2.

The resist patterns were developed at 23° C. for 1 minute by a paddle method using a 2.38 wt % tetramethylammonium hydroxide aqueous solution. The resist coatings were then washed with purified water and dried to form resist patterns. The results of the evaluation of each resist are shown in Table 3.

Examples 20–23

Components shown in Table 4 were mixed to prepare homogeneous solutions. The solutions were filtered through a membrane filter with a pore diameter of 0.2 μm to obtain composition solutions. The solution compositions were spin-coated on silicon wafers. PB was then performed under the conditions shown in Table 5 to form resist coatings with the thickness shown in Table 5.

The resist coatings were exposed with a KrF excimer laser using a stepper NSR2205 EX12B (manufactured by Nikon Corp., numerical aperture: 0.55) and baked (PEB) under the conditions shown in Table 5. The resist patterns were developed at 23° C. for 1 minute by a paddle method using a 2.38 wt % tetramethylammonium hydroxide aqueous solution. The resist coatings were then washed with purified water and dried to form resist patterns. The results of the evaluation of each resist are shown in Table 6.

Evaluation of the resists of Examples 1–23 and Comparative Example 1 was carried out as follows.

Sensitivity:

Sensitivity was evaluated based on an optimum exposure dose which is a dose capable of forming a 1:1 line and space pattern (1L1S) with a line width of 0.22 µm, when a resist coating formed on a silicon wafer substrate is exposed to light, immediately followed by PEB, alkaline development, washing with water, and drying. In the examples using an ArF excimer laser, an optimum dose capable of forming a 0.16 µm line-and-space pattern (1L1S) with a 1:1 line width was used.

Resolution:

The minimum line and space (1L1S) dimension resolved by an optimum exposure dose was taken as the resolution.

Mask Pattern Dependency:

Resist coatings providing line patterns with a line width exceeding 70% of the designed line width for a 0.22 µm 1L10S pattern (0.22 µm line/2.2 µm space) upon exposure using an optimum dose were indicated by "good", otherwise the resist coatings were indicated by "poor". When an ArF exposure apparatus is used at an optimum dose, resist coatings providing line patterns with a line width exceeding 70% of the designed line width for a 0.16 µm 1L10S pattern (0.16 µm line/1.6 µm space) upon exposure using an optimum dose were indicated by "good", otherwise the resist coatings were indicated by "poor".

Mask Pattern Fidelity:

The difference (absolute value) between the line width of a 0.22 µm 1L5S pattern (0.22 µm line/1.1 µm space) and the design width (0.22 µm) produced upon exposure using an optimum dose was taken as mask pattern fidelity.

Examples 24–34 and Comparative Example 2

Each composition solution having components shown in Table 7 was evaluated. The evaluation results are shown in Table 9.

Evaluation of the resists of Examples 24–34 and Comparative Example 2 was carried out as follows.

Radiation Transmittance:

A composition solution was applied to a quartz plate by spin coating and post-baked on a hot plate at 130° C. for 60 seconds to obtain a resist coating with a thickness of 0.34 µm. The radiation transmittance of the resist coating was calculated from the absorbance at a wavelength of 193 nm and was employed as a standard for transparency in the deep UV ray region.

Sensitivity:

A solution composition was applied to a silicon wafer (ARC25) with a 820 Å thickness ARC25 film (manufactured by Brewer Science Corp.) coated on the surface by spin coating and post-baked on a hot plate under the conditions shown in Table 8 to obtain a resist coating with a thickness of 0.34 µm. The coating was exposed to radiation through a mask pattern using an ArF excimer laser exposure apparatus (manufactured by Nikon Corp., lens numerical aperture: 0.55). After performing PEB under the conditions shown in Table 8, the resist coating was developed at 25° C. for 80 seconds in a 2.38 wt % tetramethylammonium hydroxide aqueous solution, washed with water, and dried to form a positive-tone resist pattern. An optimum dose capable of forming a 0.16 µm line-and-space pattern (1L1S) with a 1:1 line width was taken as sensitivity.

Resolution:

The minimum line and space (1L1S) dimension resolved by an optimum exposure dose was taken as the resolution.

Pattern Profile:

The dimensions of the lower side Lb and the upper side La of the rectangular cross section of a line and space pattern (1L1S) with a line width of 0.16 µm were measured using a scanning electron microscope. A pattern shape which satisfied the formula "0.85<=La/Lb<=1" and was straight with no extended skirt was evaluated as "Good".

Defective Development:

Defective development was evaluated using a KLA 2112 or KLA 2351 defect inspection apparatus (manufactured by KLA-Tencor Corporation) in accordance with the following method.

The wafer for defect inspection was prepared in the following manner. A solution composition was applied to a silicon wafer with an 820 Å thickness ARC25 film (manufactured by Brewer Science Corp.) coated on the surface to obtain a dried thickness of 0.30 µm. This silicon wafer was post-baked at 130° C. for 90 seconds. The entire surface of the wafer was exposed to a 5 mm×5 mm blank exposure using a full field exposure machine (manufactured by Nikon Corp.; S203B when KrF excimer laser was used and S306C when ArF excimer laser was used). After performing PEB at 103° C. for 90 seconds, the resist coatings were developed in a 2.38 wt % tetramethylammonium hydroxide aqueous solution at 25° C. for 30 seconds, washed with water, and dried to form an inspection wafer.

Next, the inspection wafer was inspected for the number of exposure defects of 0.15 µm or more in the exposed area using a KLA 2112 or KLA 2351 defect inspection apparatus (manufactured by KLA-Tencor Corporation). The total number of defective clusters and unclusters extracted from the difference caused by superposing the pixels and a reference image was detected by observing at an array mode.

The other acid generators, alkali-soluble resins, acid diffusion controllers, crosslinking agents, other additives, and solvents indicated in Tables 1 and 9 are as follows.

Other Acid Generators
a-1: N-(trifluoromethylsulfonyloxy)bicyclo[2.2.1]hept-5-ene-2,3-dicarboxyimide
a-2: Triphenylsulfonium trifluoromethanesulfonate
a-3: Bis(cyclohexylsulfonyl)diazomethane
a-4: 1-(4-n-butoxynaphthalen-1-yl) tetrahydrothiophenium nonafluoro-n-butanesulfonate Alkali-Soluble Resin
C-1: 4-Hydroxystyrene/styrene copolymer (copolymerization ratio: 78:22, Mw=3,100, Mw/Mn=1.13; VPS3020 (manufactured by Nippon Soda Co., Ltd.) <0)

Acid Diffusion Controller
D-1: tri-n-octylamine
D-2: triethanolamine
D-3: 2-phenylbenzimidazole
D-4: 2,6-dimethylaminopyridine
D-5: N-t-butoxycarbonyl-2-phenylbenzimidazole Crosslinking Agent
E-1: N,N,N,N-tetra(methoxymethyl)glycoluril Other additives
F-1: t-butyl deoxycholate
F-2: t-butoxycarbonylmethyl deoxycholate
F-3: t-butoxycarbonylmethyl lithocholate Solvent
G-1: ethyl lactate
G-2: ethyl 3-ethoxypropionate
G-3: propylene glycol monomethyl ether acetate
G-4: 2-Heptanone
G-5: Cyclohexanone
G-6: γ-Butyrolacton

TABLE 1

| | Acid generator | Resin | Acid diffusion controller | Crosslinking agent | Other additives | Solvent |
|---|---|---|---|---|---|---|
| Example 1 | A-1 (3) | B-1 (100) | D-3 (0.1) | — | — | G-1 (800) |
| Example 2 | A-2 (3) | B-1 (100) | D-2 (0.1) | — | — | G-1 (800) |
| Example 3 | A-3 (3) | B-1 (100) | D-4 (0.3) | — | — | G-1 (800) |
| Example 4 | A-4 (3) | B-1 (100) | D-3 (0.1) | — | — | G-1 (800) |
| Example 5 | A-3 (1) a-1 (6) | B-1 (100) | D-5 (0.2) | — | — | G-1 (400) G-3 (400) |
| Example 6 | A-3 (2) | B-2 (100) | D-2 (0.1) | — | — | G-1 (400) G-2 (400) |
| Example 7 | A-3 (2) | B-3 (100) | D-3 (0.1) | — | — | G-1 (400) G-3 (400) |
| Example 8 | A-2 (2) | B-4 (100) | D-1 (0.1) | — | — | G-1 (400) G-3 (400) |
| Example 9 | A-1 (2) | B-5 (90) | D-3 (0.1) | — | F-1 (10) | G-4 (700) G-5 (300) |
| Example 10 | A-1 (5) | B-6 (92) | D-3 (0.4) | — | F-2 (8) | G-3 (700) G-6 (50) |
| Example 11 | A-2 (2) | B-13 (100) | D-3 (0.1) | — | — | G-3 (1200) |
| Example 12 | A-2 (3) | B-1 (100) | D-3 (0.1) | — | — | G-1 (800) |
| Example 13 | A-2 (3) | C-1 (97) B-4 (3) | D-1 (0.1) | E-1 (7) | — | G-1 (550) G-2 (250) |
| Example 14 | A-1 (4) A-2 (1) | B-7 (90) B-11 (10) | D-3 (0.4) | — | — | G-4 (250) G-6 (550) |
| Example 15 | A-1 (4) A-5 (1) | B-7 (90) B-11 (10) | D-3 (0.3) | — | — | G-4 (250) G-6 (550) |
| Example 16 | A-1 (5) | B-8 (60) B-10 (40) | D-3 (0.4) | — | — | G-4 (800) |
| Example 17 | A-1 (5) | B-9 (100) | D-3 (0.4) | — | — | G-4 (800) |
| Example 18 | A-1 (4) A-2 (1) | B-12 (100) | D-3 (0.4) | — | — | G-4 (800) |
| Example 19 | A-1 (4) A-5 (1) | B-12 (100) | D-3 (0.3) | — | — | G-4 (800) |
| Comparative Example 1 | a-1 (3) | B-1 (100) | D-3 (0.1) | — | — | G-1 (400) G-3 (400) |

Unit in parenthesis: parts by weight

TABLE 2

| | Thickness (Å) | PB Temp (° C.) | PB Time (sec) | Radiation | PEB Temp (° C.) | PEB Time (sec) |
|---|---|---|---|---|---|---|
| Example 1 | 5,000 | 120 | 90 | KrF excimer laser | 130 | 90 |
| Example 2 | 5,000 | 120 | 90 | KrF excimer laser | 130 | 90 |
| Example 3 | 5,000 | 120 | 90 | KrF excimer laser | 130 | 90 |
| Example 4 | 5,000 | 120 | 90 | KrF excimer laser | 130 | 90 |
| Example 5 | 5,000 | 120 | 90 | KrF excimer laser | 130 | 90 |
| Example 6 | 5,000 | 140 | 90 | KrF excimer laser | 140 | 90 |
| Example 7 | 5,000 | 130 | 90 | KrF excimer laser | 130 | 90 |
| Example 8 | 5,000 | 100 | 90 | KrF excimer laser | 100 | 90 |
| Example 9 | 3,000 | 140 | 90 | ArF excimer laser | 140 | 90 |
| Example 10 | 3,300 | 130 | 90 | ArF excimer laser | 130 | 90 |
| Example 11 | 1,000 | 130 | 90 | $F_2$ excimer laser | 110 | 90 |
| Example 12 | 3,000 | 120 | 90 | Electron beam | 130 | 90 |
| Example 13 | 5,000 | 90 | 60 | KrF excimer laser | 110 | 90 |
| Example 14 | 3,300 | 130 | 90 | ArF excimer laser | 130 | 90 |
| Example 15 | 3,300 | 130 | 90 | ArF excimer laser | 130 | 90 |
| Example 16 | 3,300 | 130 | 90 | ArF excimer laser | 110 | 90 |
| Example 17 | 3,300 | 130 | 90 | ArF excimer laser | 130 | 90 |
| Example 18 | 3,300 | 130 | 90 | ArF excimer laser | 110 | 90 |
| Example 19 | 3,300 | 130 | 90 | ArF excimer laser | 110 | 90 |
| Comparative Example 1 | 5,000 | 120 | 90 | KrF excimer laser | 130 | 90 |

TABLE 3

| | Resolution | Sensitivity | Mask pattern dependency |
|---|---|---|---|
| Example 1 | 0.21 μm | 360 J/m$^2$ | Good |
| Example 2 | 0.21 μm | 320 J/m$^2$ | Good |
| Example 3 | 0.20 μm | 300 J/m$^2$ | Good |
| Example 4 | 0.20 μm | 350 J/m$^2$ | Good |
| Example 5 | 0.20 μm | 320 J/m$^2$ | Good |
| Example 6 | 0.21 μm | 390 J/m$^2$ | Good |
| Example 7 | 0.21 μm | 360 J/m$^2$ | Good |
| Example 8 | 0.20 μm | 380 J/m$^2$ | Good |
| Example 9 | 0.17 μm | 800 J/m$^2$ | Good |
| Example 10 | 0.15 μm | 300 J/m$^2$ | Good |
| Example 11 | 0.17 μm | 200 J/m$^2$ | Good |
| Example 12 | 0.16 μm | 4 μC | Good |
| Example 13 | 0.20 μm | 260 J/m$^2$ | Good |
| Example 14 | 0.15 μm | 260 J/m$^2$ | Good |
| Example 15 | 0.15 μm | 280 J/m$^2$ | Good |
| Example 16 | 0.15 μm | 320 J/m$^2$ | Good |
| Example 17 | 0.15 μm | 280 J/m$^2$ | Good |
| Example 18 | 0.15 μm | 240 J/m$^2$ | Good |
| Example 19 | 0.15 μm | 270 J/m$^2$ | Good |
| Comparative Example 1 | 0.21 μm | 320 J/m$^2$ | Poor |

TABLE 4

| | Acid generator | Resin | Acid diffusion controller | Solvent |
|---|---|---|---|---|
| Example 20 | A-6 (2) a-1 (6) | B-1 (100) | D-3 (0.2) | G-1 (400) G-3 (400) |
| Example 21 | A-6 (2) a-1 (6) | B-2 (100) | D-3 (0.2) | G-1 (400) G-3 (400) |
| Example 22 | A-6 (2) a-1 (6) | B-14 (100) | D-3 (0.2) | G-1 (400) G-3 (400) |
| Example 23 | A-6 (2) a-3 (6) | B-4 (100) | D-2 (0.2) | G-1 (400) G-3 (400) |

Unit in parenthesis: parts by weight

TABLE 5

| | Thickness (Å) | PB Temp (°C.) | PB Time (sec) | Radiation | PEB Temp (°C.) | PEB Time (sec) |
|---|---|---|---|---|---|---|
| Example 20 | 5,000 | 120 | 90 | KrF excimer laser | 130 | 90 |
| Example 21 | 5,000 | 120 | 90 | KrF excimer laser | 130 | 90 |
| Example 22 | 5,000 | 90 | 90 | KrF excimer laser | 100 | 90 |
| Example 23 | 5,000 | 100 | 90 | KrF excimer laser | 100 | 90 |

TABLE 6

| | Resolution | Sensitivity | Mask pattern fidelity |
|---|---|---|---|
| Example 20 | 0.18 μm | 310 J/m² | 10 |
| Example 21 | 0.20 μm | 330 J/m² | 12 |
| Example 22 | 0.20 μm | 290 J/m² | 8 |
| Example 23 | 0.18 μm | 300 J/m² | 4 |

TABLE 7

| | Acid generator | Resin | Acid diffusion controller | Other additives | Solvent |
|---|---|---|---|---|---|
| Example 24 | A-8 (5) | B-8 (92) | D-3 (0.10) | F-2 (8) | G-3 (700) |
| Example 25 | A-8 (5) | B-8 (92) | D-3 (0.10) | F-2 (8) | G-3 (700) |
| Example 26 | A-2 (5) | B-8 (92) | D-3 (0.30) | F-3 (8) | G-3 (700) |
| Example 27 | A-1 (5) | B-8 (92) | D-3 (0.30) | F-3 (8) | G-3 (700) |
| Example 28 | A-1 (5) | B-8 (92) | D-3 (0.30) | F-2 (8) | G-3 (700) |
| Example 29 | A-7 (5) | B-8 (92) | D-3 (0.15) | F-2 (8) | G-3 (700) |
| Example 30 | A-4 (5) | B-8 (92) | D-3 (0.10) | F-2 (8) | G-3 (700) |
| Example 31 | A-1 (5.5) | B-7 (65.8) B-15 (28.2) | D-5 (0.43) | F-2 (6) | G-4 (500) G-5 (200) |
| Example 32 | A-1 (5.5) | B-7 (65.8) B-15 (28.2) | D-5 (0.43) | F-2 (6) | G-4 (500) G-5 (200) |
| Example 33 | A-1 (5.5) | B-7 (28.2) B-15 (65.8) | D-5 (0.43) | F-2 (6) | G-3 (470) G-4 (200) G-5 (30) |
| Example 34 | A-1 (5.5) | B-7 (28.2) B-15 (65.8) | D-5 (0.43) | F-2 (6) | G-3 (470) G-4 (200) G-5 (30) |
| Comparative example 2 | a-4 (5) | B-8 (92) | D-3 (0.30) | F-2 (8) | G-3 (700) |

Unit in parenthesis: parts by weight

TABLE 8

| | Resist coating thickness (μm) | Substrate | PB Temperature (°C.) | PB Time (sec) | PEB Temperature (°C.) | PEB Time (sec) |
|---|---|---|---|---|---|---|
| Example 24 | 0.34 | ARC25 | 130 | 90 | 130 | 90 |
| Example 25 | 0.34 | ARC25 | 130 | 90 | 130 | 90 |
| Example 26 | 0.34 | ARC25 | 130 | 90 | 130 | 90 |
| Example 27 | 0.34 | ARC25 | 130 | 90 | 130 | 90 |
| Example 28 | 0.34 | ARC25 | 130 | 90 | 130 | 90 |
| Example 29 | 0.34 | ARC25 | 130 | 90 | 130 | 90 |
| Example 30 | 0.34 | ARC25 | 130 | 90 | 130 | 90 |
| Example 31 | 0.34 | ARC25 | 130 | 90 | 130 | 90 |
| Example 32 | 0.34 | ARC25 | 130 | 90 | 130 | 90 |
| Example 33 | 0.34 | ARC25 | 130 | 90 | 130 | 90 |
| Example 34 | 0.34 | ARC25 | 130 | 90 | 130 | 90 |
| Comparative example 2 | 0.34 | ARC25 | 130 | 90 | 130 | 90 |

TABLE 9

| | Radiation transmittance (%) | Sensitivity (J/m2) | Resolution (μm) | Pattern shape | Developing defects Amount | Exposure machine | Defect inspection apparatus |
|---|---|---|---|---|---|---|---|
| Example 24 | 71 | 238 | 0.13 | Good | 0 | S203B | KLA2115 |
| Example 25 | 71 | 238 | 0.13 | Good | 0 | S306C | KLA2351 |
| Example 26 | 69 | 232 | 0.13 | Good | 12 | S203B | KLA2115 |
| Example 27 | 70 | 229 | 0.13 | Good | 0 | S203B | KLA2115 |
| Example 28 | 70 | 229 | 0.13 | Good | 0 | S306C | KLA2351 |
| Example 29 | 72 | 249 | 0.13 | Good | 4 | S203B | KLA2115 |
| Example 30 | 70 | 283 | 0.13 | Good | 1 | S203B | KLA2115 |
| Example 31 | 71 | 252 | 0.13 | Good | 0 | S203B | KLA2115 |
| Example 32 | 71 | 252 | 0.13 | Good | 0 | S306C | KLA2351 |
| Example 33 | 70 | 254 | 0.13 | Good | 0 | S203B | KLA2115 |
| Example 34 | 70 | 254 | 0.13 | Good | 0 | S306C | KLA2351 |
| Comparative example 2 | 70 | 224 | 0.13 | Good | 526 | S203B | KLA2115 |

The acid generator (I) of the present invention exhibits comparatively high combustibility and no bioaccumulation, and produces an acid exhibiting high acidity and a high boiling point. The acid generator exhibits high transparency to deep ultraviolet rays such as a KrF excimer laser, ArF excimer laser, $F_2$ excimer laser, or EUV, and electron beams, and produces the sulfonic acid (I-a) either as a photoacid generator in response to the above radiations or as a heat-sensitive acid generator in response to heat. Particularly, the acid generator can be suitably used as a photoacid generator in a radiation-sensitive resin composition that is useful for chemically amplified resists.

The sulfonic acid (I-a) of the present invention is useful as a component for forming an anti-reflection film on the upper or lower layer provided during the formation of a resist pattern. The sulfonate (1C) and sulfonyl halide compound (4A) of the present invention are useful as a reaction intermediate material for synthesizing the acid generator (I). Moreover, the sulfonic acid (I-a), sulfonate (1C), and sulfonyl halide compound (4A) are useful as raw materials for the synthesis of the sulfonic acid derivatives.

The radiation-sensitive resin composition of the present invention containing the acid generator (I) is responsive to deep ultraviolet rays such as a KrF excimer laser, ArF excimer laser, $F_2$ excimer laser, or EUV, and electron beams, is highly sensitive to radiation, has a moderately short diffusion length in the resist coating, displays excellent resolution, low dependency to mask pattern density, and can be suitably used in the field of microfabrication represented by the production of integrated circuits, which is expected to become more and more minute.

Obviously, numerous modifications and variations of the present invention are possible in light of the above teachings. It is therefore to be understood that, within the scope of the appended claims, the invention may be practiced otherwise than as specifically described herein.

What is claimed is:

1. An acid generator having a structure of the following formula (I),

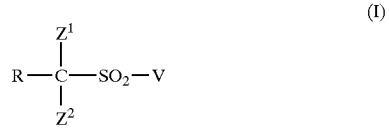

wherein V independently represents an oxygen atom, a halogen, or a monovalent organic group, and R is a monovalent organic group with a fluorine content of 50 wt % or less, a nitro group, a cyano group, or a hydrogen atom and $Z^1$ and $Z^2$ individually represent a fluorine atom or a linear or branched perfluoroalkyl group having 1–10 carbon atoms;

wherein the monovalent organic group with a fluorine content of 50 wt % or less is selected from the group consisting of: —$R^{11}$, —CO—$R^{11}$, —COO—$R^{11}$CON($R^{11}$)($R^{12}$), —S—$R^{11}$, —SO—$R^{11}$, and —$SO_2$—$R^{11}$ and $R^{12}$ individually represent a substituted or unsubstituted linear, branched or cyclic monovalent hydrocarbon group with 1–30 carbon atoms, a substituted or unsubstituted aryl group with 6–30 carbon atoms, or a substituted or unsubstituted monovalent heterocyclic organic group with 4–30 carbon atoms.

2. An acid generator having a structure of the following formula (I-1), (I-2), or (I-3),

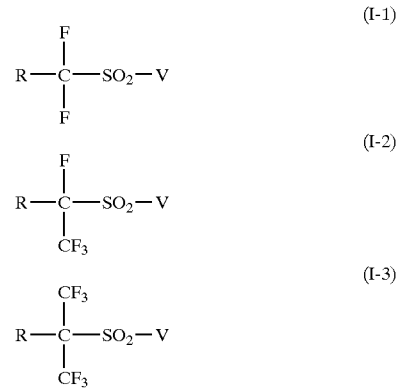

wherein V independently represents an oxygen atom, a halogen, or a monovalent organic group, and R individually represents a monovalent organic group with a fluorine content of 50 wt % or less, a nitro group, or a cyano group, wherein the monovalent organic group with a fluorine content of 50 wt % or less is selected from the group consisting of: —$R^{11}$, —CO—$R^{11}$, —COO—$R^{11}$, —CON($R^{11}$)($R^{12}$), —S—$R^{11}$, —$SO_2$—$R^{11}$, and —$SO_2$—$R^{11}$ wherein $R^{11}$ and $R^{12}$ individually represent a substituted or unsubstituted linear, branched or cyclic monovalent hydrocarbon group with 1–30 carbon atoms, a substituted or unsubstituted aryl group with 6–30 carbon atoms, or a substituted or unsubstituted monovalent heterocyclic organic group with 4–30 carbon atoms.

3. An acid generator having a structure of the following formula (I-A) or (I-B),

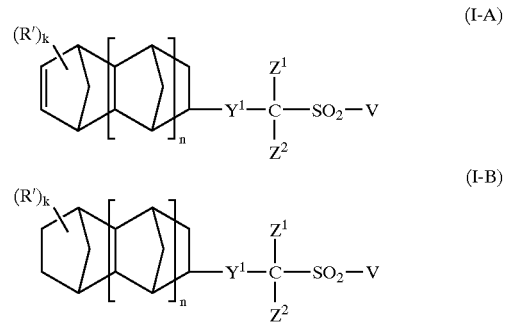

wherein V independently represents an oxygen atom, a halogen, or a monovalent organic group, $Z^1$ and $Z^2$ individually represent a fluorine atom or a linear or branched perfluoroalkyl group having 1–10 carbon atoms, $Y^1$ represents a single-bond or divalent group, R' represents a monovalent or divalent substituent, k is an integer of 0 or more, and n is an integer from 0–5.

4. An acid generator which is an onium sulfonate compound shown by the following formula (I),

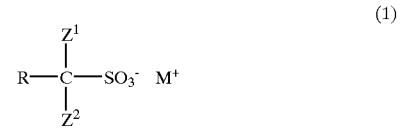

wherein R is a monovalent organic group with a fluorine content of 50 wt % or less, a nitro group, or a cyano group, $Z^1$ and $Z^2$ individually represent a fluorine atom or a linear or branched perfluoroalkyl group having 1–10 carbon atoms, and M⁺ is a monovalent onium cation.

5. An acid generator which is an onium sulfonate compound shown by the following formula (I-A) or (I-B),

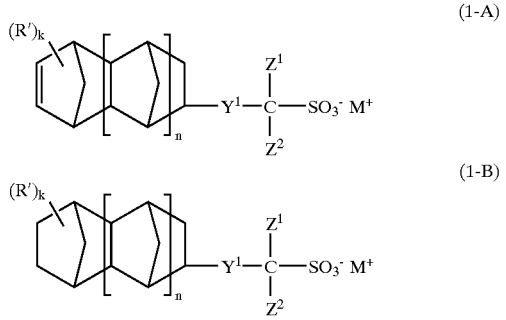

wherein $Z^1$ and $Z^2$ individually represent a fluorine atom or a linear or branched perfluoroalkyl group having 1–10 carbon atoms, $Y^1$ represents a single-bond or divalent group, R' represents a monovalent or divalent substituent, k is an integer of 0 or more, n is an integer from 0–5, and M⁺ is a monovalent onium cation.

6. The acid generator according to claim 5, wherein M⁺ is a sulfoniwn cation shown by the following formula (i),
wherein $R^1$, $R^2$, and $R^3$ individually represents a substituted or unsubstituted, linear or branched alkyl group having 1–10 carbon atoms, a substituted or unsubstituted aryl group having 6–18 carbon atoms, or two or more of the groups $R^1$, $R^2$, and $R^3$ form a ring together with the sulfur atom in the formula.

7. The acid generator according to claim 5, wherein M+ is an jodonium cation of the following formula (ii),

wherein $R^4$ and $R^5$ individually represent a substituted or unsubtituted, linear or branched alkyl group having 1–10 carbon atoms, a substituted or unsubstituted aryl group having 6–18 carbon atoms, or $R^4$ and $R^5$ form a ring together with the iodine atom in the formula.

8. An acid generator which is an N-sulfonyloxyimide compound of the following formula (2),

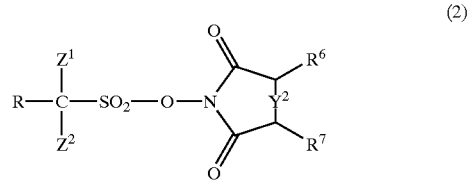

wherein R is a monovalent organic group with a fluorine content of 50 weight % or less, a nitro group, a cyano group, or a hydrogen atom, $Z^1$ and $Z^2$ individually represent a fluorine atom or a linear or branched perfluoroalkyl group having 1–10 carbon atoms, $R^6$ and $R^7$ individually represent a hydrogen atom or a substituted or unsubstituted monovalent organic group, or $R^6$ and $R^7$ form a ring together with the carbon atoms, each bonding to either the group $R^6$ or $R^7$, and $Y^2$ is a single bond, a double bond, or a divalent organic group.

9. An acid generator which is an N-sulfonyloxyimide compound of the following formula (2-A) or (2-B),

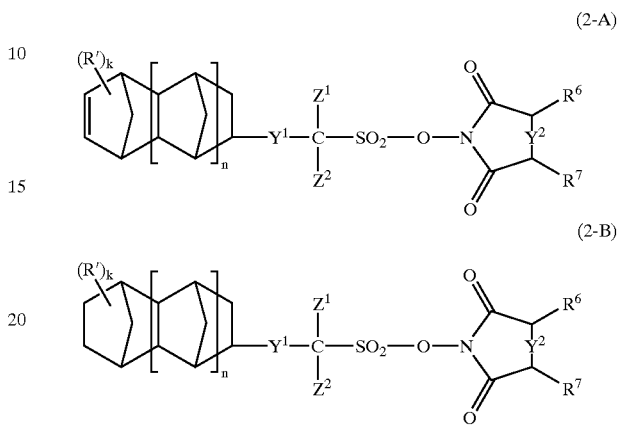

wherein $Z^1$ and $Z^2$ individually represent a fluorine atom or a linear or branched perfluoroalkyl group having 1–10 carbon atoms, $Y^1$ represents a single-bond or divalent group, R' represents a monovalent or divalent substituent, k is an integer of 0 or more, n is an integer from 0–5, $R^6$ and $R^7$ individually represent a hydrogen atom or a substituted or unsubstituted monovalent organic group, or $R^6$ and $R^7$ form a ring together with the carbon atoms, each bonding to either the group $R^6$ or $R^7$, and $Y^2$ is a single bond, a double bond, or a divalent organic group.

10. A sulfonic acid of the following formula (I-a),

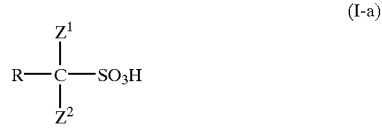

wherein R is a monovalent organic group with a fluorine content of 50 wt % or less, a nitro group, a cyano group, $Z^1$ and $Z^2$ individually represent a fluorine atom or a linear or branched perfluoroalkyl group having 1–10 carbon atoms;
wherein the monovalent organic group is selected from the group consisting of: —$R^{11}$, —CO—$R^{11}$, —COO—$R^{11}$, —CON($R^{11}$)($R^{12}$), —S—$R^{11}$, —SO-$R^{11}$, and —SO₂—$R^{11}$ wherein $R^{11}$ and $R^{12}$ individually represent a substituted or unsubstituted linear, branched or cyclic monovalent hydrocarbon group with 1–30 carbon atoms, a substituted or unsubstituted aryl group with 6–30 carbon atoms, or a substituted or unsubstituted monovalent heterocyclic organic group with 4–30 carbon atoms.

11. A sulfonate of the following formula (2C),

wherein R is a monovalent organic group with a fluorine content of 50 wt % or less, a nitro group, a cyano group, or a hydrogen atom, $Z^1$ and $Z^2$ are individually a fluorine atom or a linear or branched perfluoroalkyl group having 1–10 carbon atoms, and M is an Na, K, or Li;

wherein the monovalent organic group is selected from the group consisting of: $-R^{11}$, $-CO-R^{11}$, $-COO-R^{11}$, $-CON(R^{11})(R^{12})$, $-S-R_{11}$, $-SO-R^{11}$, and $-SO_2-R^{11}$ wherein $R^{11}$ and $R^{12}$ individually represent a substituted or unsubstituted linear, branched or cyclic monovalent hydrocarbon group with 1–30 carbon atoms, a substituted or unsubstituted aryl group with 6–30 carbon atoms, or a substituted or unsubstituted monovalent heterocyclic organic group with 4–30 carbon atoms.

12. A sulfonyl halide compound of the following formula (4A),

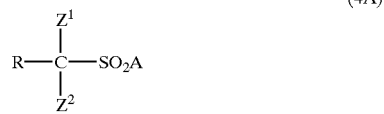

(4A)

wherein R represents a monovalent organic group with a fluorine content of 50 wt % or less, a nitro group, a cyano group, $Z^1$ and $Z^2$ are individually a fluorine atom or a linear or branched perfluoroalkyl group having 1–10 carbon atoms, and A is a halogen atom;

wherein the monovalent organic group is selected from the group consisting of: $-R^{11}$, $-CO-R^{11}$, $-COO-R^{11}$, $-CON(R^{11})(R^{12})$, $-S-R^{11}$, $-SO-R^{11}$, and $-SO_2-R^{11}$ wherein $R^{11}$ and $R^{12}$ individually represent a substituted or unsubstituted linear, branched or cyclic monovalent hydrocarbon group with 1–30 carbon atoms, a substituted or unsubstituted aryl group with 6–30 carbon atoms, or a substituted or unsubstituted monovalent heterocyclic organic group with 4–30 carbon atoms.

13. A positive-tone radiation-sensitive resin composition comprising: (A) the acid generator of claim 1 and (B) an alkali soluble or alkali low soluble resin comprising an acid-cleavable group that becomes soluble in alkali when the acid-cleavable group dissocaites.

14. A positive-tone radiation-sensitive resin composition comprising: (A) the acid generator of claim 1, (C) an alkali soluble resin, and (D) an alkali solubility control agent.

15. A negative-tone radiation-sensitive resin composition comprising (A) the acid generator according to claim 1, (C) an alkali soluble resin, and (B) a compound which can crosslink an alkali soluble resin in the presence of an acid.

16. An acid generator having a structure of the following formula (I-2),

(I-2)

wherein R individually represents a monovalent organic group with a fluorine content of 50 wt % or less, a nitro group, a cyano group, or a hydrogen atom.

17. A positive-tone radiation-sensitive resin composition comprising: (A) the acid generator of claim 5 and (B) an alkali soluble or alkali low soluble resin comprising an acid-cleavable group that becomes soluble in alkali when the acid-cleavable group dissociates.

18. A positive-tone radiation-sensitive resin composition comprising: (A) the acid generator of claim 6 and (B) an alkali soluble or alkali low soluble resin comprising an acid-cleavable group that becomes soluble in alkali when the acid-cleavable group dissociates.

19. A positive-tone radiation-sensitive resin composition comprising: (A) the acid generator of claim 7 and (B) an alkali soluble or alkali low soluble resin comprising an acid-cleavable group that becomes soluble in alkali when the acid-cleavable group dissociates.

20. A positive-tone radiation-sensitive resin composition comprising: (A) the acid generator of claim 9 and (B) an alkali soluble or alkali low soluble resin comprising an acid-cleavable group that becomes soluble in alkali when the acid-cleavable group dissociates.

21. A positive-tone radiation-sensitive resin composition comprising: (A) an acid generator as set forth in claim 3 and (B) an alkali soluble resin comprising an acid-cleavable group that becomes soluble in alkali when the acid-cleavable group dissociates.

* * * * *

UNITED STATES PATENT AND TRADEMARK OFFICE
CERTIFICATE OF CORRECTION

PATENT NO. : 6,908,722 B2
APPLICATION NO. : 10/183441
DATED : June 21, 2005
INVENTOR(S) : Satoshi Ebata et al.

It is certified that error appears in the above-identified patent and that said Letters Patent is hereby corrected as shown below:

Column 79, line 58, "—COO—$R^{11}$ CON" should read -- —COO—$R^{11}$, CON--.

Column 81, line 41, "is an jodonium" should read --is an iodonium--.

Column 82, line 58, "following formula (2C)," should read --following formula (1C),--.

Column 83, line 5, "—S—$R_{11}$" should read -- —S—$R^{11}$--.

Column 83, line 41, "dissocaites" should read --dissociates--.

Signed and Sealed this

Tenth Day of April, 2007

JON W. DUDAS
*Director of the United States Patent and Trademark Office*